US012484900B2

(12) United States Patent
Ryle et al.

(10) Patent No.: US 12,484,900 B2
(45) Date of Patent: Dec. 2, 2025

(54) SYSTEMS AND SUBSYSTEMS FOR ROLLING A SURGICAL INSTRUMENT INCLUDING ARTICULATION CABLES

(71) Applicant: CILAG GMBH INTERNATIONAL, Zug (CH)

(72) Inventors: William Claiborne Ryle, Cincinnati, OH (US); Douglas Marriott, Cincinnati, OH (US); Paul Moubarak, Cincinnati, OH (US); Samantha A. Grace-Mudd, Cincinnati, OH (US); Zachary Miller, Cincinnati, OH (US); Michael Dixon, Cincinnati, OH (US); Hannah Johnson Goebel, Cincinnati, OH (US); Shiv Wadwani, Cincinnati, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 0 days.

(21) Appl. No.: 18/775,249

(22) Filed: Jul. 17, 2024

(65) Prior Publication Data

US 2025/0025166 A1 Jan. 23, 2025

Related U.S. Application Data

(60) Provisional application No. 63/515,020, filed on Jul. 21, 2023, provisional application No. 63/640,289, filed on Apr. 30, 2024.

(51) Int. Cl.
*A61B 34/30* (2016.01)
*A61B 17/072* (2006.01)
(Continued)

(52) U.S. Cl.
CPC ...... *A61B 17/07207* (2013.01); *A61B 17/072* (2013.01); *A61B 34/30* (2016.02);
(Continued)

(58) Field of Classification Search
CPC .......................... A61B 17/07207; A61B 34/30
See application file for complete search history.

(56) References Cited

U.S. PATENT DOCUMENTS 7,691,098 B2 4/2010 Wallace et al.
8,827,134 B2 9/2014 Viola et al.
(Continued)

FOREIGN PATENT DOCUMENTS

CN 105682567 B 6/2016
EP 3511413 B1 7/2022
(Continued)

OTHER PUBLICATIONS

International Searching Authority, International Search Report and Written Opinion in Related PCT Application No. PCT/IB2024/056966, Dated Jan. 9, 2025.

*Primary Examiner* — Nathaniel C Chukwurah
(74) *Attorney, Agent, or Firm* — Troutman Pepper Locke LLP

(57) ABSTRACT

A surgical instrument designed to operate with a robotic platform is disclosed. The surgical instrument assembly includes a shaft, an end effector, a knife firing subsystem to actuate functions of the end effector, an articulation subsystem that is actuatable to articulate the end effector, an articulation joint about which the end effector articulates, a roll subsystem to roll the shaft, and a housing that couples to the robotic platform. A maypole tube is further provided, around which one or more articulation cables can wrap when the end effector is rotated.

12 Claims, 49 Drawing Sheets

(51) Int. Cl.
*A61B 34/00* (2016.01)
*A61B 17/00* (2006.01)

(52) U.S. Cl.
CPC .... *A61B 34/71* (2016.02); *A61B 2017/00199* (2013.01); *A61B 2017/00314* (2013.01); *A61B 2017/00323* (2013.01); *A61B 2017/00367* (2013.01); *A61B 2017/00398* (2013.01); *A61B 2017/00477* (2013.01); *A61B 2017/07257* (2013.01); *A61B 2017/07264* (2013.01); *A61B 2017/07271* (2013.01); *A61B 2017/07278* (2013.01); *A61B 2017/07285* (2013.01); *A61B 2034/301* (2016.02); *A61B 2034/715* (2016.02)

(56) References Cited

U.S. PATENT DOCUMENTS

| | | | |
|---|---|---|---|
| 9,289,208 | B1 | 3/2016 | Knodel et al. |
| 9,642,620 | B2 | 5/2017 | Baxter, III et al. |
| 10,478,185 | B2 | 11/2019 | Nicholas |
| 11,154,299 | B2 | 10/2021 | Shelton, IV et al. |
| 11,197,672 | B2 | 12/2021 | Dunki-Jacobs et al. |
| 11,278,279 | B2 | 3/2022 | Morgan et al. |
| 2011/0248064 | A1 | 10/2011 | Marczyk et al. |
| 2012/0205421 | A1 | 8/2012 | Shelton, IV |
| 2013/0274722 | A1 | 10/2013 | Kostrzewski et al. |
| 2014/0276722 | A1 | 9/2014 | Parihar et al. |
| 2014/0276931 | A1 | 9/2014 | Parihar et al. |
| 2015/0230796 | A1 | 8/2015 | Calderoni et al. |
| 2015/0374396 | A1 | 12/2015 | Strobl |
| 2018/0008265 | A1 | 1/2018 | Hatanaka |
| 2019/0099181 | A1 | 4/2019 | Shelton, IV et al. |
| 2019/0239967 | A1 | 8/2019 | Ragosta et al. |
| 2020/0138463 | A1 | 5/2020 | Kostrzewski et al. |
| 2020/0397433 | A1 | 12/2020 | Lytle, IV et al. |
| 2021/0059773 | A1 | 3/2021 | Overmyer et al. |
| 2021/0186494 | A1 | 6/2021 | Shelton, IV et al. |
| 2022/0031320 | A1 | 2/2022 | Hall et al. |
| 2022/0031322 | A1 | 2/2022 | Parks |
| 2022/0031323 | A1 * | 2/2022 | Witte .................... A61B 17/29 |
| 2022/0031345 | A1 | 2/2022 | Witte |
| 2022/0071632 | A1 | 3/2022 | Patel |
| 2022/0218350 | A1 | 7/2022 | Shelton, IV et al. |
| 2022/0304679 | A1 | 9/2022 | Bakos et al. |
| 2022/0346790 | A1 | 11/2022 | Wellman |
| 2022/0378424 | A1 | 12/2022 | Huang et al. |
| 2023/0051222 | A1 | 2/2023 | Shelton, IV et al. |
| 2023/0120209 | A1 | 4/2023 | Parks et al. |
| 2023/0210527 | A1 | 7/2023 | Shelton, IV et al. |
| 2024/0366221 | A1 | 11/2024 | Marriott et al. |
| 2025/0120700 | A1 | 4/2025 | Fiebig et al. |

FOREIGN PATENT DOCUMENTS

| | | | |
|---|---|---|---|
| WO | 9424947 | A1 | 11/1994 |
| WO | 2013155155 | A2 | 10/2013 |
| WO | 2014158452 | A1 | 10/2014 |
| WO | 2018116013 | A1 | 6/2018 |

* cited by examiner

SYSTEMS AND SUBSYSTEMS FOR ROLLING A SURGICAL INSTRUMENT INCLUDING ARTICULATION CABLES

CROSS-REFERENCE TO RELATED APPLICATIONS

This application claims the benefit of and priority to U.S. Provisional Patent Application No. 63/515,020 filed Jul. 21, 2023 and U.S. Provisional Patent Application Ser. No. 63/640,289 filed Apr. 30, 2024, the disclosures of which are expressly incorporated herein by reference.

BACKGROUND

The present disclosure relates to surgical instruments and, in various arrangements, to surgical stapling and cutting instruments and staple cartridges for use therewith that are designed to staple and cut tissue.

SUMMARY

The disclosed technology can be for systems, devices, and subsystems for surgical instruments for robotic surgeries. The surgical instruments can have several subsystems that can be independently actuated to provide a specific action, such as closing and opening of an end effector of the stapler, articulation of the end effector, rolling of the end effector, and firing of staples within the end effector.

The disclosed technology describes a surgical instrument. The surgical instrument includes a shaft assembly that includes a shaft assembly including a rotatable outer shaft configured to rotate about a roll axis and a maypole tube housed within the outer shaft. The surgical instrument includes a firing rod that extends within the maypole tube and is configured to move a knife in an end effector. The surgical instrument includes one or more articulation cables, each articulation cable being configured (i) to be manipulable to cause rotation of the end effector about at least one of a pitch axis and a yaw axis and (ii) to wrap around the maypole tube when the rotatable outer shaft rotates about the roll axis.

The disclosed technology describes a control device for adjusting a length of cable, which can be one of a number of subsystems and/or subcomponents for a surgical instrument. The surgical instrument includes the cable and a shaft. The cable includes (i) a section with an initial length defined between a rotatable point of the cable that is rotatable with the shaft relative to a rotationally restrained proximal point of the cable and (ii) an initial tension at a zero degree roll angle. The control device is configured to receive a non-zero degree roll angle of the rotatable point of the cable that is rotated with the shaft relative to the rotationally restrained proximal point of the cable. The control device is configured to determine a change in length of the section of the cable, relative to the initial length, that maintains the cable at the initial tension. The control device is configured to calculate a cable compensation length by multiplying the determined change in length of the section of the cable by a factor. The control device is configured to deliver a signal to change the length of the section of the cable based on the calculated cable compensation length.

The disclosed technology describes a surgical system. The surgical system includes a surgical instrument including a housing. The surgical instrument includes a shaft assembly extending from the housing and including an outer shaft (configured to rotate about a roll axis and a maypole tube housed within the outer shaft. The surgical instrument includes a cable including a rotationally restrained point proximal the housing and a rotatable point that is rotatable with the outer shaft. The cable includes, at a zero-degree roll angle, a length defined between the rotationally restrained point and the rotatable point. The surgical system includes a control device for adjusting the length of the cable. The control device is configured to receive a non-zero degree roll angle of rotatable point of the cable relative to the rotationally restrained proximal point of the cable. The control device is configured to determine a change in length of the cable, relative to the length of the cable at the zero-degree roll angle, that maintains the cable at a same tension as the tension in the cable when the cable is at the zero-degree roll angle. The control device is configured to calculate a cable compensation length by multiplying the determined change in length of the cable by a factor. The control device is configured to deliver a signal to change the length of the cable based on the calculated cable compensation length.

DETAILED DESCRIPTION

Figure 1:
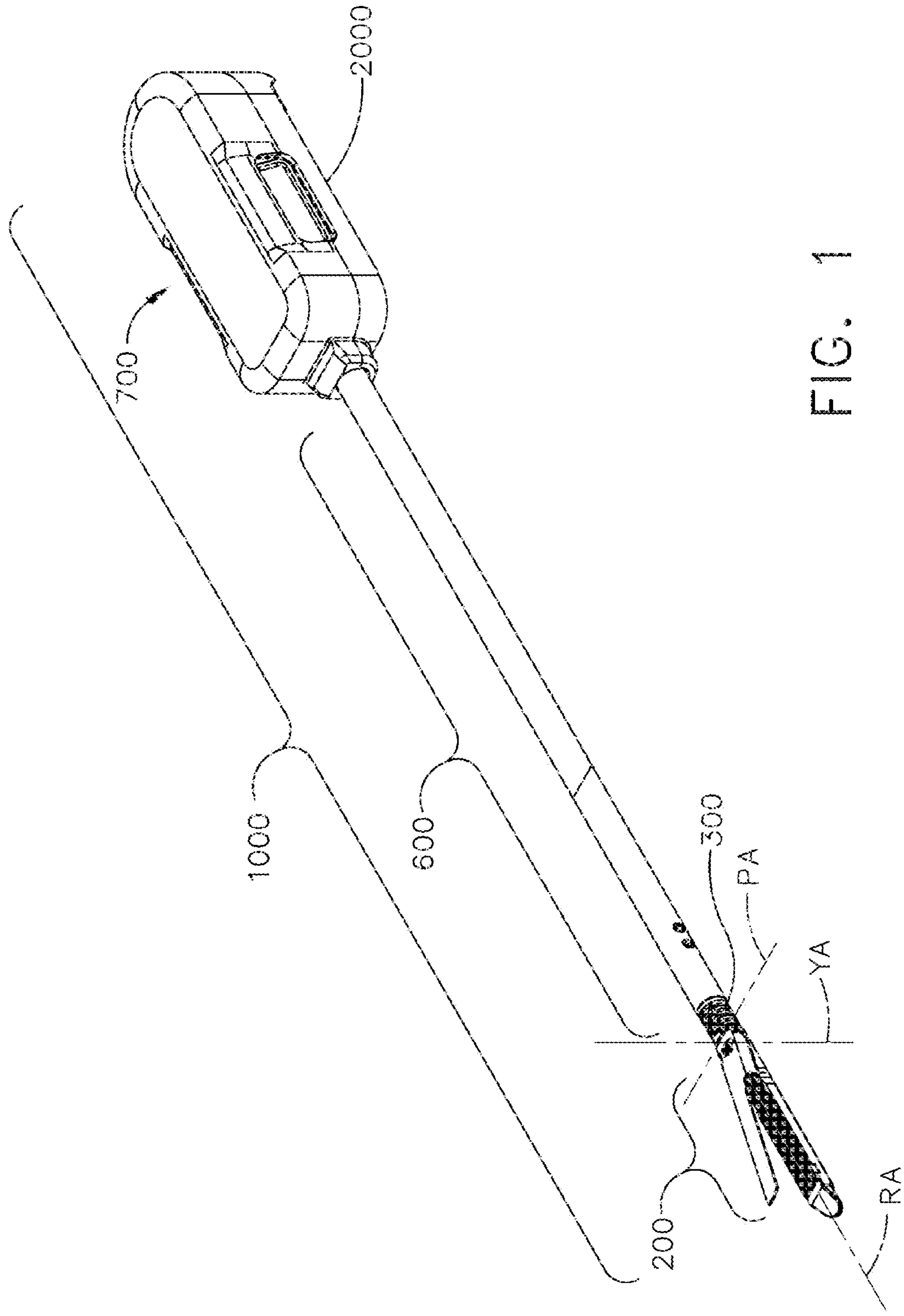
FIG. 1 is a schematic perspective view of a surgical system that includes a surgical instrument, in accordance with the disclosed technology.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g., "about 90%" may refer to the range of values from 71% to 99%.

The terms "proximal" and "distal" are used herein with reference to a robotic platform manipulating the housing portion of the surgical instrument. The term "proximal" refers to the portion closest to the robotic platform and the term "distal" refers to the portion located away from the robotic platform. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Furthermore, the use of "couple", "coupled", or similar phrases should not be construed as being limited to a certain number of components or a particular order of components unless the context clearly dictates otherwise.

Also, where alternative examples of certain aspects of the surgical instrument are described, in instances where the same reference numbers as that of previously described examples are used to label components in the alternative example(s), the structure and functionality of those components is the same unless otherwise noted.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The anvil is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. Other embodiments are envisioned which do not include an articulation joint. In other words, other elements described herein can be employed in embodiments where no articulation joint is provided without departing from the spirit and scope of the present disclosure. Similarly, the articulation joint can be employed in embodiments where other elements described herein are omitted.

I. OVERVIEW OF THE SURGICAL INSTRUMENT

Figure 2:
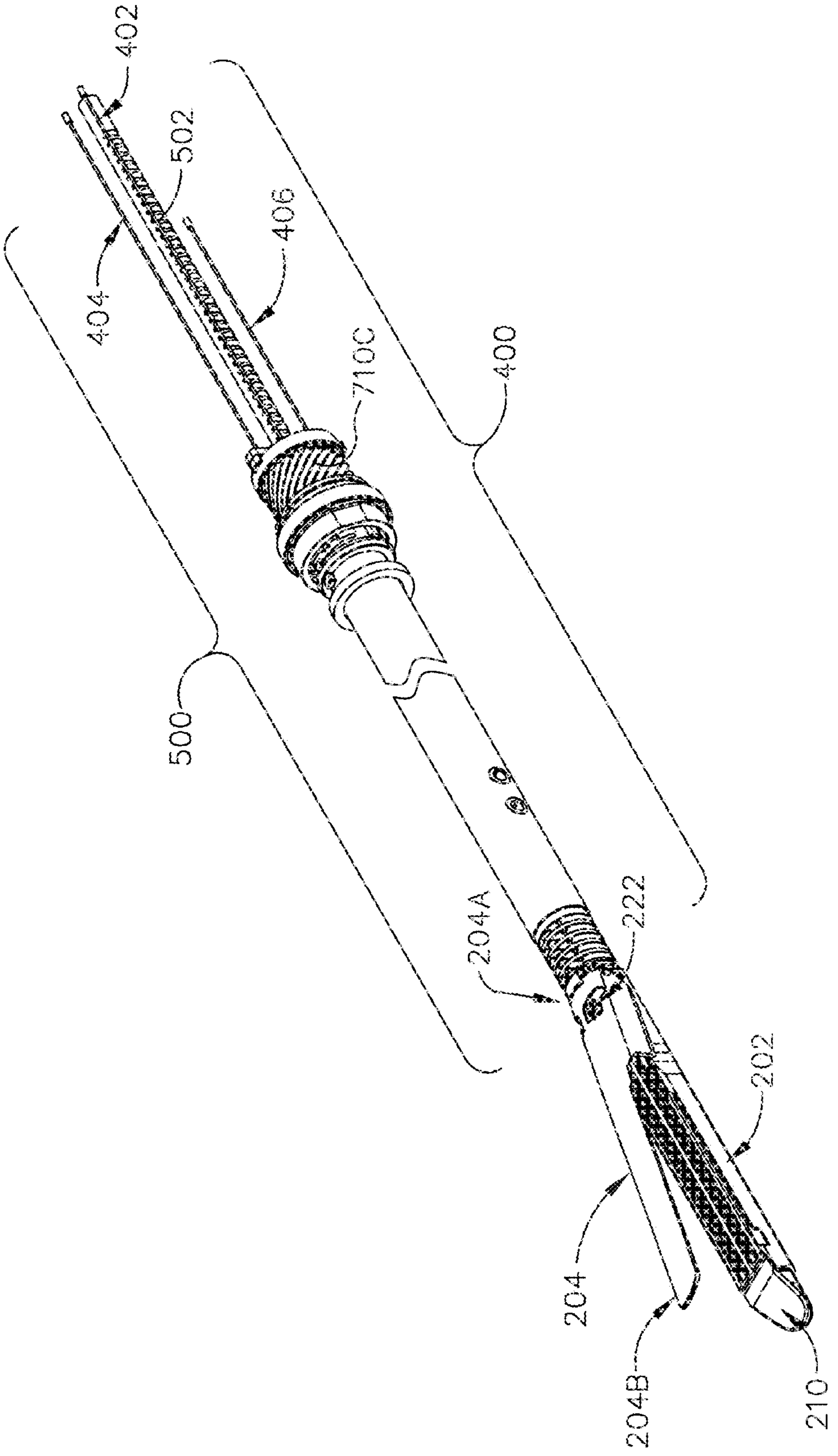
FIG. 2 is a schematic detail view of an end effector, articulation joint, and portions of a cable articulation subsystem, knife firing subsystem, and roll subsystem, in accordance with the disclosed technology.

A surgical instrument 1000 is illustrated in FIG. 1. As discussed in greater detail below, the surgical instrument 1000 is configured to grasp, clamp, incise, and seal patient tissue. The surgical instrument 1000 comprises an end effector 200, an articulation joint 300, an articulation drive subsystem 400 (FIG. 2) configured to articulate the end effector 200 about the articulation joint 300, a knife firing subsystem 500 (FIG. 2) configured to move the end effector between various positions (e.g., an open position, a grasping position, and a clamping position) and to incise and staple patient tissue, a roll subsystem 600 configured to roll the end effector 200 about a roll axis, and a housing 700.

II. OVERVIEW OF THE END EFFECTOR

Figure 3:
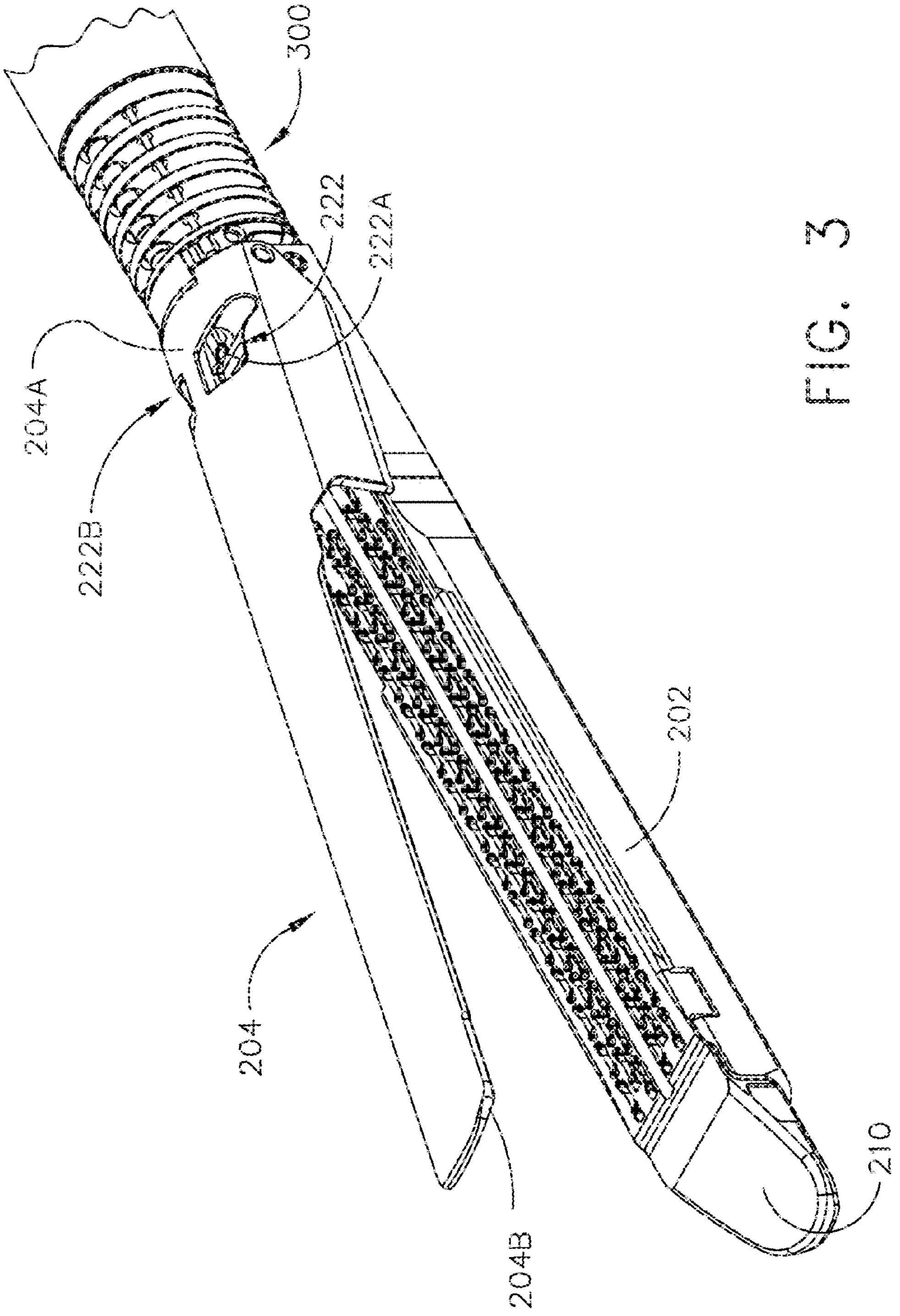
FIG. 3 is a schematic detail view of the end effector and the articulation joint, in accordance with the disclosed technology.
Figures 4, 5:
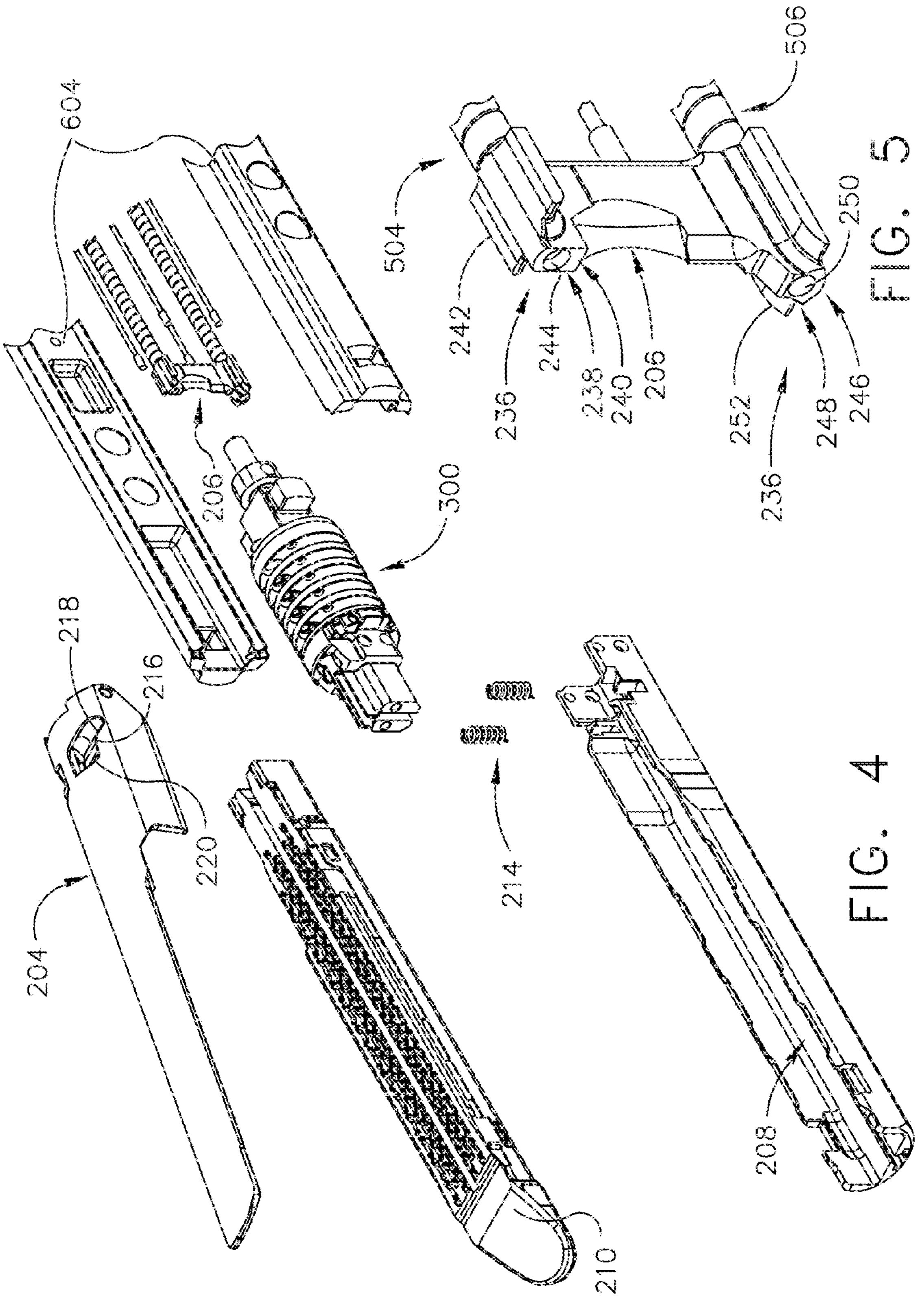
FIG. 4 is a schematic exploded view of a distal end of the surgical instrument, in accordance with the disclosed technology.
FIG. 5 is a schematic detail view of a knife, in accordance with the disclosed technology.
Figure 7:
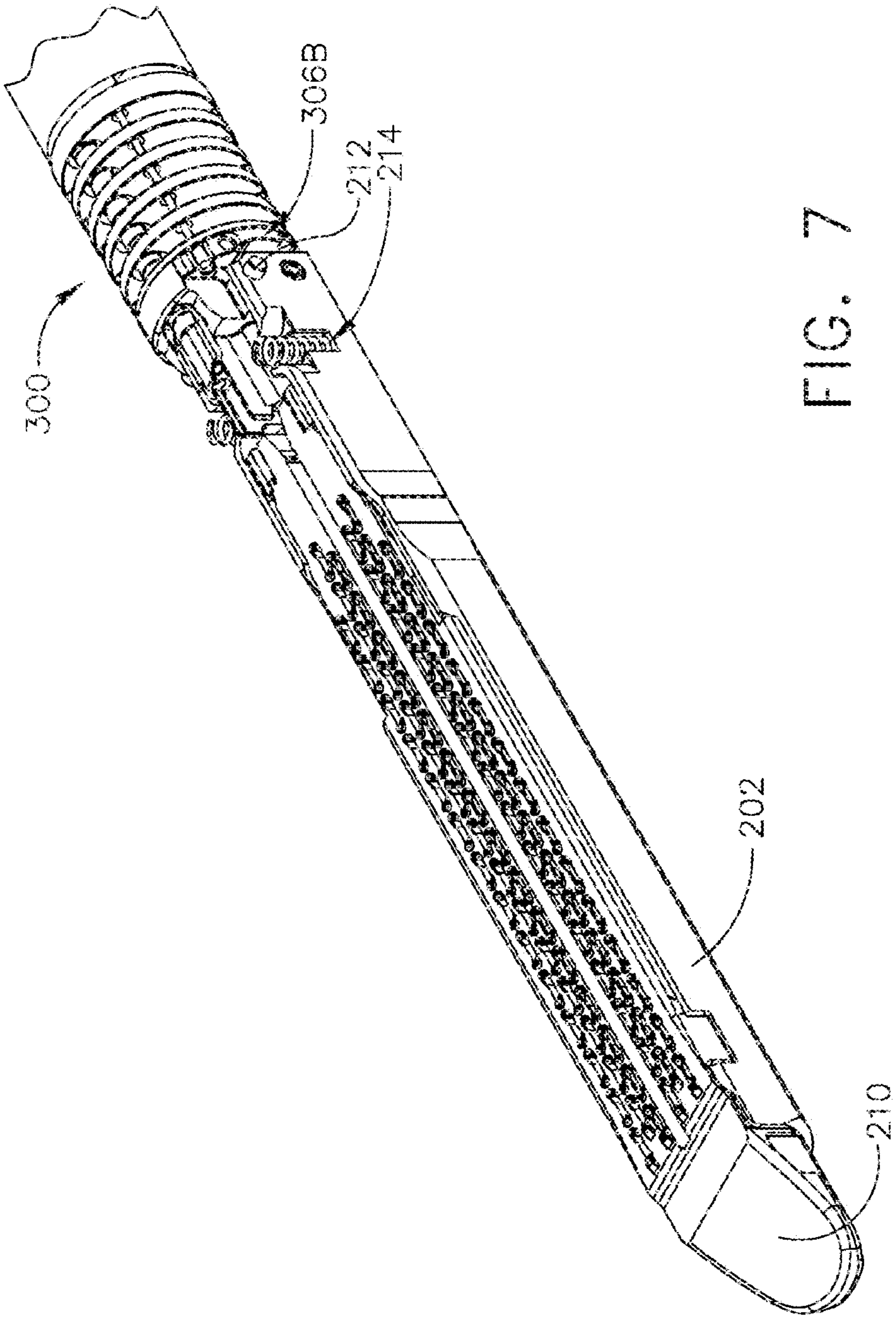
FIG. 7 is a schematic detail view of the end effector and the articulation joint, with an anvil of the end effector removed, in accordance with the disclosed technology.

The end effector 200 comprises a first jaw 202 and a second jaw 204 movable between an open position and a closed position. For clarity, first jaw 202 is herein also interchangeably used with "jaw 202" (which is also referred to in the art as a "channel") and second jaw 204 is used interchangeably with "anvil 204". The jaw 202 and anvil 204 may be elongated in form. The jaw 202 defines an elongated channel 208 for receiving a staple cartridge 210. The anvil 204 has a proximal end 204A, a distal end 204B, and a ramp surface 216 defined at the proximal end 204A, which is described in greater detail below with respect to FIGS. 4 and 9A-9D. The jaw 202 and anvil 204 are pivotally coupled via a pivot pin 212 that extends through the jaw 202 and the anvil 204. As seen in FIG. 7, one or more biasing springs 214 extend between the jaw 202 and anvil 204 to bias the anvil 204 to the open position. The ramp surface 216 may be visible via a kidney bean-shaped opening 222 (which may be formed as part of the manufacturing process to make the ramp surface 216) that has a first lateral end 216A and a second lateral end 216B. In other words, the kidney bean-shaped opening may be open at its lateral ends 222A, 222B (FIG. 3). As seen in FIG. 3, the ramp surface 216 forms a lower surface of the kidney bean-shaped opening 222. The ramp surface 216 can be arcuately shaped. For example, as shown particularly in FIGS. 4 and 9A-9D, it may be upwardly sloped at a first angle 218 and arcuately tapers, in a distal direction, to a substantially horizontal second angle 220. Ramp surface, by way of example, may include a single radius curve, a series of multi-radius curves, a series of multi-radius curves with a series of inflection points, and/or be linearly sloped.

Figure 8A:
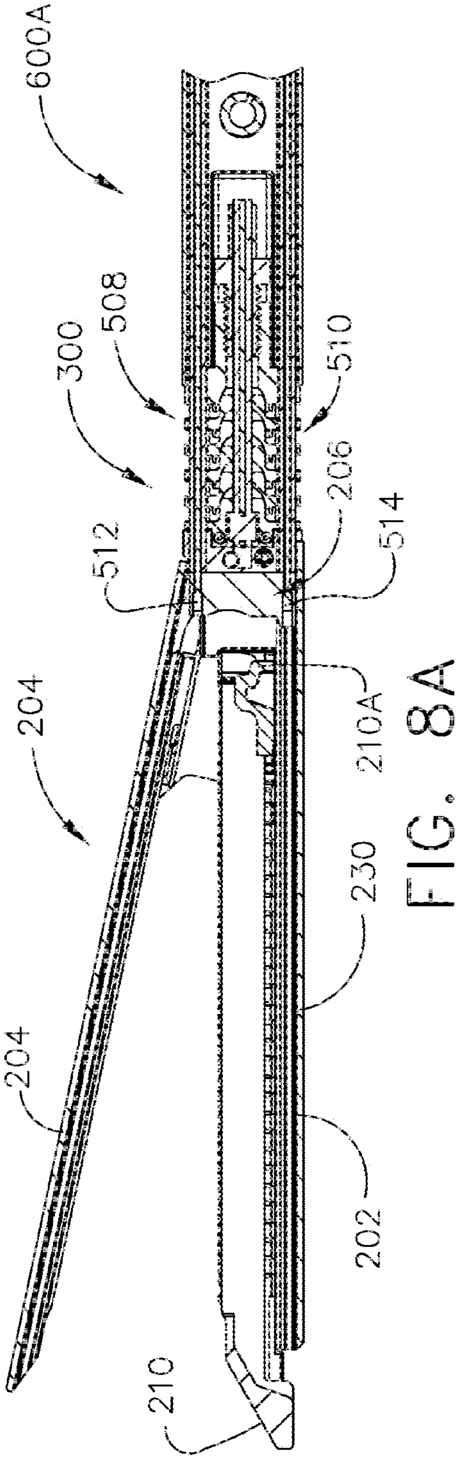
FIG. 8A is a schematic side cross-sectional view of the distal end of the surgical instrument, depicting the anvil in an open position, in accordance with the disclosed technology.

The anvil 204 further defines a longitudinally extending upper knife channel 224 (FIG. 8A, etc.). As shown particularly in FIG. 6, the upper knife channel 224 includes a centrally disposed cylindrical upper knife channel portion 226 and at least one lateral upper knife channel wing 228 that extends away from the upper knife channel portion 226. While the term 'cylindrical' is used, the channel portion 226 need not resemble a perfect cylinder.

II. 1. End Effector and Firing Subsystem

Figure 17:
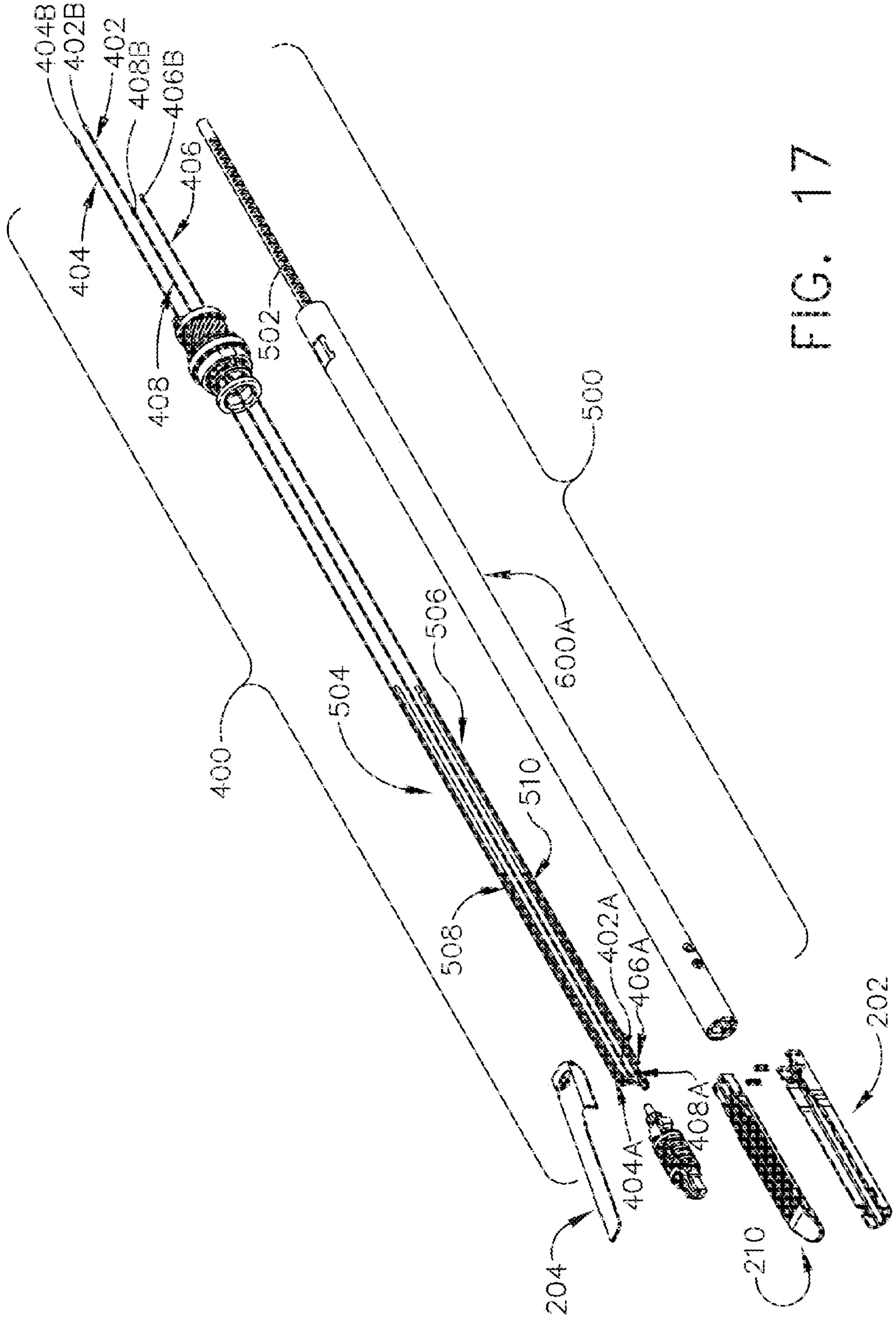
FIG. 17 is a schematic exploded view of the surgical instrument, depicting portions of the cable articulation subsystem, knife firing subsystem, and roll subsystem, in accordance with the disclosed technology.
Figure 18:
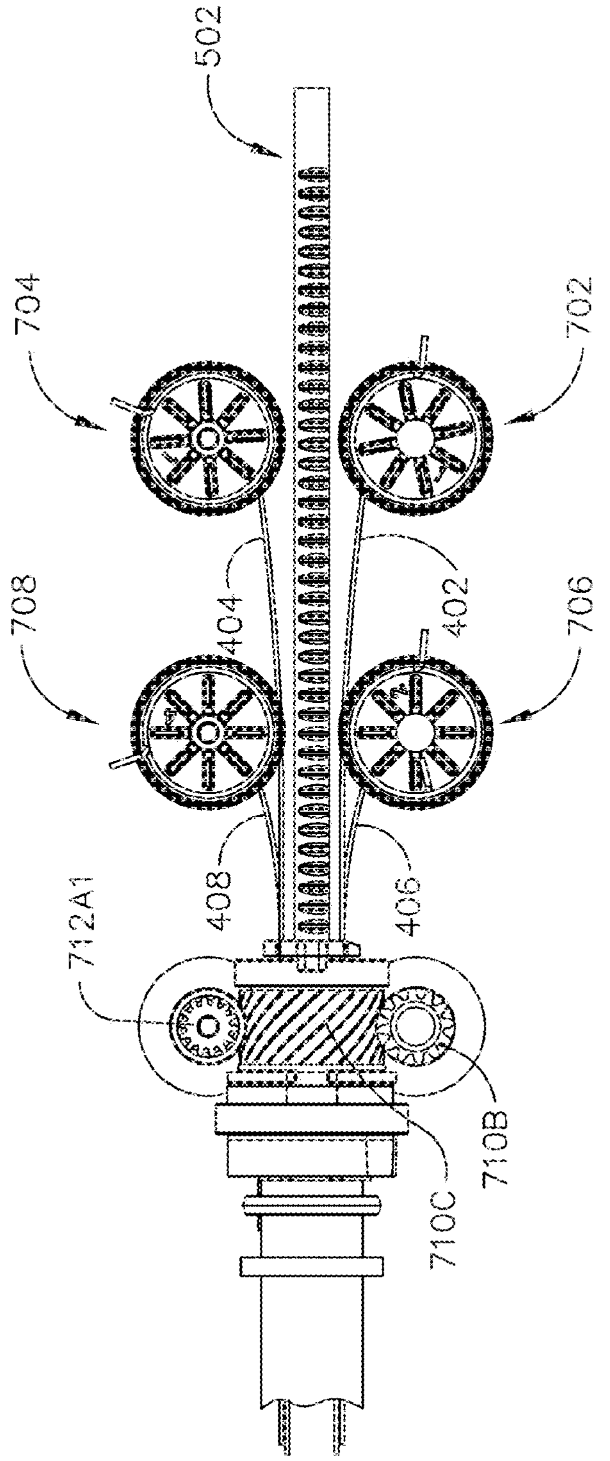
FIG. 18 is a schematic top view of a proximal end of the surgical instrument, depicting portions of the cable articulation subsystem, knife firing subsystem, and roll subsystem, in accordance with the disclosed technology.

The surgical instrument 1000 further comprises a knife firing subsystem 500 operable to close the anvil 204 during a closure stroke. After the end effector 200 is closed, the knife firing subsystem 500 (FIGS. 2 and 17) is operable to incise and staple, with staples from the staple cartridge 210, the patient tissue captured between the staple cartridge 210 (which is retained by the jaw 202) and anvil 204 during a firing stroke.

The knife firing subsystem 500, explained further below in greater detail, includes a knife 206. The knife 206 is coupled to or integral with a knife sled 236. The knife sled 236 is the non-cutting element of the knife 206, and is also referred to as an I-beam. The knife sled 236 includes an upper knife tab 238 and a lower knife tab 246. The upper knife tab 238 includes a centrally disposed cylindrical upper knife tab portion 240 and at least one upper knife tab lateral wing 242 that extends away from the upper knife tab portion 240. While the term 'cylindrical' is used, the tab portion need not resemble a perfect cylinder. In some embodiments, the upper knife tab 238 includes a pair of lateral wings 242 configured to slidably ride in the upper knife channel 224 to move the anvil 204 between the open position, the grasping position, and the clamping position. Each lateral wing 242 may include a ramped surface 242A that engages the anvil ramp surface 216. The upper knife tab portion 240 defines an upper knife tab opening 244 that is configured to receive a barrel crimp coupled to a center cable 512, which is described in greater detail below. The lower knife tab 246 includes a centrally disposed cylindrical lower knife tab portion 248 and at least one lower knife tab lateral wing 250 that extends away from the lower knife tab portion 248. While the term 'cylindrical' is used, the lower knife tab portion 248 need not resemble a perfect cylinder. In some embodiments, the lower knife tab 246 includes a pair of lateral wings 250. The lower knife tab portion 248 defines a lower knife tab opening 252 that is configured to receive a barrel crimp coupled to a center cable 514, which is described in greater detail below, The staple cartridge 210 comprises a cartridge body. In use, the staple cartridge is positioned on a first side of the tissue to be stapled, within the channel 208 of the jaw 202, and the anvil 204 is positioned on a second side of the tissue. The anvil 204 is moved toward the staple cartridge 210 to compress and clamp the tissue against the deck of the staple cartridge 210. Thereafter, staples removably stored in the cartridge body can be deployed into the tissue. The cartridge body includes staple cavities defined therein wherein staples are removably stored in the staple cavities. In some embodiments, the staple cavities are arranged in six longitudinal rows. In some embodiments, three rows of staple cavities are positioned on a first side of a lower knife channel 230 and three rows of staple cavities are positioned on a second side of lower knife channel 230.

Figure 6:
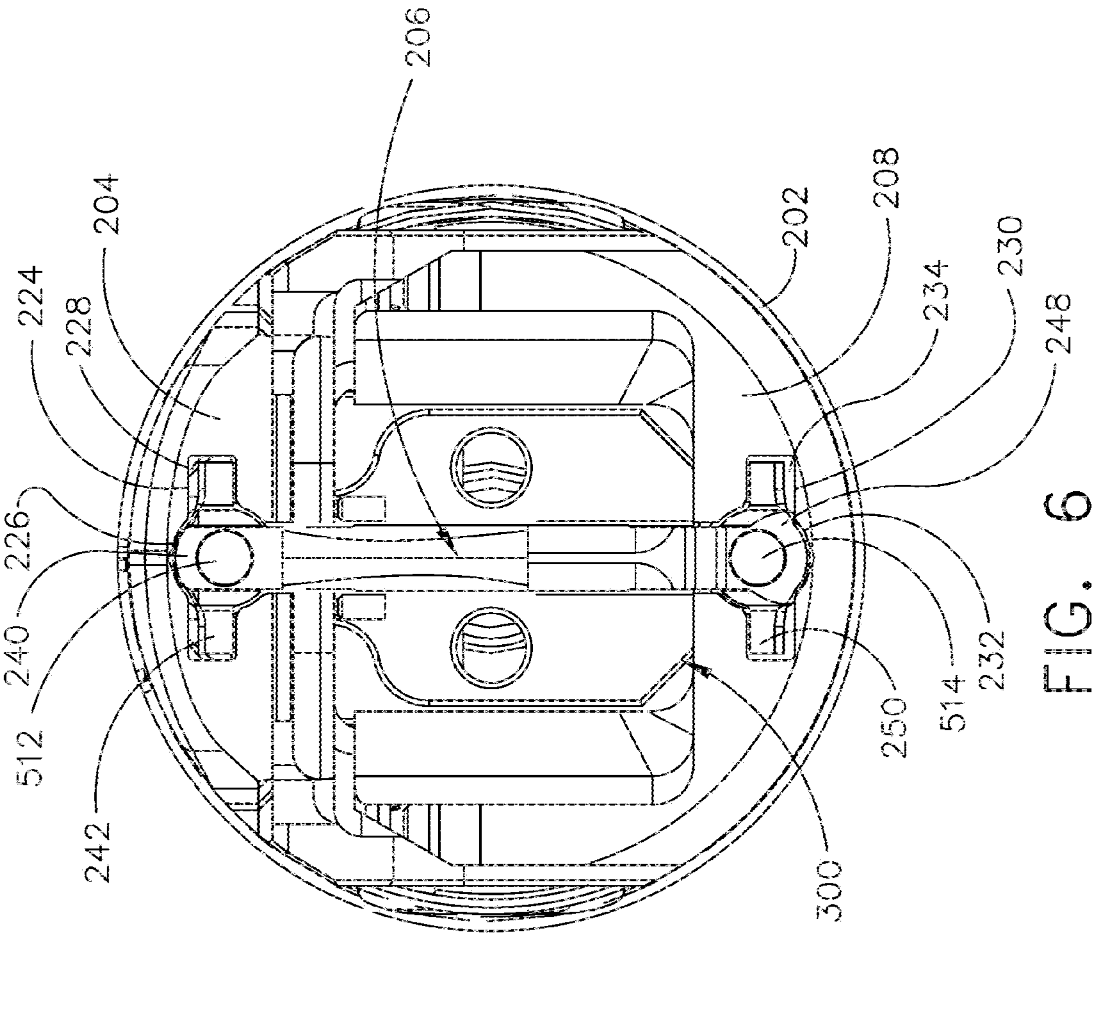
FIG. 6 is a schematic detail front view of the end effector, in accordance with the disclosed technology.

Making particular reference to FIG. 6, the lower knife channel 230 includes a centrally disposed cylindrical lower knife channel portion 232 and at least one lateral lower knife channel wing 234 that extends away from the lower knife channel portion 232. While the term 'cylindrical' is used, the channel portion 232 need not resemble a perfect cylinder. Other arrangements of staple cavities and staples may be possible. For example, in some embodiments, a lower knife channel 230 can be defined in the jaw 202.

Figure 8B:
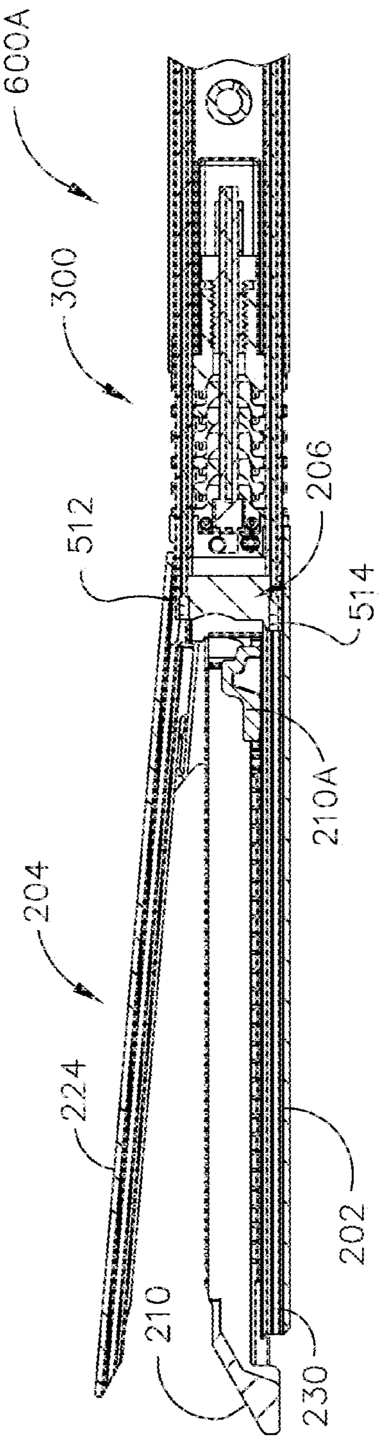
FIG. 8B is a schematic side cross-sectional view of the distal end of the surgical instrument, depicting the anvil in a grasping position with the knife partially advanced, in accordance with the disclosed technology.
Figure 8C:
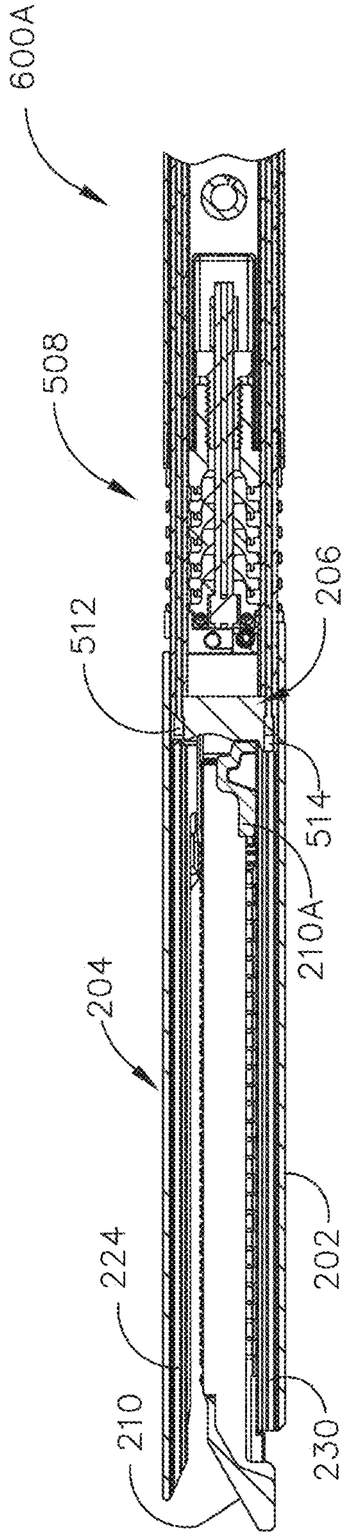
FIG. 8C is a schematic side cross-sectional view of the distal end of the surgical instrument, depicting the anvil in a clamping position with the knife partially advanced, in accordance with the disclosed technology.
Figure 8D:
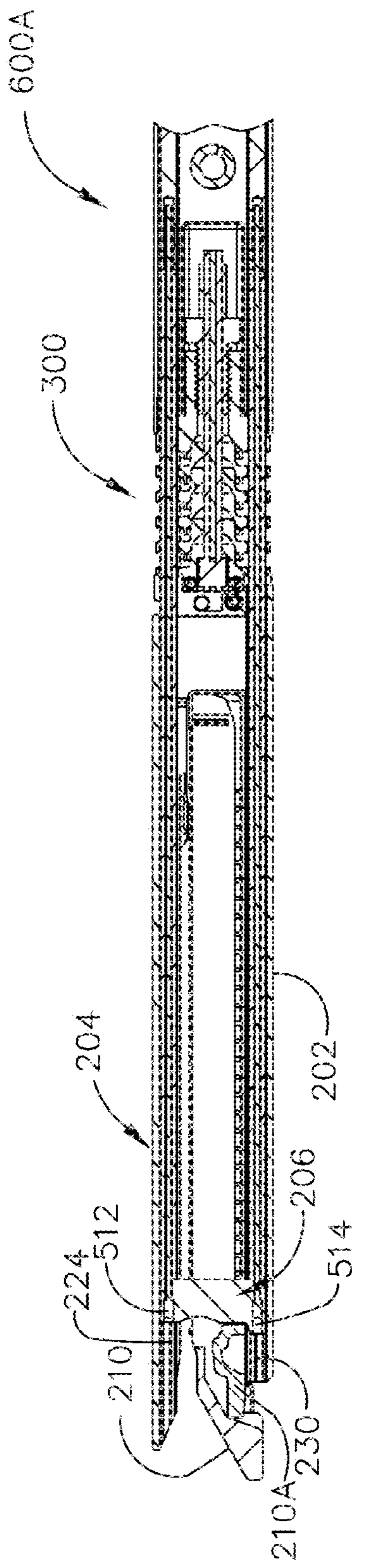
FIG. 8D is a schematic side cross-sectional view of the distal end of the surgical instrument, depicting the anvil in the clamping position with the knife fully advanced, in accordance with the disclosed technology.
Figure 9B:
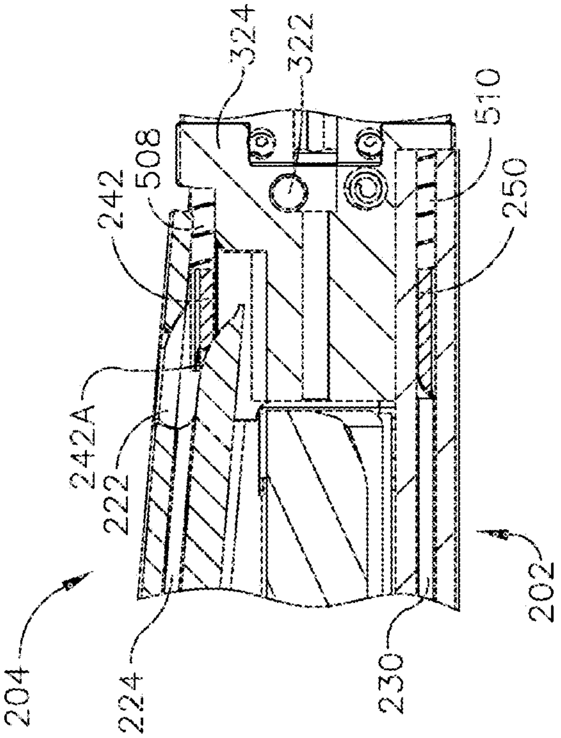
FIG. 9B is a schematic side cross-sectional detail view of the distal end of the surgical instrument, depicting the anvil in a grasping position with the knife partially advanced, in accordance with the disclosed technology.
Figure 9A:
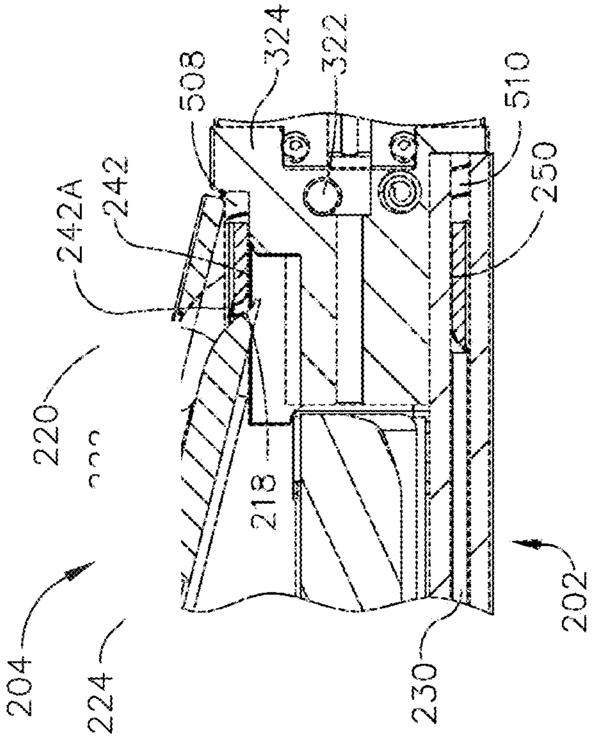
FIG. 9A is a schematic side cross-sectional detail view of the distal end of the surgical instrument, depicting the anvil in the open position, in accordance with the disclosed technology.
Figure 9D:
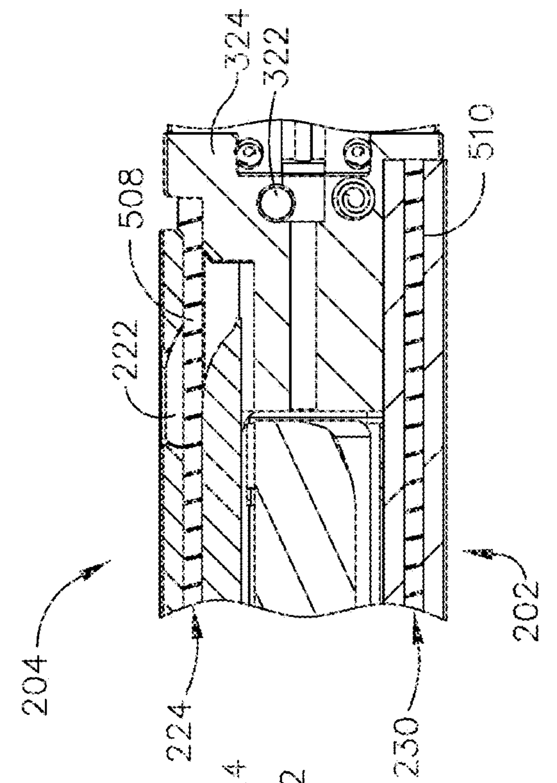
FIG. 9D is a schematic side cross-sectional view of the distal end of the surgical instrument, depicting the anvil in the clamping position with the knife fully advanced, in accordance with the disclosed technology.
Figure 9C:
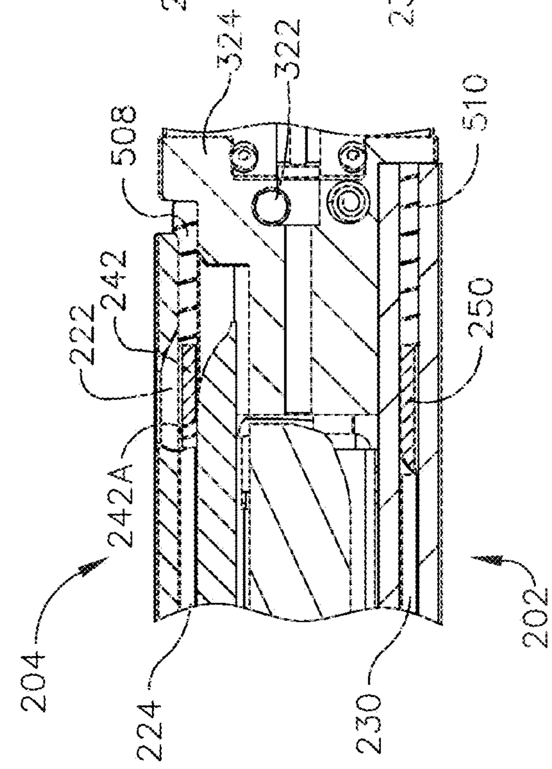
FIG. 9C is a schematic side cross-sectional detail view of the distal end of the surgical instrument, depicting the anvil in a clamping position with the knife partially advanced, in accordance with the disclosed technology.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions indirectly by the sled 236. More specifically, the knife sled 236 is movable between a proximal position adjacent the proximal end and a distal position adjacent the distal end. A portion of the knife sled 236 (e.g., see FIGS. 8C-8D) engages a cartridge sled 210A that slides under the drivers and lifts the drivers, and the staples supported thereon, toward the anvil 204. It is desirable for the knife 206 to be positioned at least partially proximal to the ramped surfaces such that the staples are in the second, or fired, position (i.e., ejected) ahead of the knife 206.

Further to the above, the sled 236 is moved distally and proximally by a firing rod 502. The firing rod 502 is configured to apply an indirect force to the sled 236, via push coils 508, 510 that directly engage the sled 236 (discussed in greater detail below) and push the sled 236 toward the distal end of the end effector 200. As the firing rod 502 is advanced distally, sled 236 rides in the lower knife channel 230 and the upper knife channel 224. At the onset of travel, the upper knife tab 238 rides along the anvil ramp surface 216. Specifically, as particularly seen in the sequence of FIGS. 8A-8D and 9A-9D, movement of the sled 236 distally causes the upper knife tab ramped surface 242A to slide along the anvil ramp surface 216. This movement first urges the anvil 204 closed to a position (e.g., FIGS. 8B and 9B) where a compressive force is applied to the tissue sufficient to grasp it (referred to as the grasping position). Continued movement of the sled 236 up the ramp surface 216 (e.g., see FIGS. 8C and 9C) results in a compressive force being applied to the tissue (referred to as the clamping position). As the anvil ramp surface 216 transitions to its substantially horizontally angled surface 218 (e.g., see FIGS. 8D and 9D), the upper knife tab 238 can slide within the upper knife channel 224 to drive the stapling and transection of the tissue.

III. OVERVIEW OF THE HOUSING AND SHAFT ASSEMBLY

The surgical instrument 1000 further comprises a housing 700 and a shaft assembly 600A extending from the housing 700. The housing is configured to engage a robotic platform 2000. In some embodiments, the housing 700 may be configured as a handle (e.g., it may comprise a grip for a clinician). The shaft assembly 600A comprises a rotatable outer shaft 602 and an inner shaft 604, the outer shaft 602 being rotatably mounted to the housing about a rotation joint 606 (which may include one or more bearings). The inner shaft 604 is rotationally fixed to the outer shaft 602 and is configured such that articulation cables 402, 404, 406, 408, discussed in greater detail below, can be partially wound therearound without becoming tangled. As discussed in greater detail below, the housing 700 further comprises (1) a firing puck assembly 712 as part of the knife firing subsystem 500 operable to close the end effector 200, fire staples, and transect tissue, (2) a set of articulation puck assemblies 702, 704, 706, 708 as part of the articulation subsystem 400 operable to articulate the end effector 200 relative to the shaft assembly 600A, and (3) a shaft roll puck assembly 710 as part of the roll subsystem 600 configured to roll the outer shaft 602.

IV. OVERVIEW OF THE ARTICULATION SUBSYSTEM

IV. 1. Articulation Joint

Figure 10:
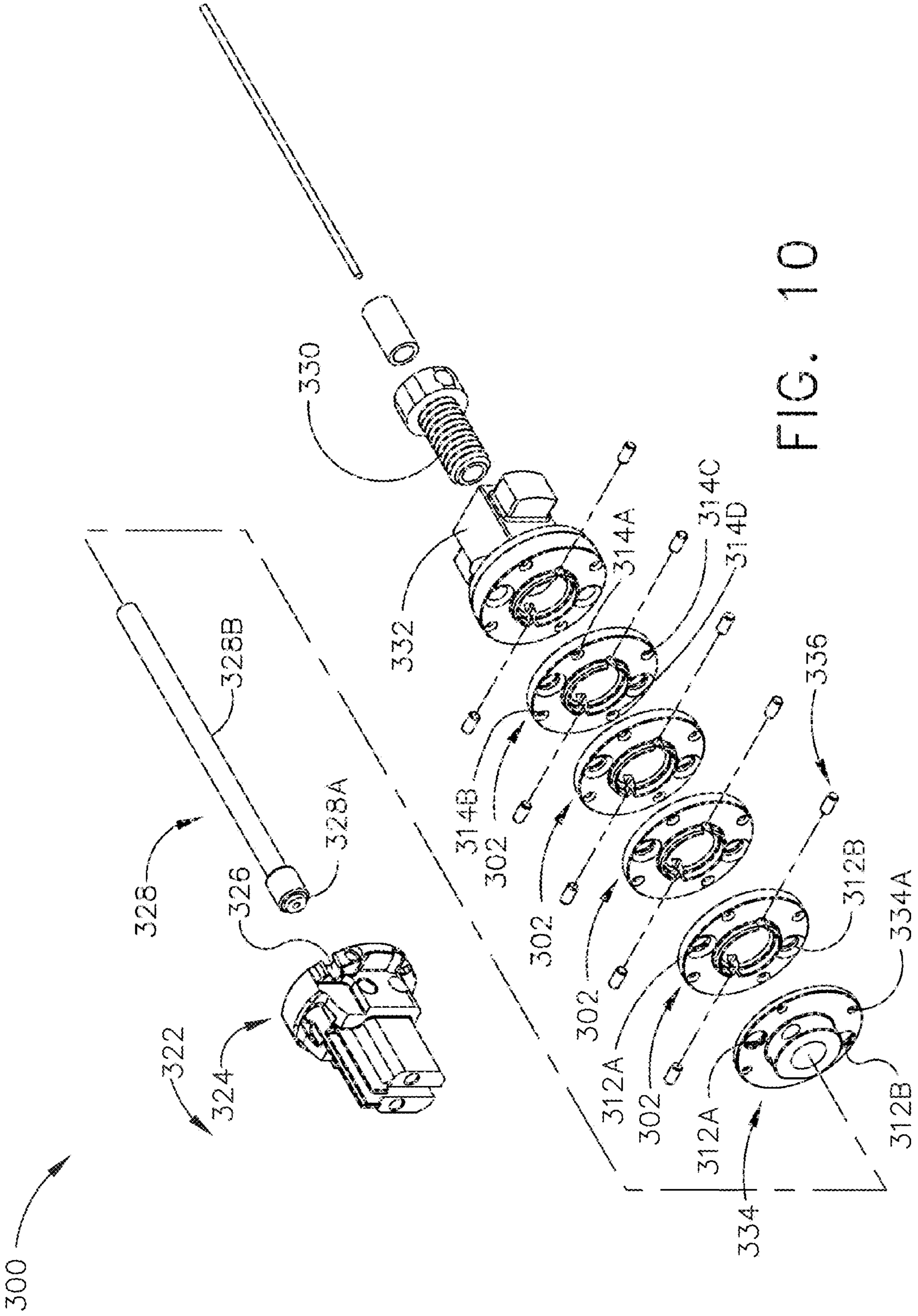
FIG. 10 is a schematic exploded view of the articulation joint, in accordance with the disclosed technology.
Figure 11:
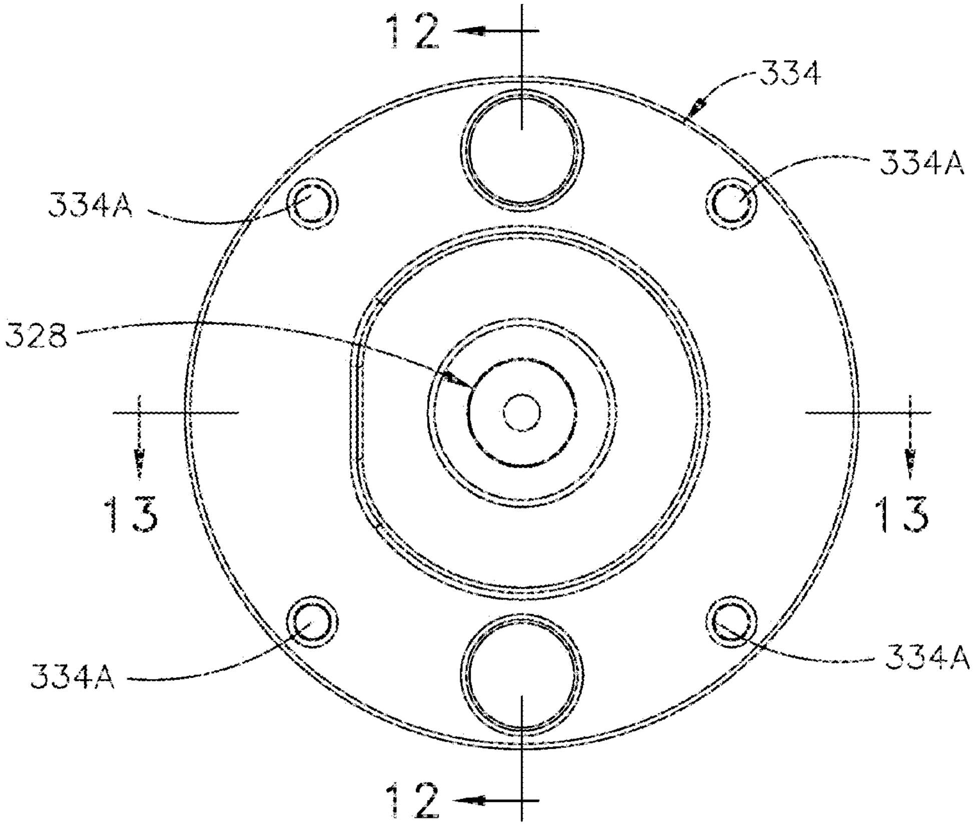
FIG. 11 is a schematic elevation view of the articulation joint, in accordance with the disclosed technology.
Figure 12:
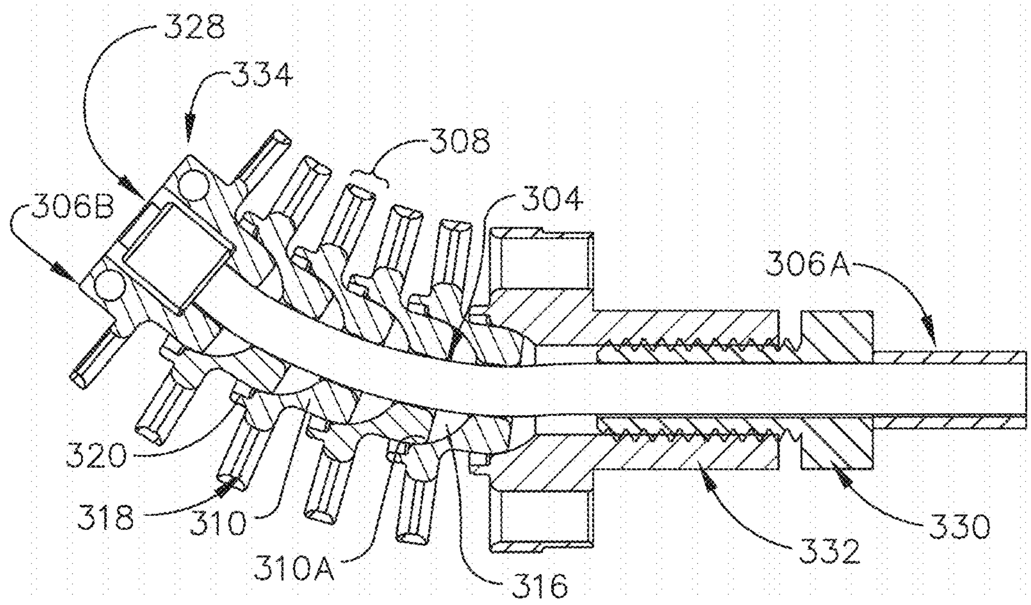
FIG. 12 is a schematic cross-sectional view of the articulation joint, cut relative to line 12-12 in FIG. 11; in accordance with the disclosed technology.
Figure 13:
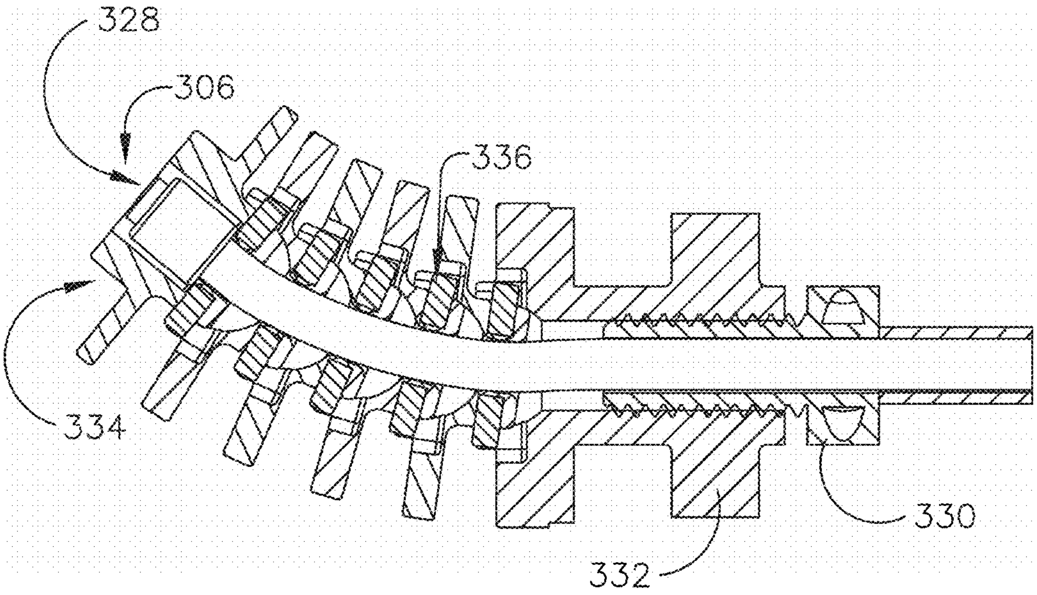
FIG. 13 is a schematic cross-sectional view of the articulation joint, cut relative to line 13-13 in FIG. 11; in accordance with the disclosed technology.
Figure 14:
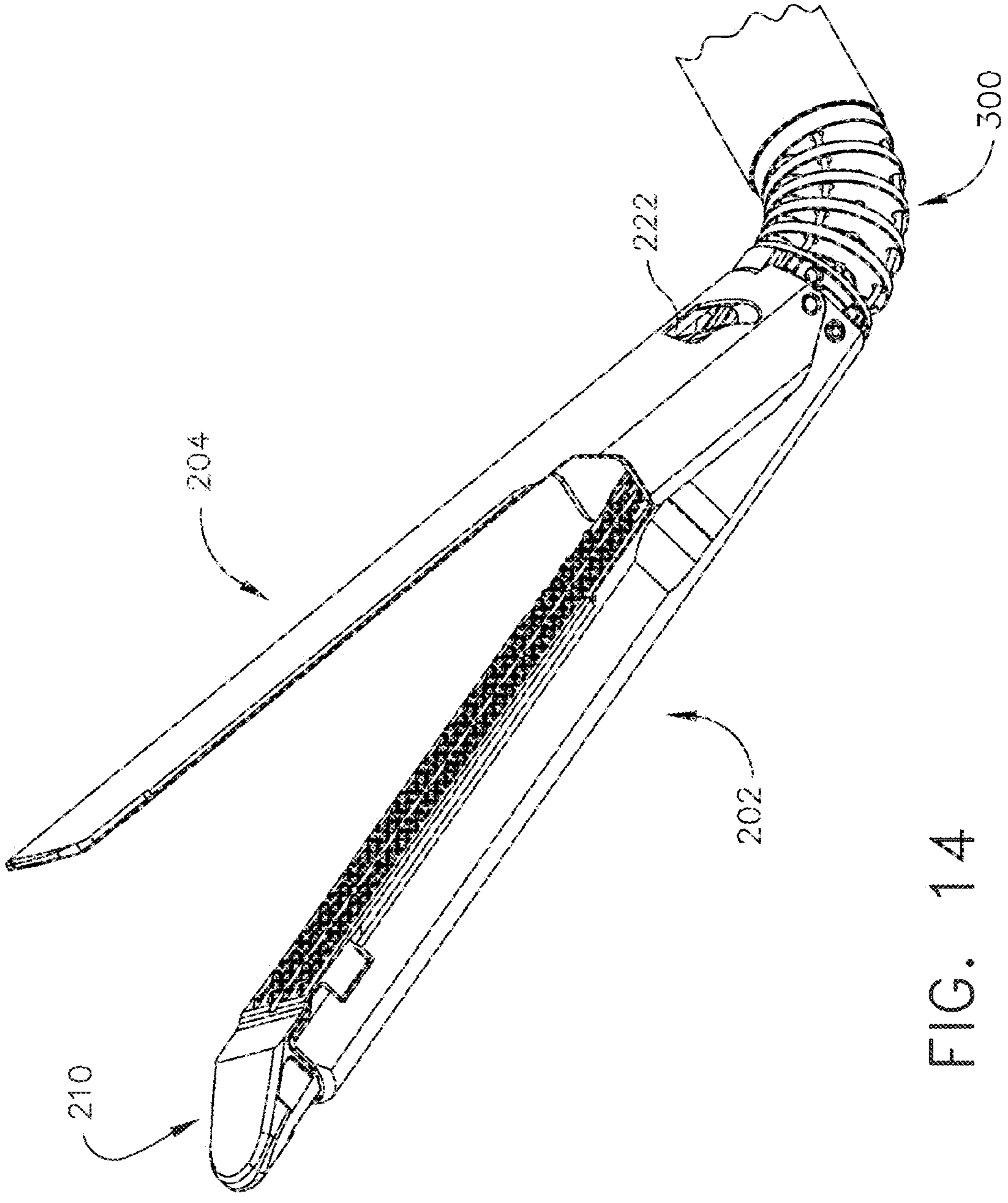
FIG. 14 is a schematic perspective detail view of the distal end of the surgical instrument, depicting the end effector pivoted vertically and laterally with the anvil open, in accordance with the disclosed technology.
Figure 15:
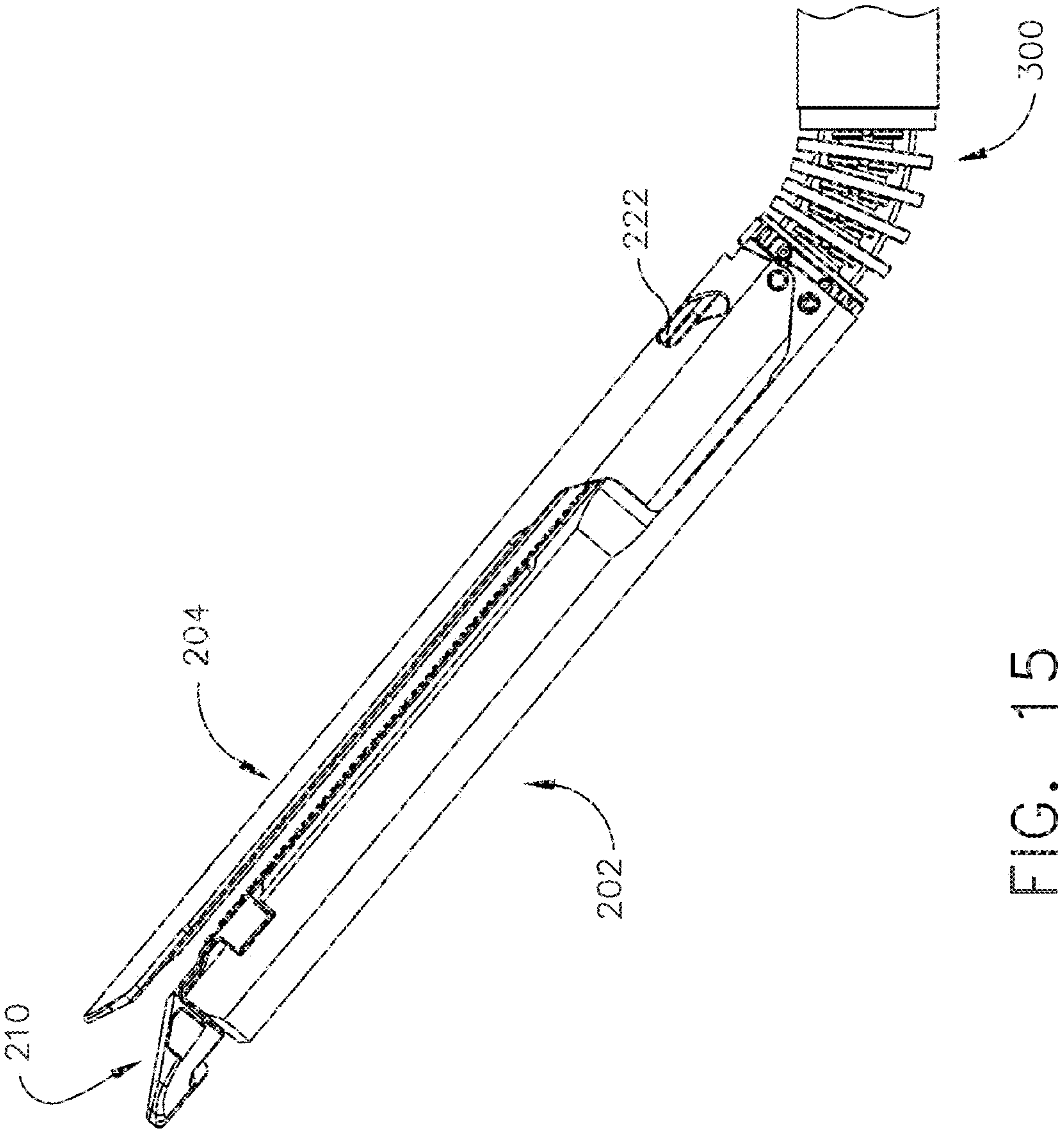
FIG. 15 is a schematic side detail view of the distal end of the surgical instrument, depicting the end effector pivoted vertically with the anvil closed, in accordance with the disclosed technology.
Figure 16:
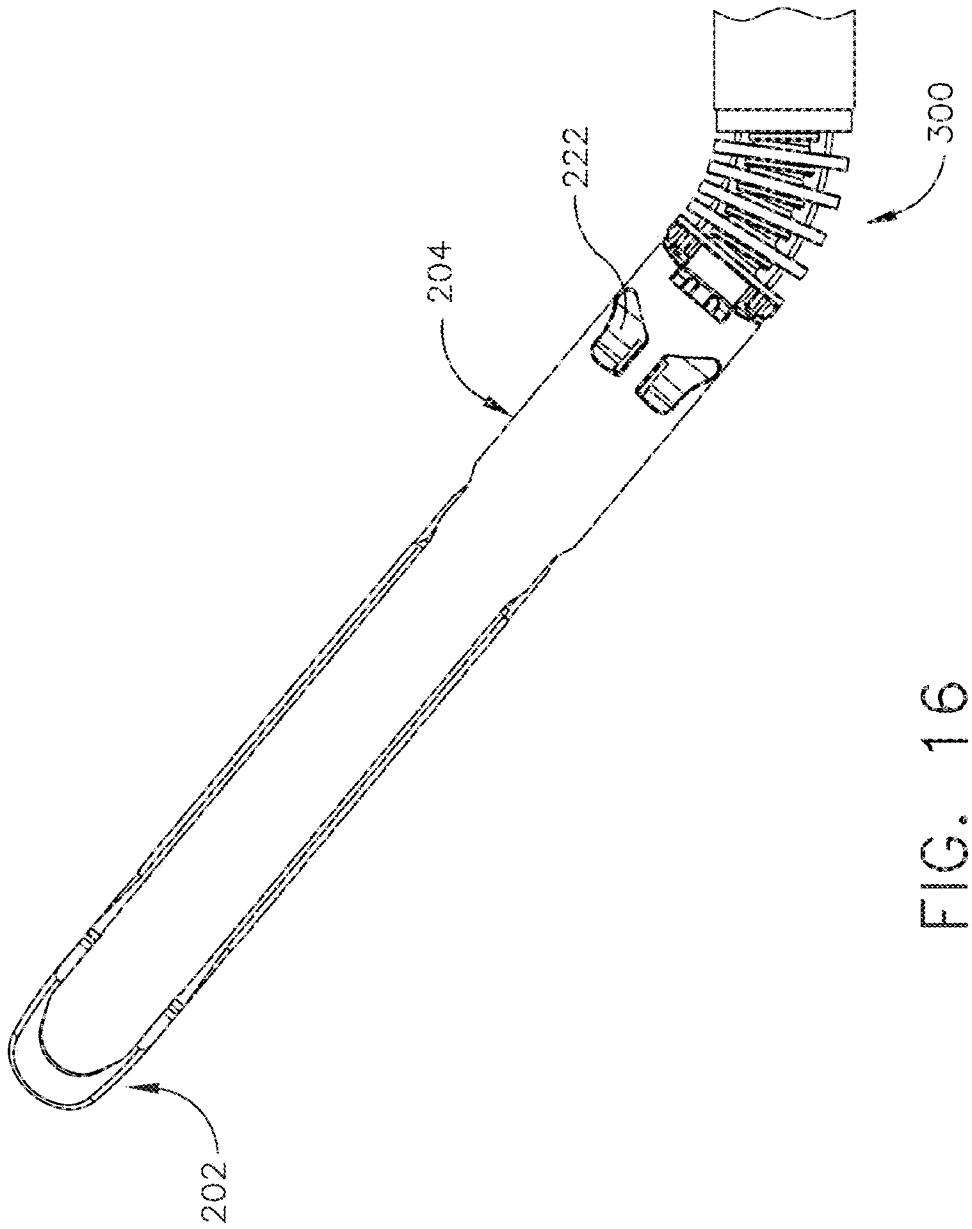
FIG. 16 is a schematic top detail view of the distal end of the surgical instrument, depicting the end effector pivoted laterally with the anvil closed, in accordance with the disclosed technology.

Referring to FIG. 10, the articulation joint 300 comprises a plurality of concentric discs 302 and a center beam assembly 306. Each concentric disc further includes a concentric central opening 304. The center beam assembly 306 has a proximal end 306A and a distal end 306B. As shown in FIGS. 12 and 13, a portion of the center beam assembly 306 extends through the central opening 304 of each concentric disc 302, and the center beam assembly 306 applies a compressive force to the concentric discs 302. The concentric discs 302 are nestably stacked on the center beam assembly 306 such that adjacent concentric discs 302 interface with one another. As seen in FIG. 7, the distal end 306B of the center beam assembly 306 couples to the plurality of concentric discs 302 to a proximal end of the end effector 200 of the surgical instrument 1000 (via one or more fasteners 322). As seen in FIG. 10, the distal end 306B includes a distal end retention disc 334 that defines a plurality of cable retention openings 334A. Further, the proximal end 306A of the center beam assembly 306 includes a second disc retention bearing 332 that is nested within and/or coupled with the shaft assembly 600A so as to couple the concentric discs 302 to the shaft assembly 600A. In some embodiments, the distal end 306B of the center beam assembly 306 abuts the knife sled 236.

As shown particularly in FIGS. 10, 12, and 13, each concentric disc 302 includes an articulation socket 308, an articulation pin 310 protruding outwardly from the articulation socket 308, a first push coil opening 312A defined through the articulation socket 308 and configured to receive a first push coil 508 therethrough, a second push coil opening 312B defined through the articulation socket 308 and configured to receive a second push coil 510 therethrough, and a plurality of articulation cable openings 314A-314D (e.g., a first articulation cable opening 314A, a second articulation cable opening 314B, a third articulation cable opening 314C, and a fourth articulation cable opening 314D) defined through the articulation socket 308 and configured to receive a respective articulation cable 402, 404, 406, 408 (e.g., a first articulation cable 402, a second articulation cable 404, a third articulation cable 406, and a fourth articulation cable 408) therethrough, and discussed in greater detail below. As shown in FIGS. 12 and 13, the concentric disc opening 304 is defined in the articulation pin 310 of each concentric disc 302. In some embodiments, three articulation cable openings 314A, 314B, 314C are provided to correspond to three articulation cables 402, 404, 406, while in other embodiments, four articulation cable openings 314A, 314B, 314C, 314D are provided to correspond to four articulation cables 402, 404, 406, 408.

Each concentric disc 302 further includes a rounded articulation pin proximal end 310A and a semi-spherical pin-receiving opening 316 defined in the articulation socket 308. As shown particularly in FIGS. 12 and 13, each rounded articulation pin proximal end 310A pivotally engages in an adjacent pin-receiving opening 316 of an adjacent concentric disc 302, with the exception of a proximal-most end 310A that engages with a second disc retention bearing 332. The articulation pin proximal end 310A and pin-receiving opening 316 interface functions in a similar manner as a swivel bearing. Moreover, the articulation socket 308 includes a socket disc 318 and a pin retention socket 320. A pair of pins 336 are used to provide rotational coupling about a primary axis of the shaft assembly 600A from one disc 302 to the next. In other words, the pins constrain a rotational degree of freedom between adjacent concentric discs 302) about the roll axis RA of the instrument 1000. In alternative embodiments, this feature can be integral to the disc 302 as opposed to the separate pins 336 shown in, e.g., FIG. 10.

Making particular reference to FIG. 10, the distal end 306B of the center beam assembly 306 includes a first disc retention bearing 324 that defines a plurality of clearance pockets 326. The center beam assembly 306 also further includes a center beam 328 extending through each of the concentric discs 302, a jack screw 330, and a second disc retention bearing 332. The jack screw 330 is threadably coupled with the second disc retention bearing 332 to adjust a compressive force of the center beam 328 (i.e., it can be used to adjust pre-tension of the articulation joint 300). The center beam assembly 326 keeps the discs 302 together and also reacts the firing load so that it does not react on the articulation cables (which are discussed in greater detail below).

The center beam 328 further includes a nitinol core 328A and stainless steel 328B wound over the nitinol core that allows the center beam 328 to resiliently flex in response to pivoting of one, some, or all of the concentric discs 302. The wound stainless steel 328B has clockwise braiding and counterclockwise braiding to prevent unwinding thereof.

The above-described articulation joint 300 forms a portion of the cable articulation subsystem 400 which allows for precise 360-degree movement of the end effector 200 about the articulation joint 300 with at least two degrees of freedom. In some embodiments, and dictated by the roll subsystem 600 as well as a need to limit the amount of wrap of the articulation cables 402, 404, 406, 408, the articulation joint is permitted about 320 degrees of roll within the overall system. The cable articulation subsystem 400 also includes a plurality of articulation cables 402, 404, 406, 408 each having a distal end 402A, 404A, 406A, 408A, coupled to the distal end 306B of the center beam assembly 306, and a proximal end 402B, 404B, 406B, 408B. More specifically, each distal end 402A, 404A, 406A, 408A can include a crimp that engages a cable retention opening 334A of the distal end retention disc 334 to maintain its positioning.

IV. 2. Articulation Cables

Each articulation cable 402, 404, 406, 408 includes a stainless steel material with clockwise braiding and counterclockwise braiding that prevent unwinding thereof. In other embodiments, other materials may be employed, such as polymer yarns and/or filaments, various metal cables (e.g., tungsten), and combinations thereof. Each articulation cable is discretely manipulable to cause rotation of the articulation joint 300 and end effector 200 about at least one of a pitch axis PA and a yaw axis YA.

In some embodiments, three articulation cables may be provided rather than the four cables 402, 404, 406, 408 depicted herein. However, four articulation cables 402, 404, 406, 408 circumferentially spaced approximately ninety degrees from one another (as shown) provides load splitting. Additionally, in alternative embodiments, three and fourth articulation cable configurations may be spaced non-symmetrically relative to one another.

Figure 35:
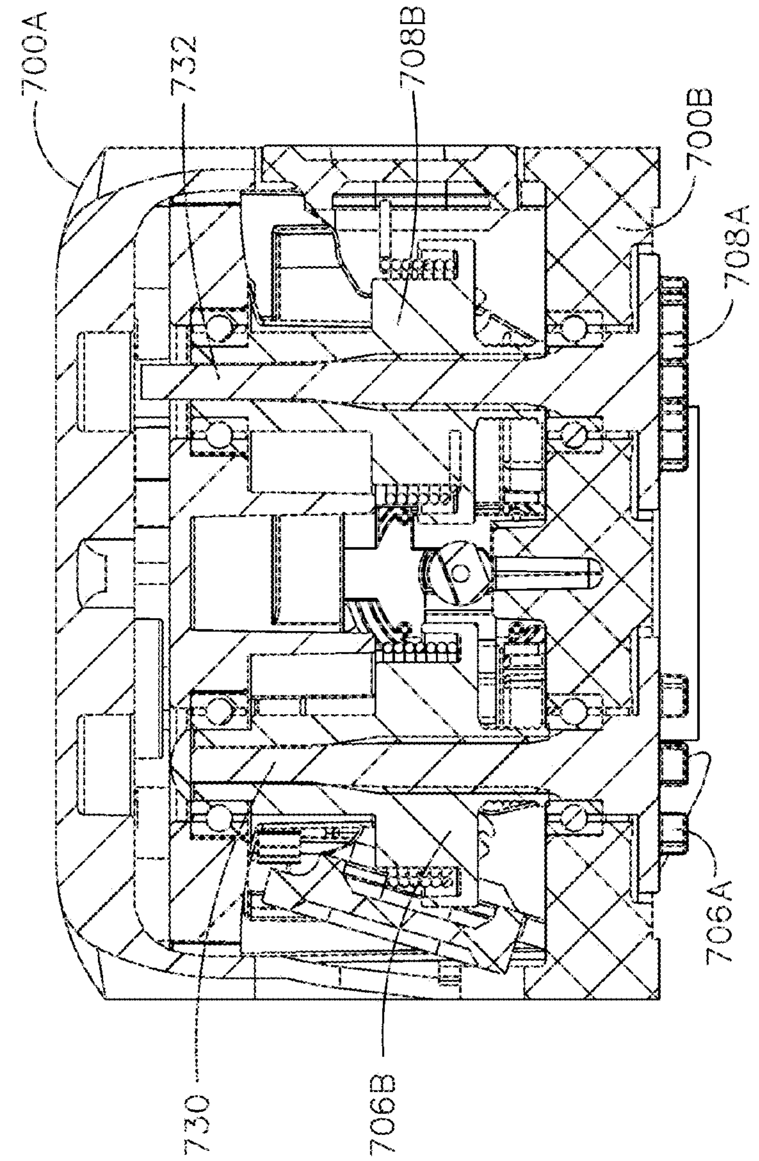
FIG. 35 is a schematic cross-sectional view of the housing, cut relative to line 35-35 in FIG. 32; in accordance with the disclosed technology.
Figure 36:
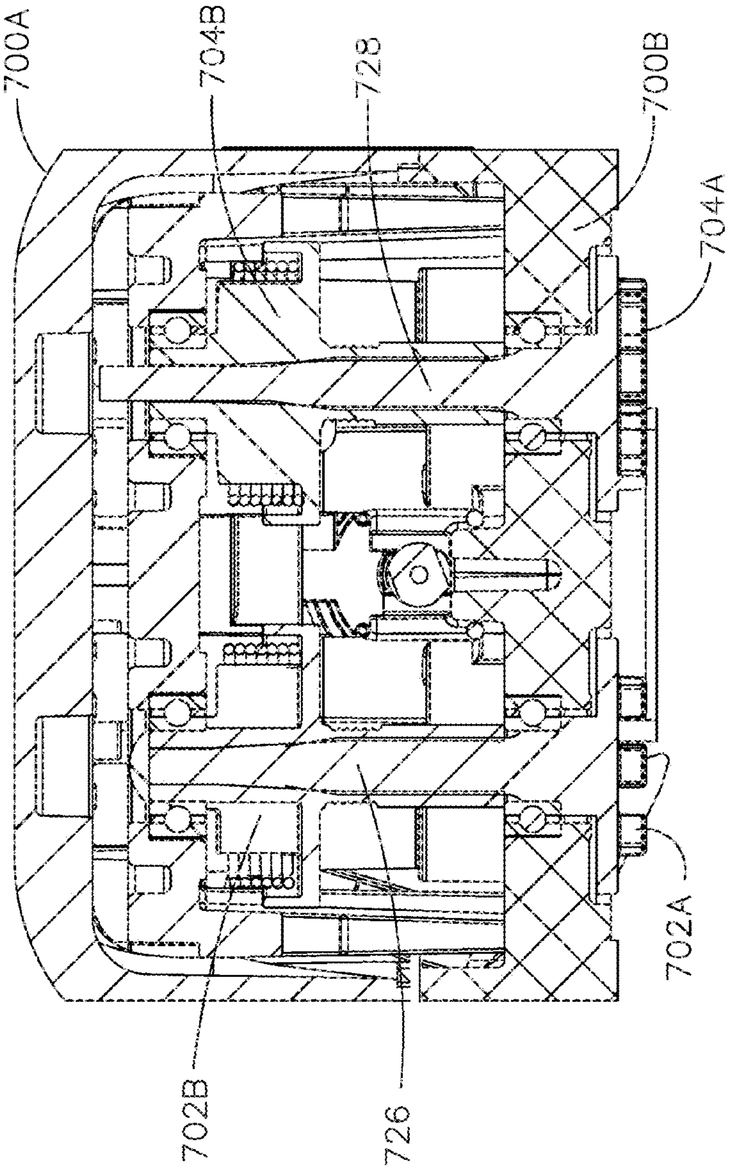
FIG. 36 is a schematic cross-sectional view of the housing, cut relative to line 36-36 in FIG. 32; in accordance with the disclosed technology.

The shaft assembly 600A and housing 700 also form portions of the cable articulation subsystem 400. More specifically, each articulation cable 402, 404, 406, 408 extends from the articulation joint 300 and through the shaft assembly 600A to the housing 700. The proximal end 402B, 404B, 406B, 408B of each articulation cable (402, 404, 406) is movably mounted in the housing 700 which causes the above-mentioned rotation of the articulation joint 300 and end effector 200. In some embodiments, the housing 700 includes articulation puck assemblies 702, 704, 706, 708 with rotatable capstans 702B, 704B, 706B, 708B, discussed in greater detail below, about which corresponding proximal ends 402B, 404B, 406B, 408B of the articulation cables 402, 404, 406, 408 are windably mounted thereto. As shown in FIGS. 35 and 36, the capstans 702B, 704B, 706B, 708B can be vertically offset from one another (e.g., capstan 702B and capstan 704B can be located proximal one portion 700A of the housing 700, and capstan 706B and capstan 708B can be located proximal another portion 700B of the housing 700.

The articulation cables 402, 404, 406, 408 are routed through the shaft assembly 600A such that they are disposed between the outer shaft 602 and the inner shaft 604, with the articulation cables 402, 404, 406, 408 being able to partially wind therearound without becoming tangled. The inner shaft 604 also prevents the articulation cables 402, 404, 406, 408 from interfering with other components running down the center of the instrument 1000 (through the inner shaft 604).

IV. 3. Articulation Joint and Articulation Cable Connection/Operation

The articulation cables 402, 404, 406, 408 are routed and coupled to the end effector 200 via the articulation joint 300 such that movement thereof in a proximal direction (via winding about the capstans 702B, 704B, 706B, 708B) causes the end effector 200 to pivot in a predetermined manner about the articulation joint 300. For example, actuation of the first articulation cable 402 in the proximal direction causes rotation of the end effector 200 upwards and to the left, actuation of the second articulation cable 404 in the proximal direction causes rotation of the end effector 200 upwards and to the right, actuation of the third articulation cable 406 in the proximal direction causes rotation of the end effector 200 downwards and to the left, and actuation of the fourth articulation cable 408 in the proximal direction causes rotation of the end effector 200 downwards and to the right. Similarly, movement of two articulation cables simultaneously will result in blended movement of the end effector 200. By way of example, movement of both the first articulation cable 402 and the second articulation cable 404 at the same rate causes only upwards pivoting of the end effector 200 (i.e., there is little to no horizontal component to the rotation). As will be appreciated by those skilled in the art, this configuration provides for the above-mentioned precise 360-degree movement of the end effector about the articulation joint 300 with at least two degrees of freedom and about 320 degrees of roll.

V. OVERVIEW OF THE FIRING SUBSYSTEM

Referring primarily to FIGS. 2, 8A-8D, 9A-9D, 17 and 23, the knife firing subsystem 500 includes the aforementioned knife 206, the aforementioned sled 236, a firing rod 502 that drives the knife 206 and/or sled 236, a first push rod 504, and a second push rod 506. The firing rod 502 includes a firing rod rack 530 and is driven by a firing puck assembly 712, which is described in greater detail below. The first push rod 504 has a first push rod distal end 504A coupled to the sled 236 and a first push rod proximal end 504B coupled to the firing rod 502. Similarly, the second push rod has a second push rod distal end 506A coupled to the sled 236 and a second push rod proximal end 506B coupled to the firing rod 502. The distal ends 504A, 506A are coupled to respective upper and lower portions of the sled 236 (e.g., the upper knife tab 238 and the lower knife tab 246), which enables the knife 206 to be pushed evenly at its ends. In some embodiments, the proximal ends 504B, 506B of the push rods 504, 506 are coupled to the firing rod via a differential 520, which is discussed in greater detail below.

The knife firing subsystem 500 is configured in a manner to enable articulation of the end effector 200 while still enabling proper functionality of the knife 206. To that end, the first push rod 504 includes a first flexible section 508 and the second push rod 506 comprises a second flexible section 510. As particularly shown in FIGS. 20-22, the flexible sections 508, 510 rout through the articulation joint 300 via the respective push coil openings 312A, 312B and the push rods 504, 506 engage the respective tab openings 244, 252 in the sled 236. More specifically, the first flexible section 508 includes a first push coil 508 and a first center cable 512 extends through the first push coil 508 to engage the sled 236 via a barrel crimp, and the second flexible section 510 includes a second push coil 510 and a second center cable 514 extends through the second push coil 510 to engage the sled 236 via a barrel crimp. The push coils 508, 510 provide the rods 504, 506 sufficient stability to deliver a firing force to the knife 206, while not being too stiff that would prevent articulation at the joint 300. The cables 512, 514, which are engaged with the sled 236 as discussed above (see, e.g., FIG. 8A), prevent the coils 508, 510 from stretching and/or elongating and serve as retraction cables when the rods 504, 506 are retracted towards the proximal end of the surgical instrument 1000.

Figure 20:
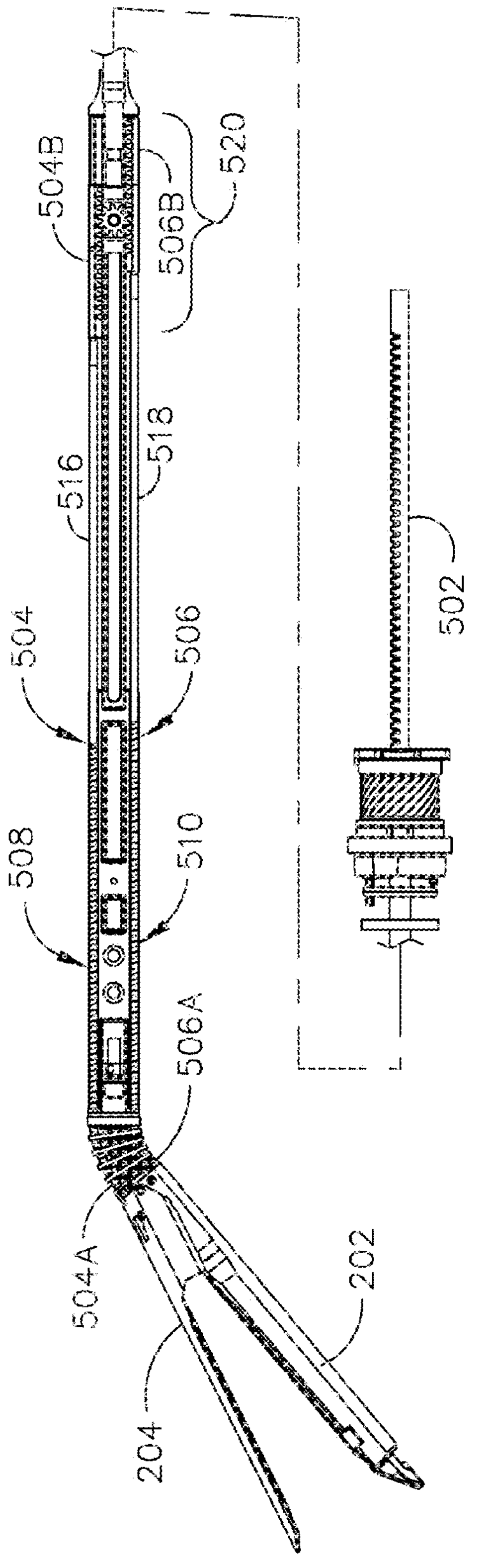
FIG. 20 is a schematic side view of the firing subsystem, depicting the end effector pivoted vertically downwards and the anvil in the open position, in accordance with the disclosed technology.
Figure 21:
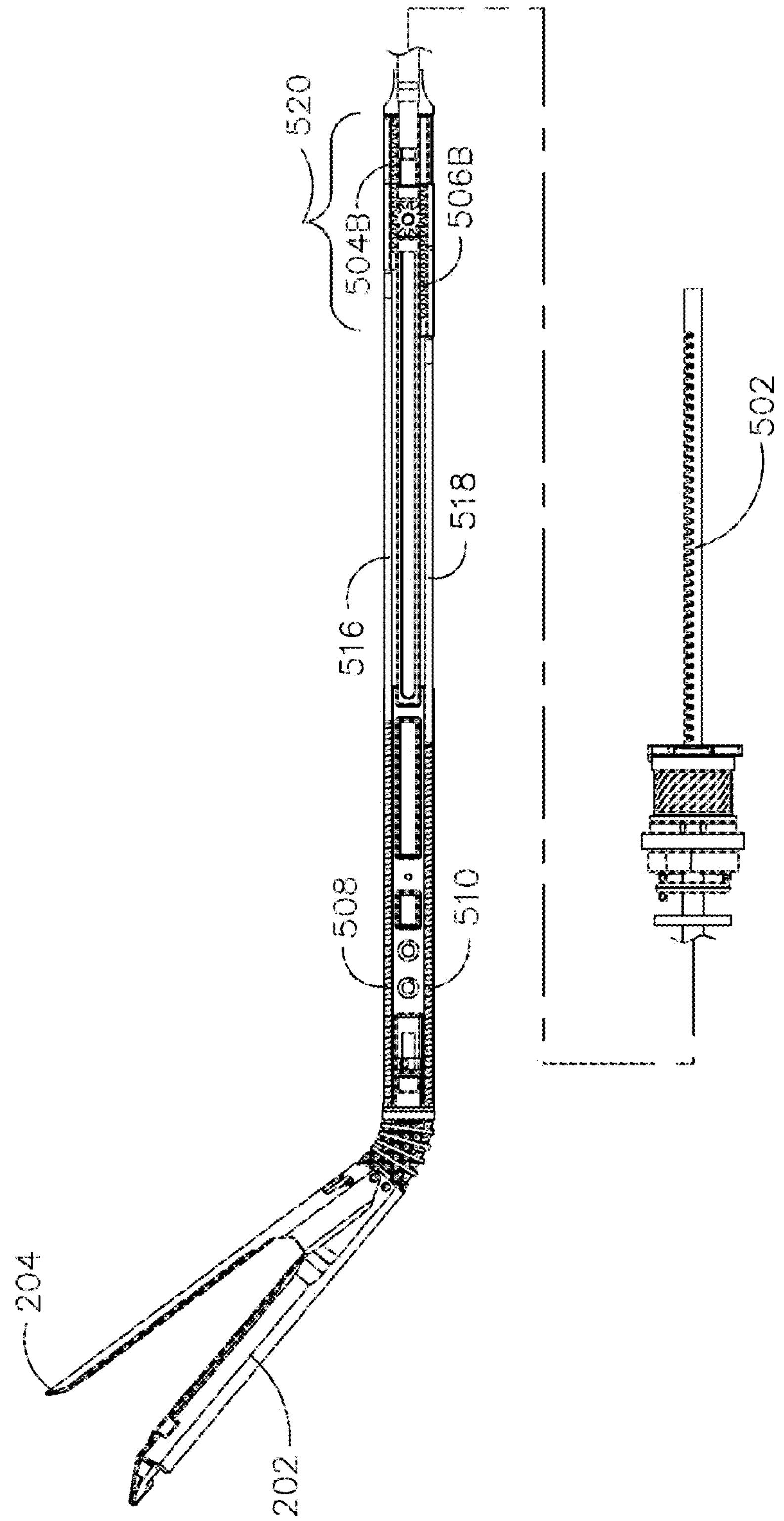
FIG. 21 is a schematic side view of the firing subsystem, depicting the end effector pivoted vertically upwards and the anvil in the open position, in accordance with the disclosed technology.
Figure 22:
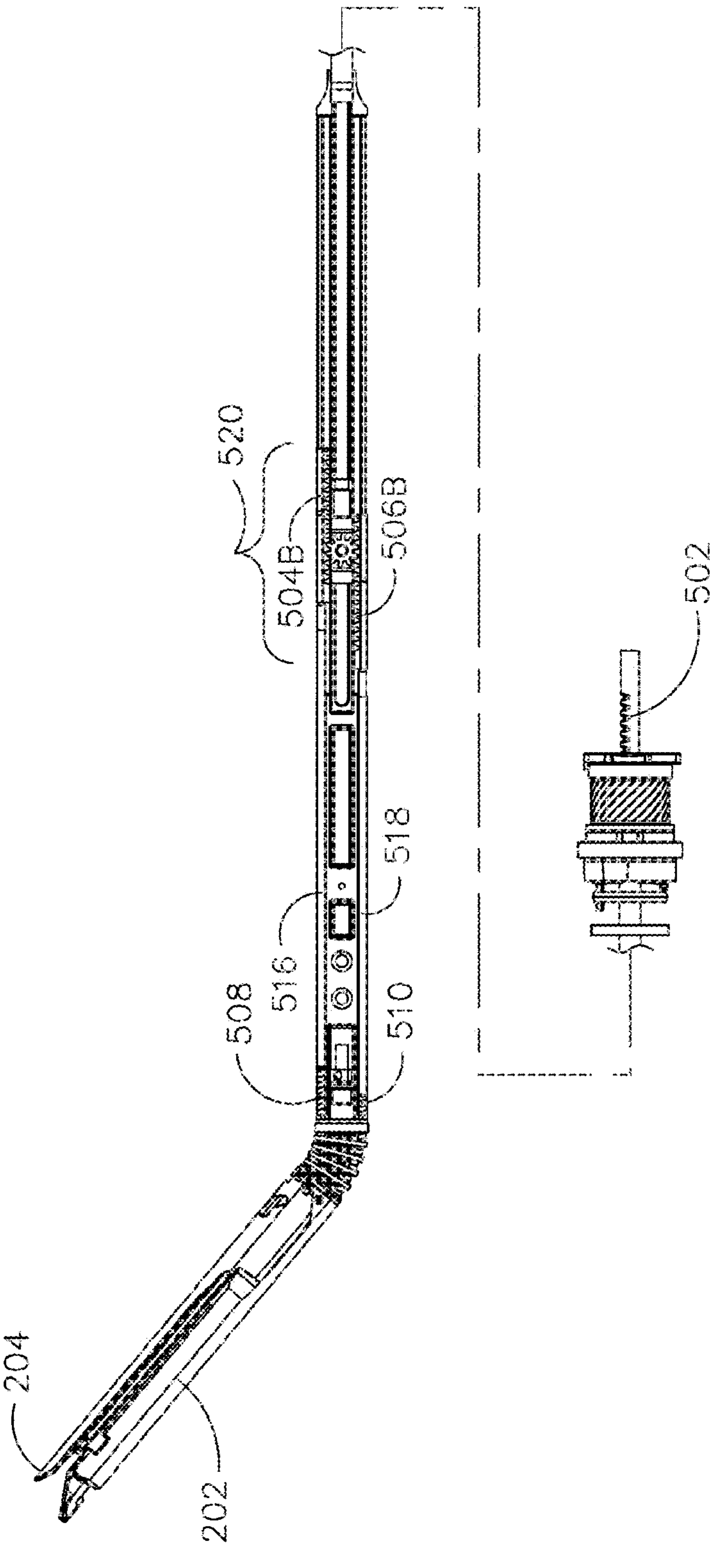
FIG. 22 is a schematic side view of the firing subsystem, depicting the end effector pivoted vertically upwards and the anvil in the clamping position and the knife fully advanced, in accordance with the disclosed technology.
Figure 23:
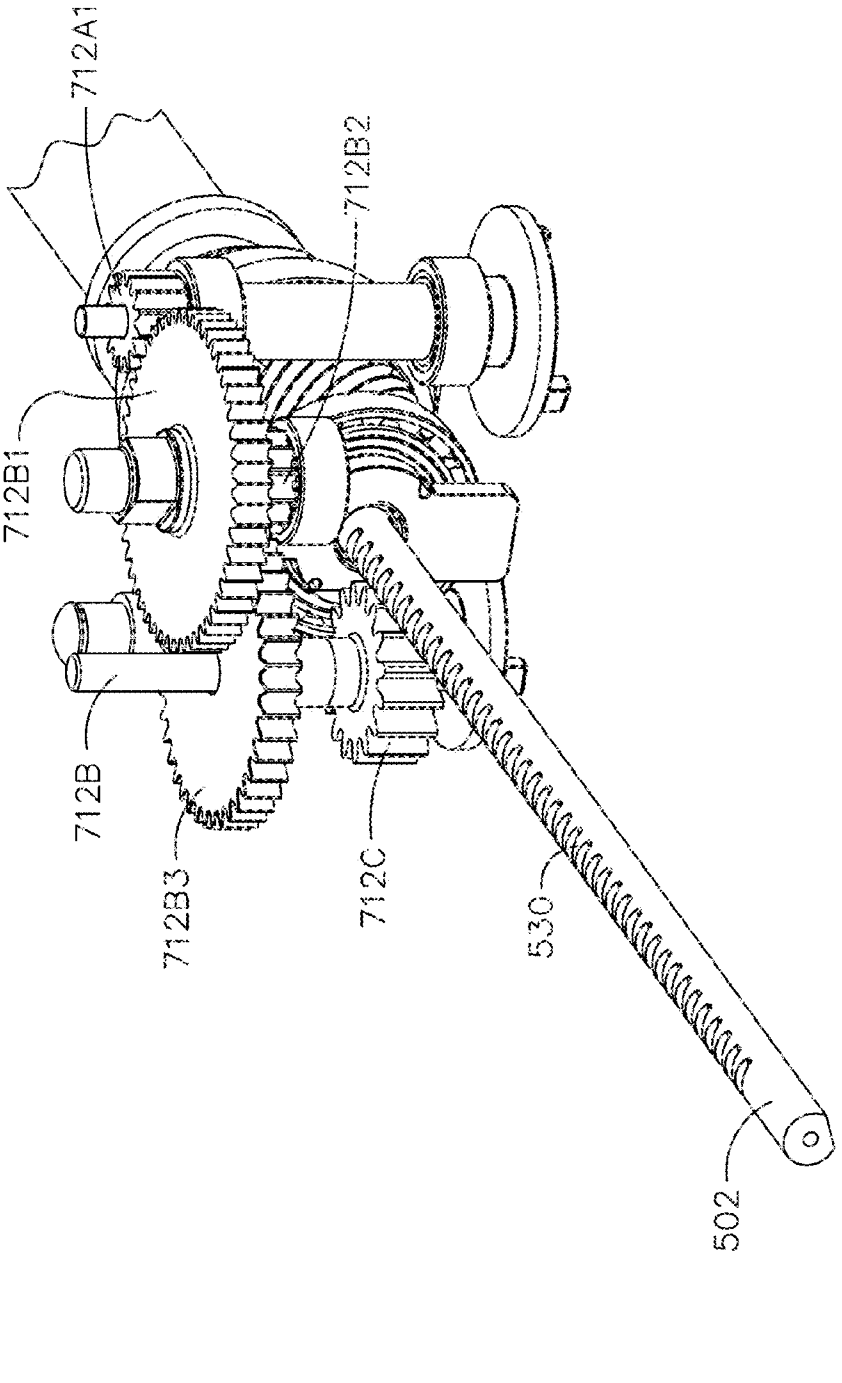
FIG. 23 is a schematic detail view of the proximal end of the surgical instrument, depicting portions of the knife firing subsystem, in accordance with the disclosed technology.

With continued reference to FIGS. 20-22, the entirety of the push rods 504, 506 do not bend and/or extend through the articulation joint 300, in use, and therefore does not need to be flexible. Accordingly, a proximal section of each push rod 504, 506 includes a rigid rod 516, 518. As used, the term 'rigid' refers to a structure less flexible than the described push coils 508, 510 and cables 512, 514. Specifically, the first push rod 504 includes a first rigid rod 516 coaxial with and coupled to the first push coil 508 and first center cable 512, and the second push rod 506 includes a second rigid rod 518 coaxial with and coupled to the second push coil 510 and second center cable 514.

Further to the above, depending on the manner in which the end effector 200 is pivoted about the articulation joint 300, the bend radius for the first push coil 508 and the second push coil 510 can differ. For example, in the configuration shown in FIG. 21 (i.e., when the end effector 200 is pivoted upwards), the first push coil 508 has a smaller bend radius than the second push coil 510, leading to a greater amount of the second push coil 510 extending through the articulation joint 300 than the first push coil 508. A differential 520 is provided to account for these differing bend radii, as well as to balance any difference in loading, ensuring an even split of the firing force being delivered to the push rods 504, 506.

More specifically, the differential 520 couples the first push rod proximal end 504B and the second push rod proximal end 506B to the firing rod 502, and the differential 520 permits relative axial movement between the first push rod 504 and the second push rod 506 (e.g., as depicted from FIG. 20 to FIG. 21). The differential 520 includes a first rack 522 coupled to the first push rod 504, a second rack 524 coupled to the second push rod 506, a pinion bar 526 coupled to the firing rod 502, and a pinion 528 rotatably mounted on the pinion bar 526 and meshed with the first rack 522 and the second rack 524.

Further to the above, as particularly exemplified in FIGS. 20-21, the first rack 522 and the second rack 524 are movable in opposing axial directions relative to one another in response to rotation of the sled 236 about the pitch axis PA to account for the aforementioned differing bend radii of the push coils 508, 510.

Further, as shown in FIG. 22, the first rack 522 and the second rack 524 are each movable in the same axial direction (e.g., a first axial direction) in response to movement of the firing rod 502 in the first axial direction with a firing force. As discussed above, this firing force is delivered through the push coils 508, 510 to the knife 206, which closes the anvil 204 to a grasping position and/or a clamping position. As shown in the sequence depicted in FIGS. 9A-9D, movement of the push coils 508, 510 distally results in them riding in the central upper knife channel portion 226 of the upper knife channel 224 and the central lower knife channel portion 232 of the lower knife channel 224, respectively. Further movement of the firing rod 502 in the first axial direction continues movement of the knife 206 to fire the staples and transect tissue, as discussed above. Retraction of the knife 206 and opening of the anvil is achieved by moving the firing rod 502 in an opposite, second direction. As demonstrated in FIGS. 21 and 22, due to the independent cable articulation system 400 and knife firing system 500, the knife 206 and sled 236 can be oriented and translate non-parallel to an orientation and movement of the firing rod 502.

In order to permit roll of the shaft outer shaft 602, which is discussed in greater detail below, the differential 520 is mounted in the shaft assembly 600A and is coupled to the firing rod 502 such that it is rotatable about a roll axis RA. As a result, the pinion bar 526 is axially constrained relative to the firing rod 502 and freely rotatable relative thereto.

VI. OVERVIEW OF THE ROLL SUBSYSTEM

Figure 19:
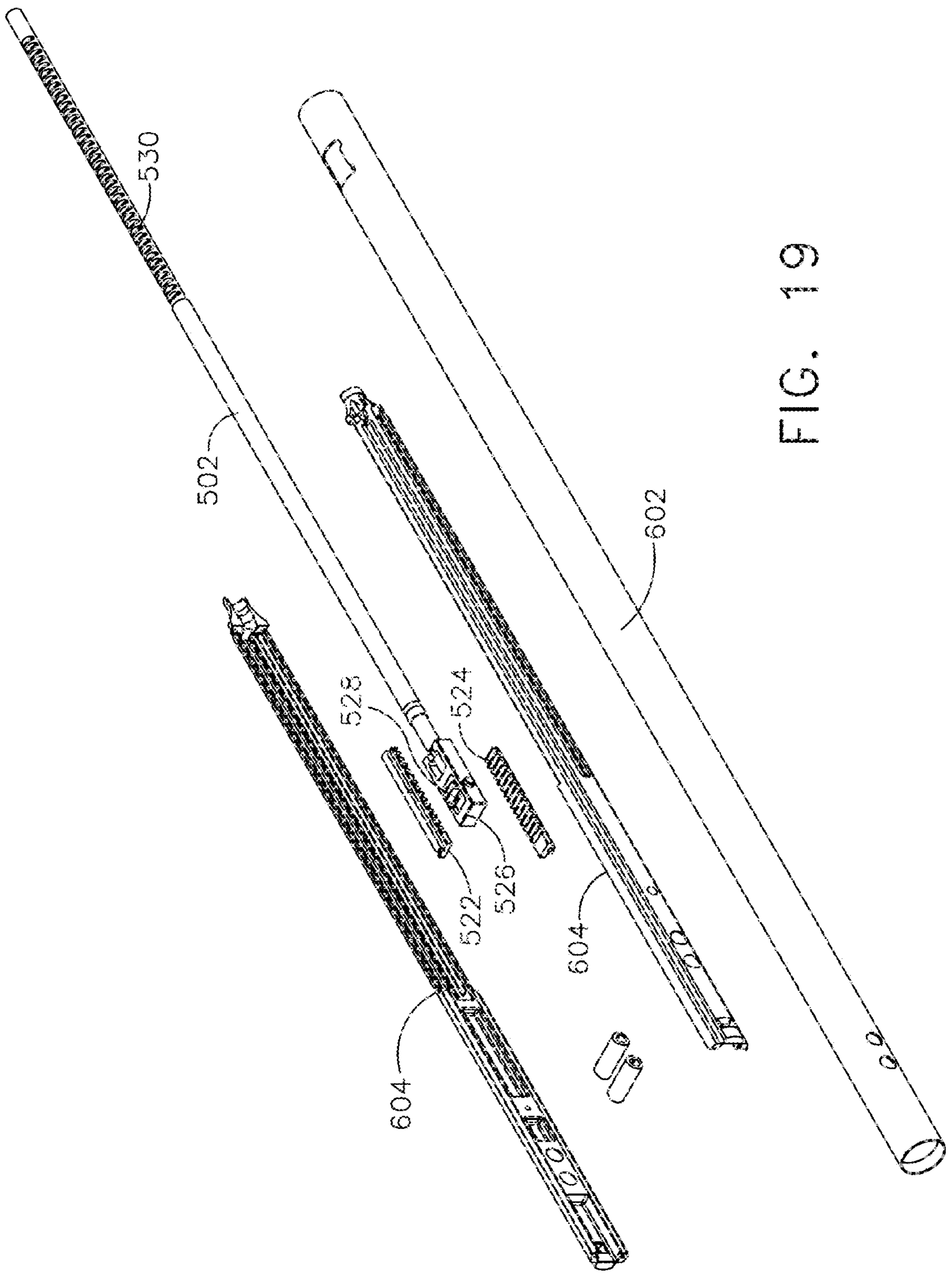
FIG. 19 is a schematic perspective view of a shaft assembly, a differential, and a firing rod of the surgical instrument, in accordance with the disclosed technology.
Figure 24:
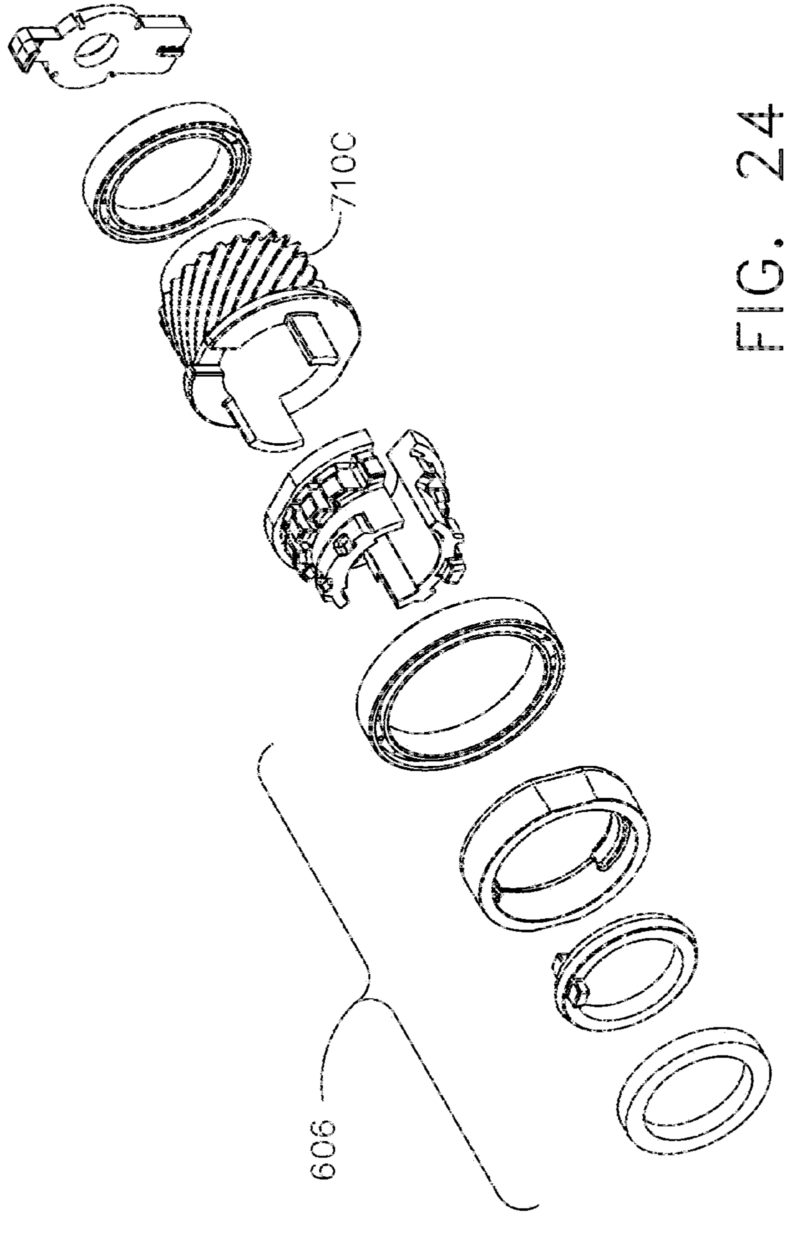
FIG. 24 is a schematic exploded detail view of a rotation joint, in accordance with the disclosed technology.
Figure 25:
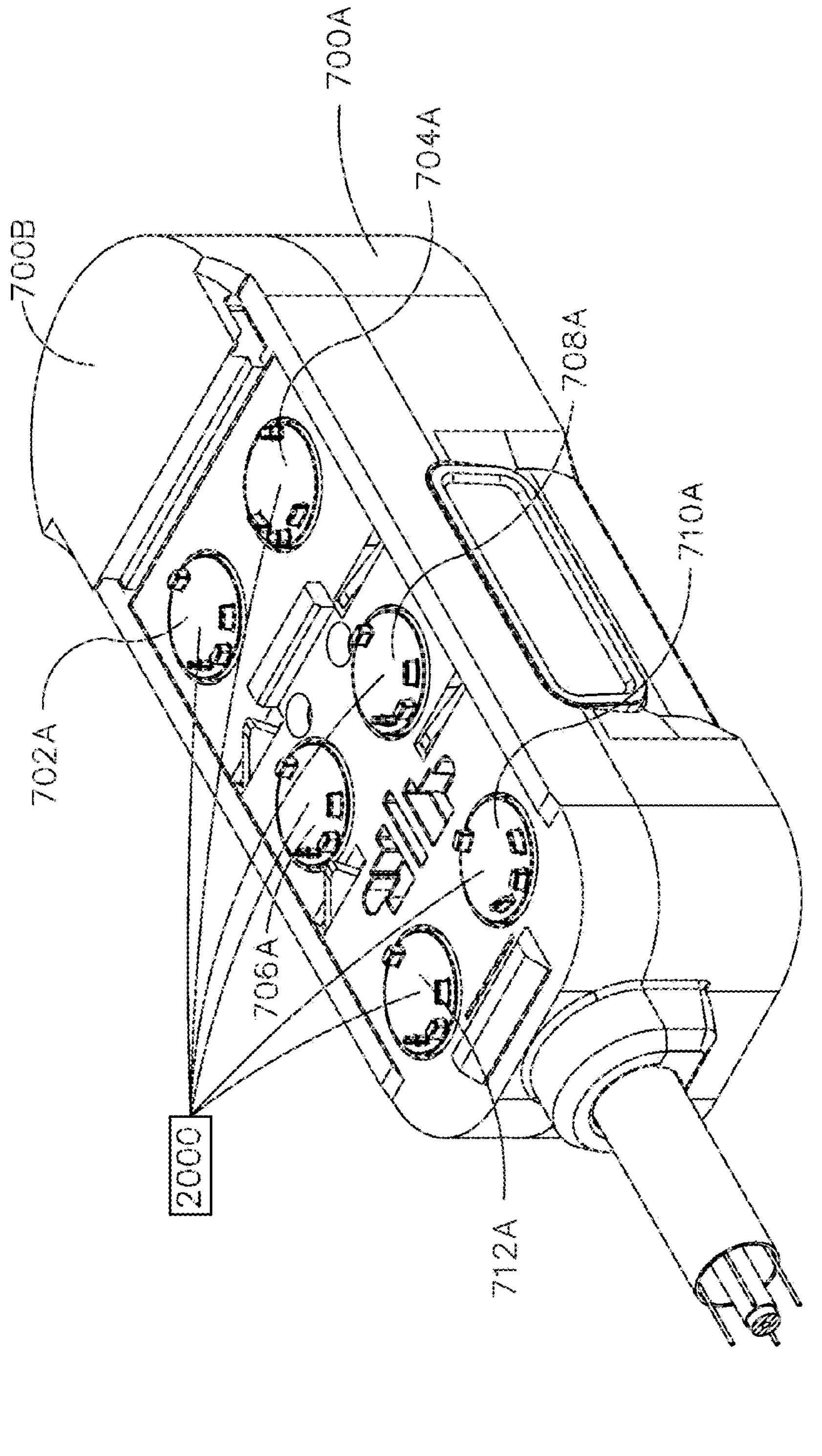
FIG. 25 is a schematic detail view of one side of a housing, depicting rotational pucks that engage a robotic platform, in accordance with the disclosed technology.
Figure 26:
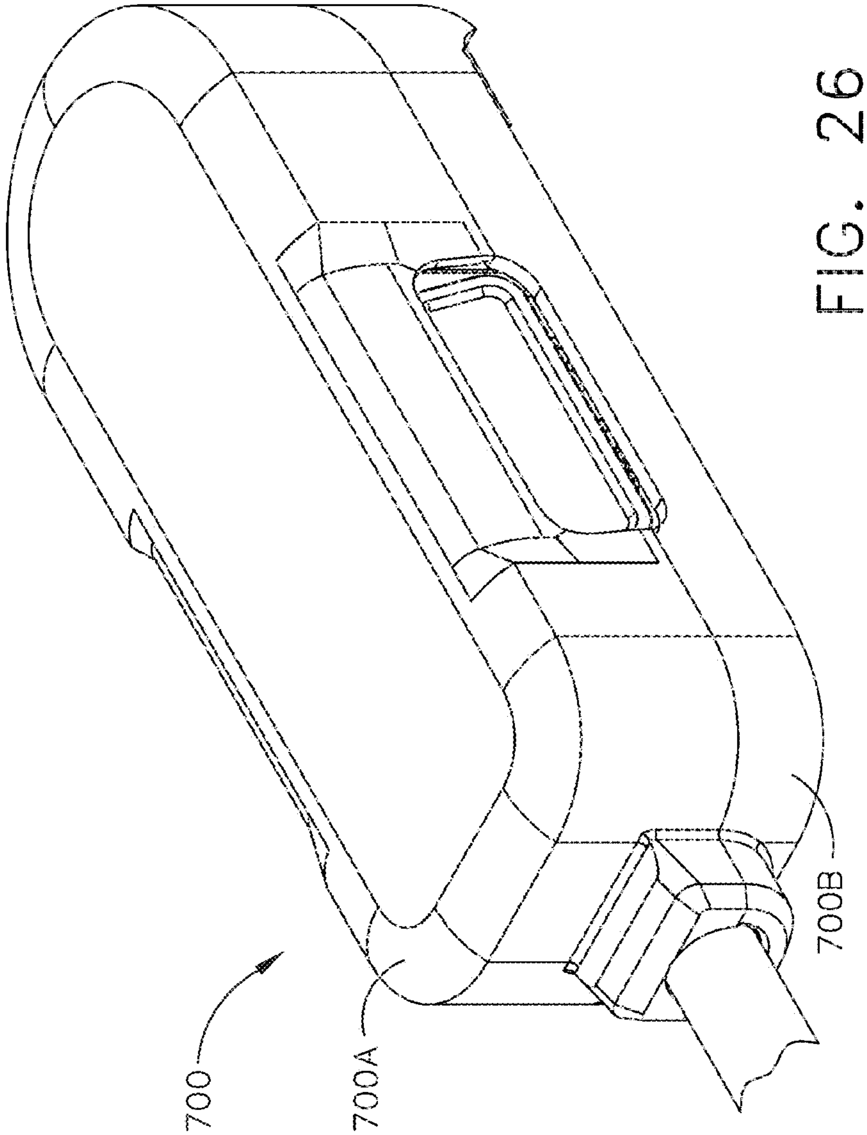
FIG. 26 is a schematic detail view of another side of the housing, in accordance with the disclosed technology.
Figure 27:
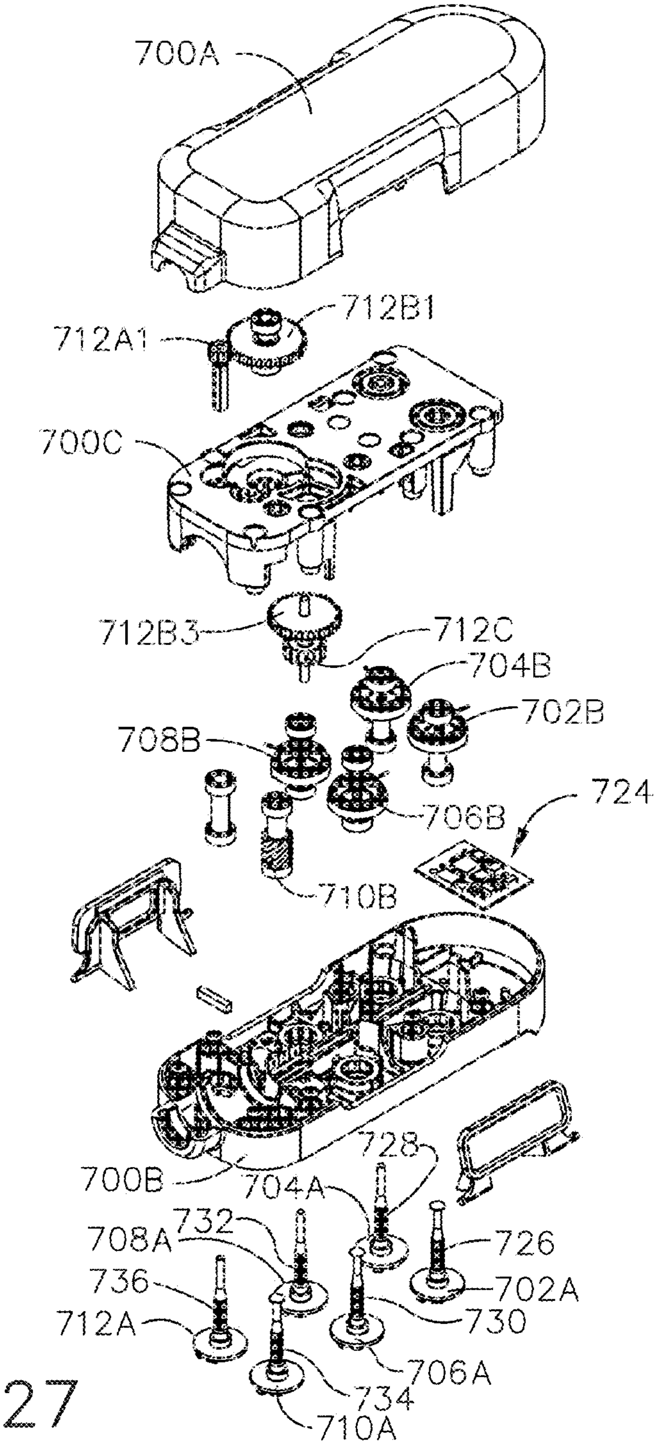
FIG. 27 is a schematic exploded view of the housing, in accordance with the disclosed technology.
Figure 28:
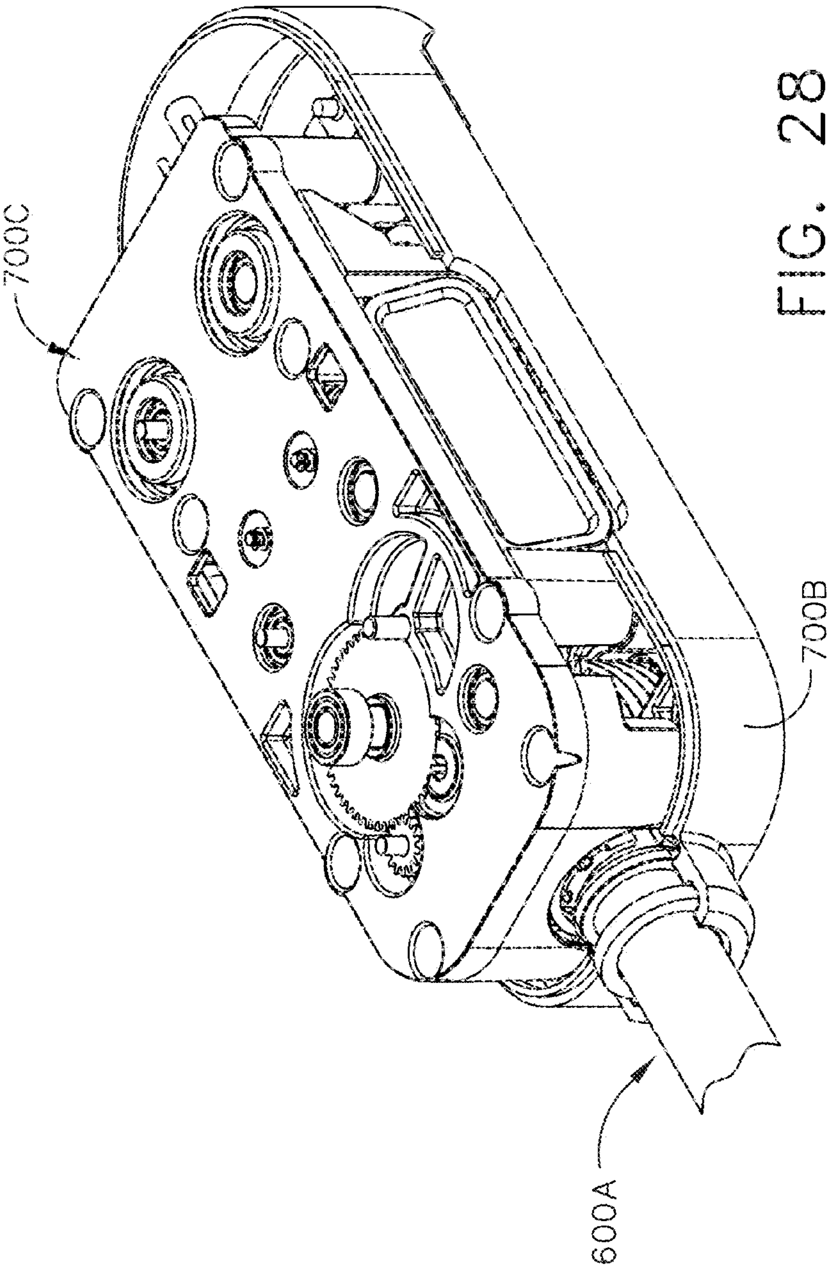
FIG. 28 is a schematic detail view of the housing with an upper shroud thereof removed, in accordance with the disclosed technology.
Figure 29:
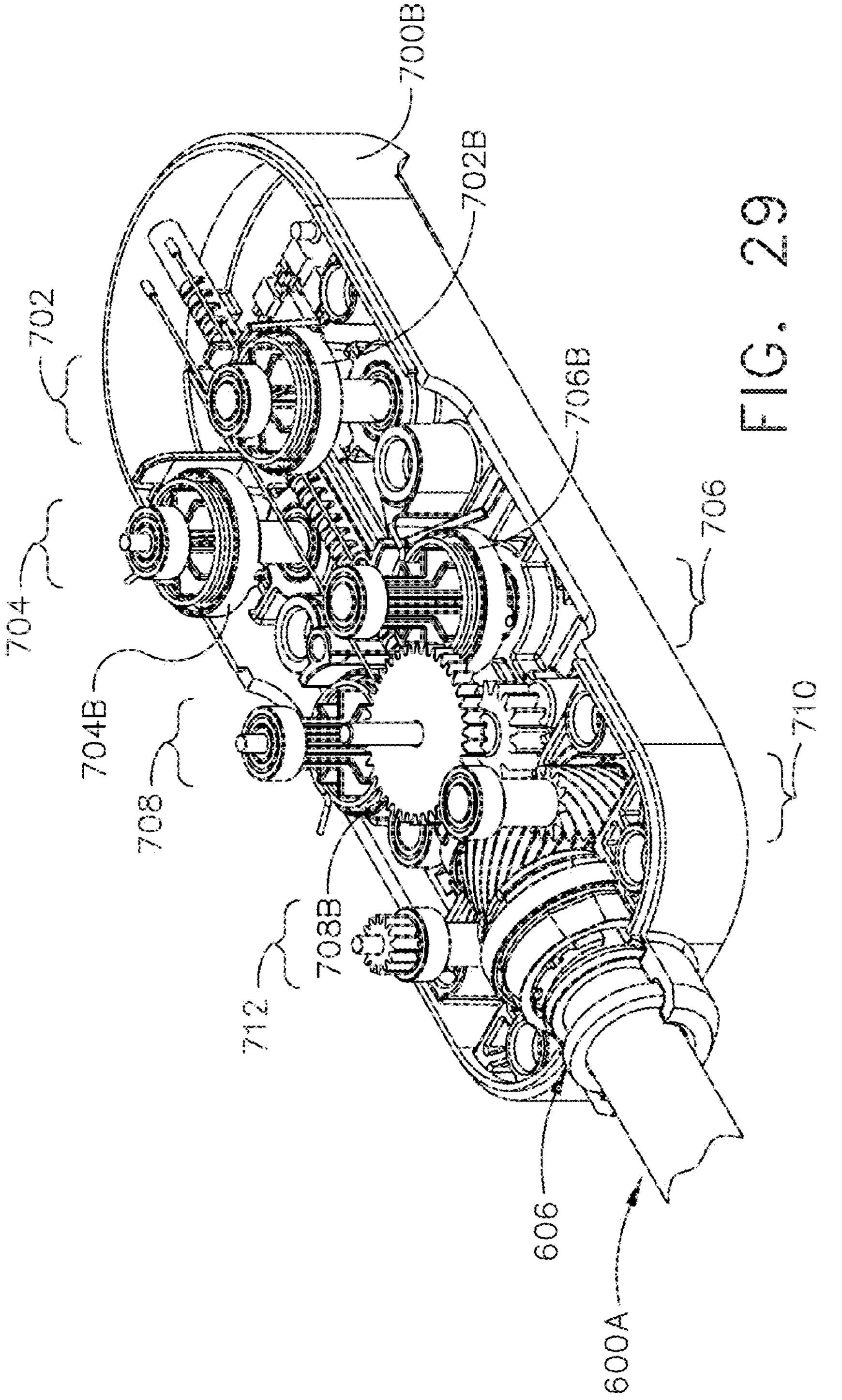
FIG. 29 is a schematic perspective view of the housing with the upper shroud and middle frame thereof removed, in accordance with the disclosed technology.
Figure 30:
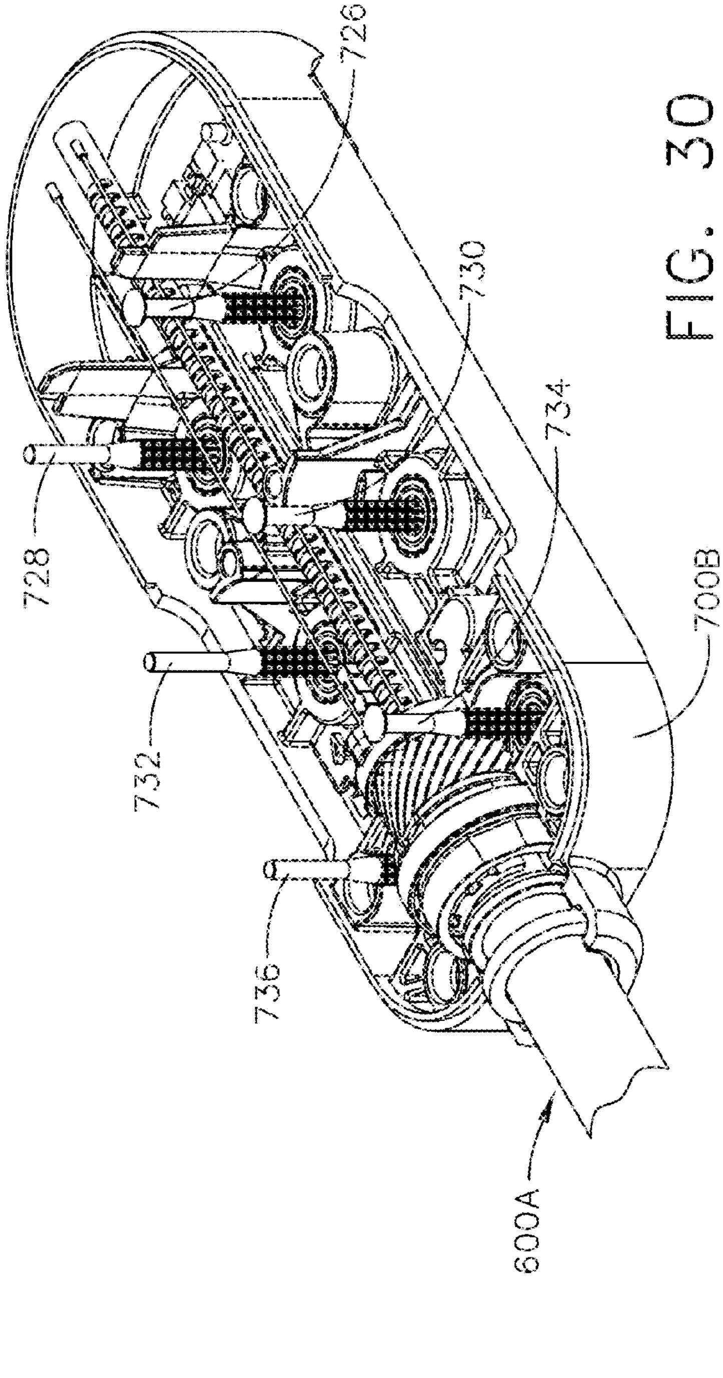
FIG. 30 is a schematic perspective view of the housing with the upper shroud, middle frame thereof removed, and certain subsystem components removed, in accordance with the disclosed technology.
Figure 31:
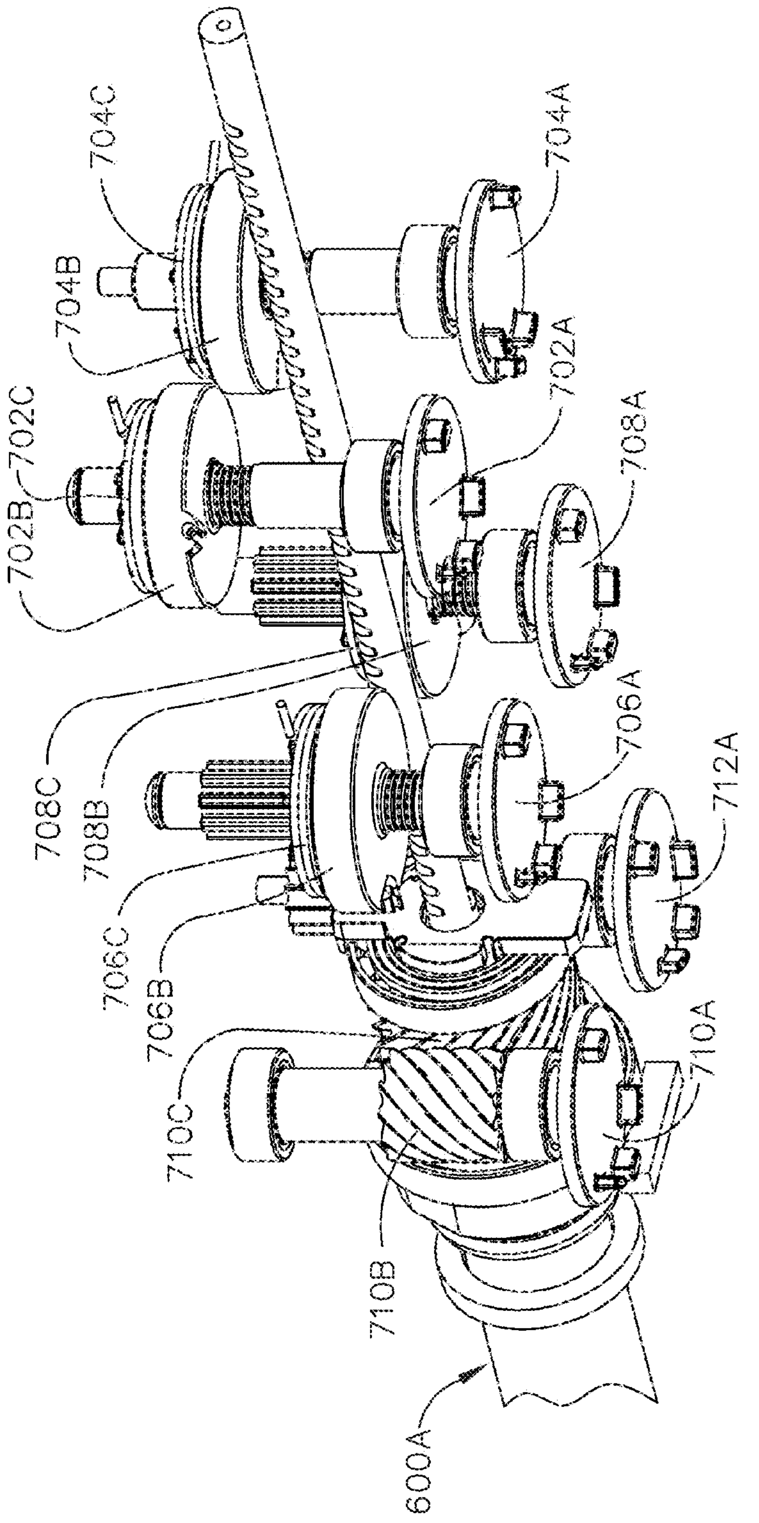
FIG. 31 is a schematic detail view of rotational puck assemblies of the housing, in accordance with the disclosed technology.
Figure 32:
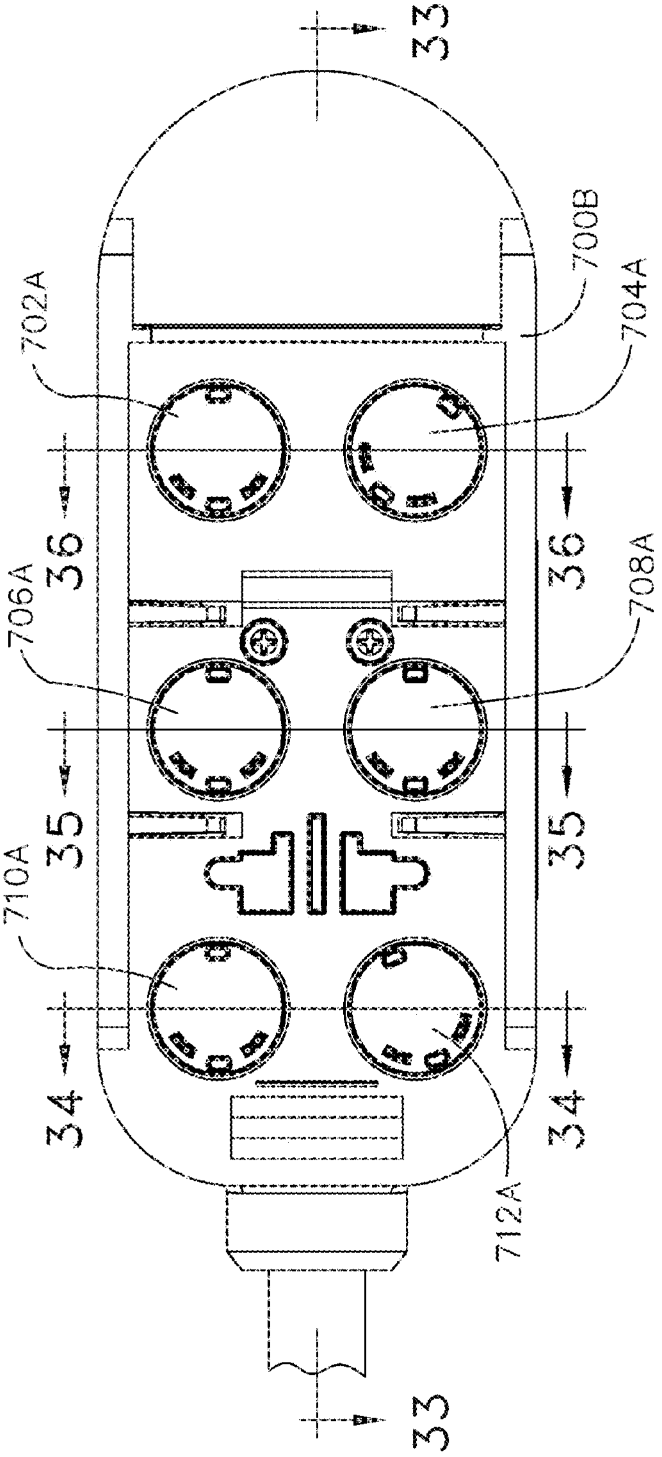
FIG. 32 is a schematic elevation view of the housing, in accordance with the disclosed technology.
Figure 33:
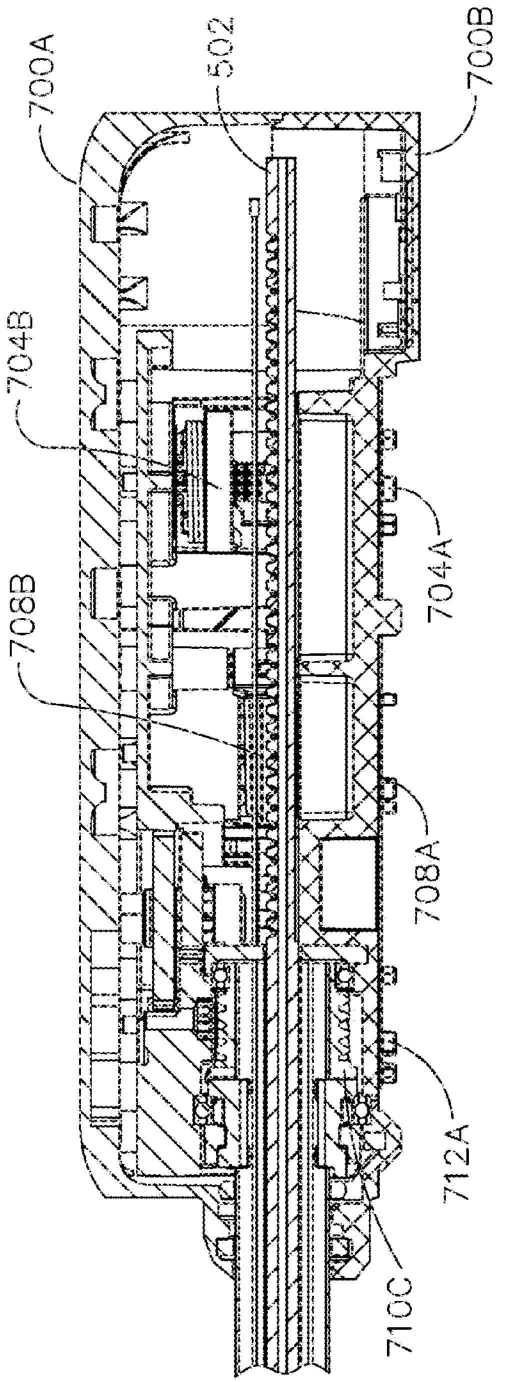
FIG. 33 is a schematic cross-sectional view of the housing, cut relative to line 33-33 in FIG. 32; in accordance with the disclosed technology.
Figure 34:
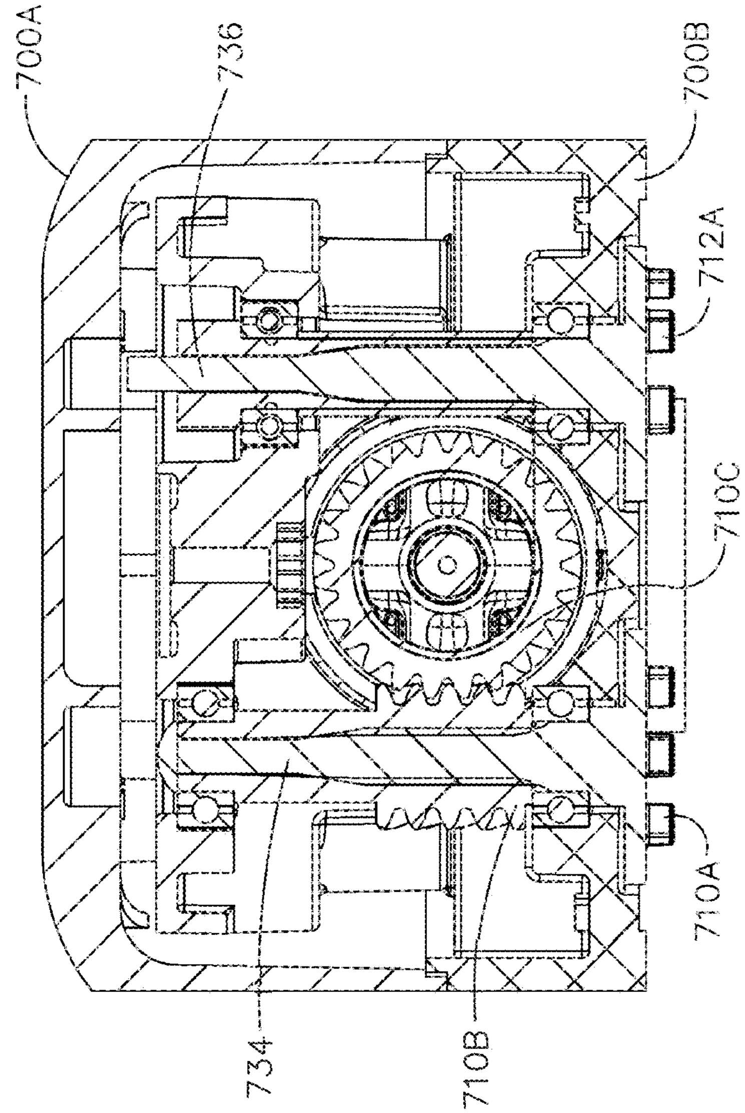
FIG. 34 is a schematic cross-sectional view of the housing, cut relative to line 34-34 in FIG. 32; in accordance with the disclosed technology.

Turning now to the roll subsystem 600, the roll subsystem includes the above-mentioned shaft assembly 600A, rotation joint 606, shaft roll puck assembly 710, which is discussed in greater detail below. As discussed in the foregoing paragraph, the rotatable nature of the differential 520 is also a feature of the roll subsystem. The shaft assembly 600A includes the previously discussed rotatable outer shaft 602 and the inner shaft 604. As shown in the exploded view of FIG. 19, the inner shaft 604 can be split clamshell in design that couple to one another and houses certain components of the surgical instrument 1000, such as the differential 520 and a distal portion of the firing rod 502. Additionally, the clamshell inner shaft 604 can provide support for certain portions of the push coils 508, 510. The inner shaft 604 is fixedly coupled to the outer shaft 602 such that they are rotationally linked. The outer shaft 602 is coupled to the housing via the rotation joint 606, which may include one or more bearings (see, e.g., FIGS. 24 and 27). The bearings engage the housing 700 and permit relative rotation between the outer shaft 604 and the housing 700 upon actuation of the shaft roll puck assembly, which is described in greater detail below. One or both of the shafts 602, 604 are provided with various channels for the cables 402, 404, 406, 408, push rods 504, 506, differential 520, and the like to ride in. Further, a lug is rotationally fixed to the outer shaft and is configured to bottom out with a cavity on the housing to indicate when the outer shaft 602 is in a home position.

VI. 1. Maypole Tube

Figure 38:
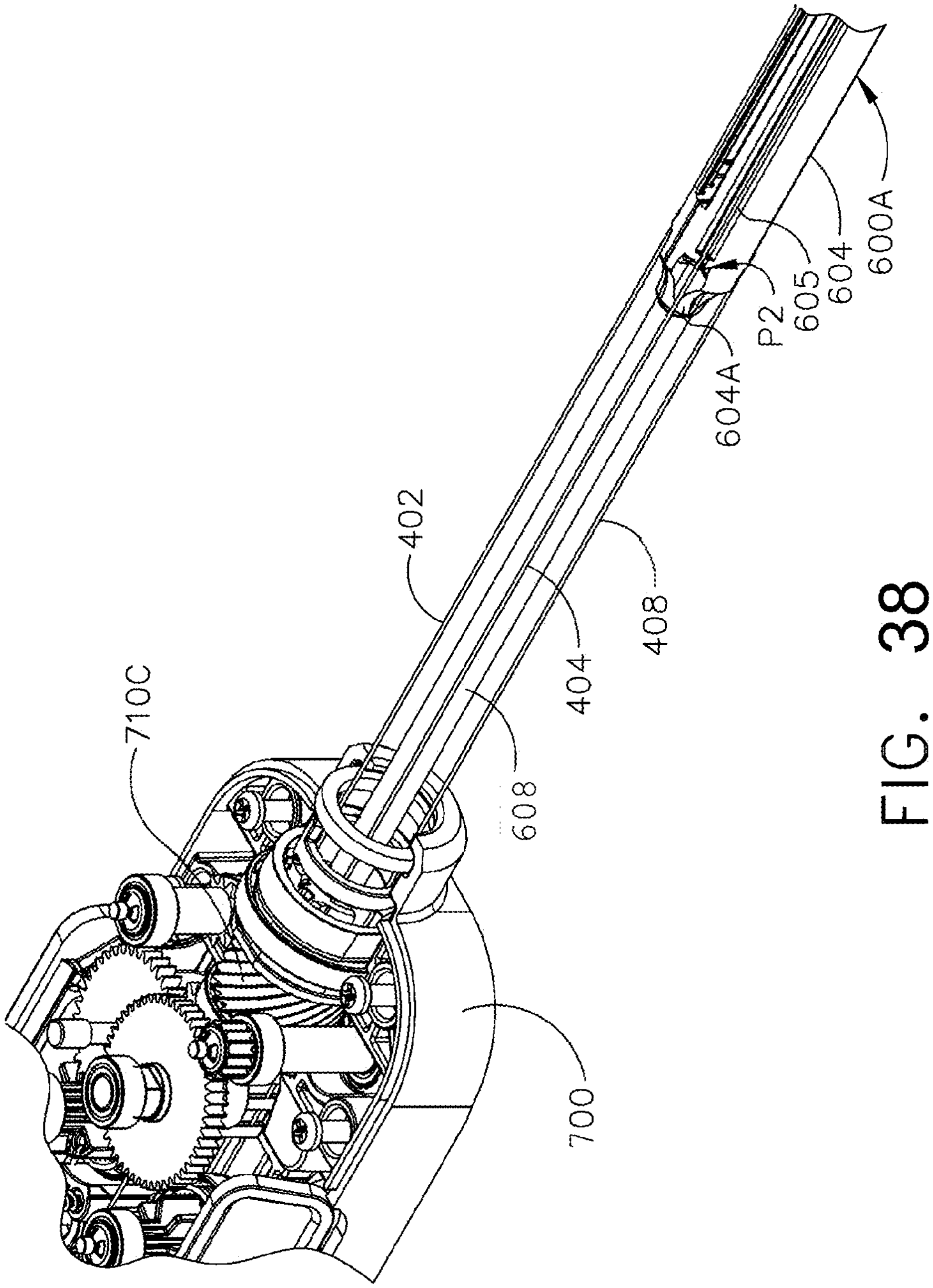
FIG. 38 is a schematic detail perspective view of a mid-section of an alternative surgical instrument, showing a maypole tube surrounding the firing rod, with an outer shaft and an upper shell of the housing removed for clarity, in accordance with the disclosed technology.
Figure 39:
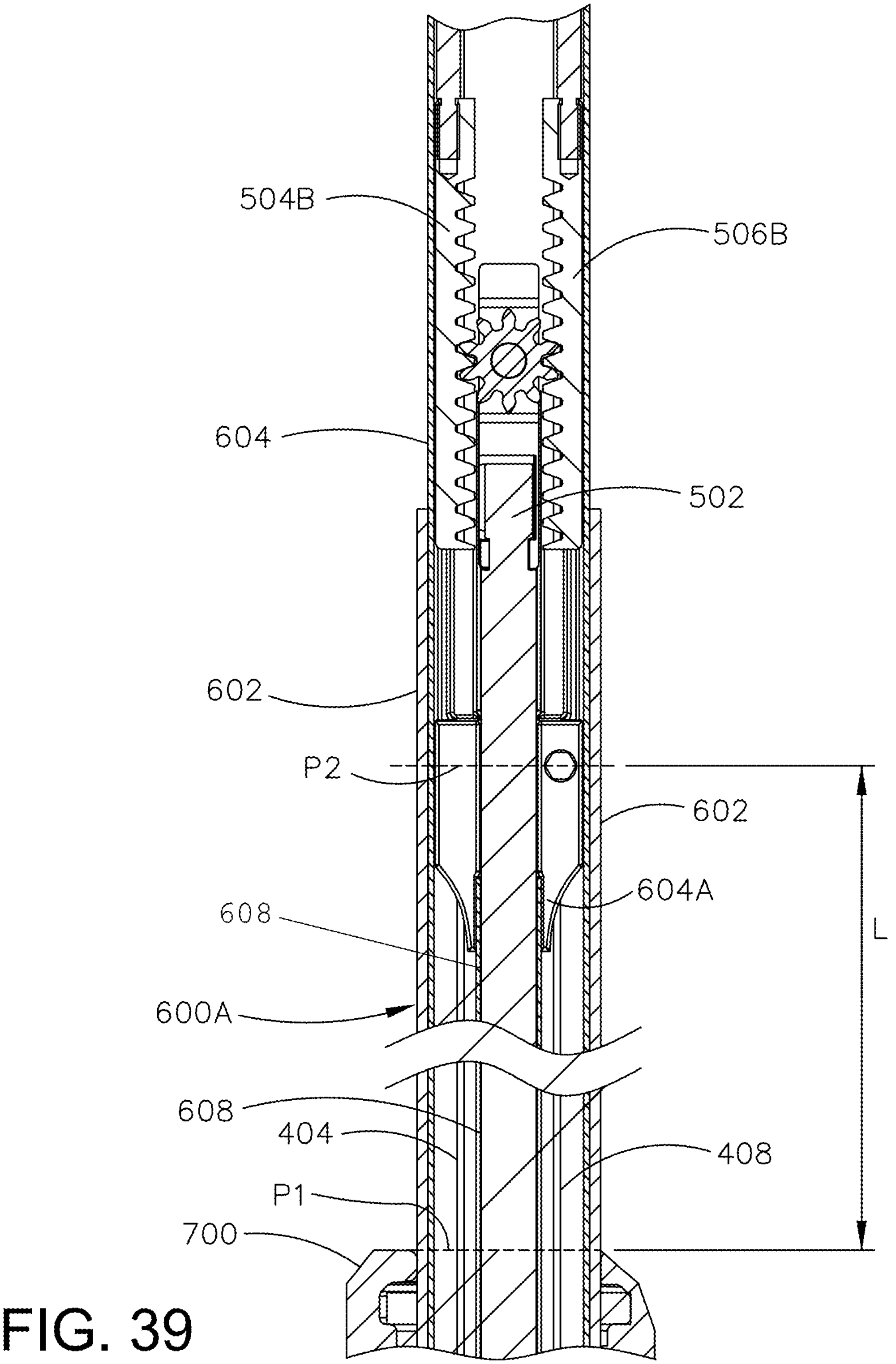
FIG. 39 is a schematic detail cross-sectional view of the alternative surgical instrument of FIG. 38, cut along the roll axis, showing the maypole tube surrounding the firing rod and abutting with the differential, in accordance with the disclosed technology.
Figure 40:
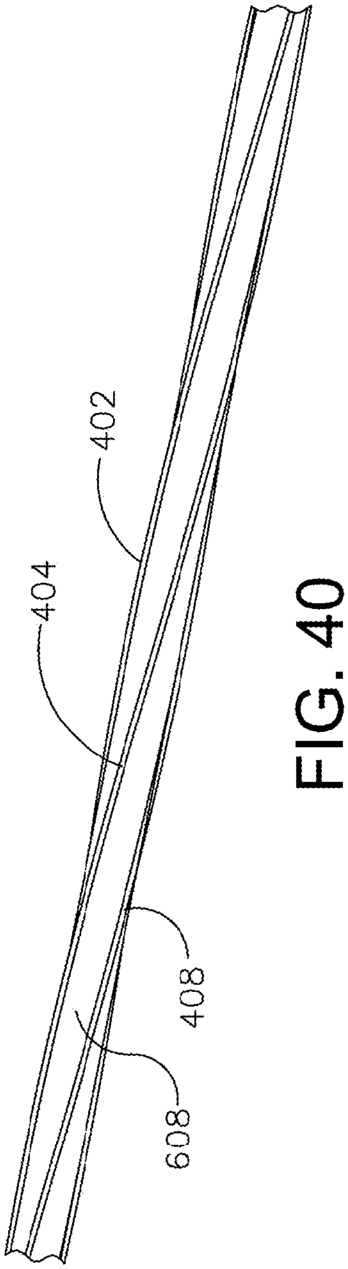
FIG. 40 is a schematic detail perspective view of the maypole tube of FIG. 38, showing articulation cables wrapping therearound when the end effector rolls, in accordance with the disclosed technology.
Figure 41A:
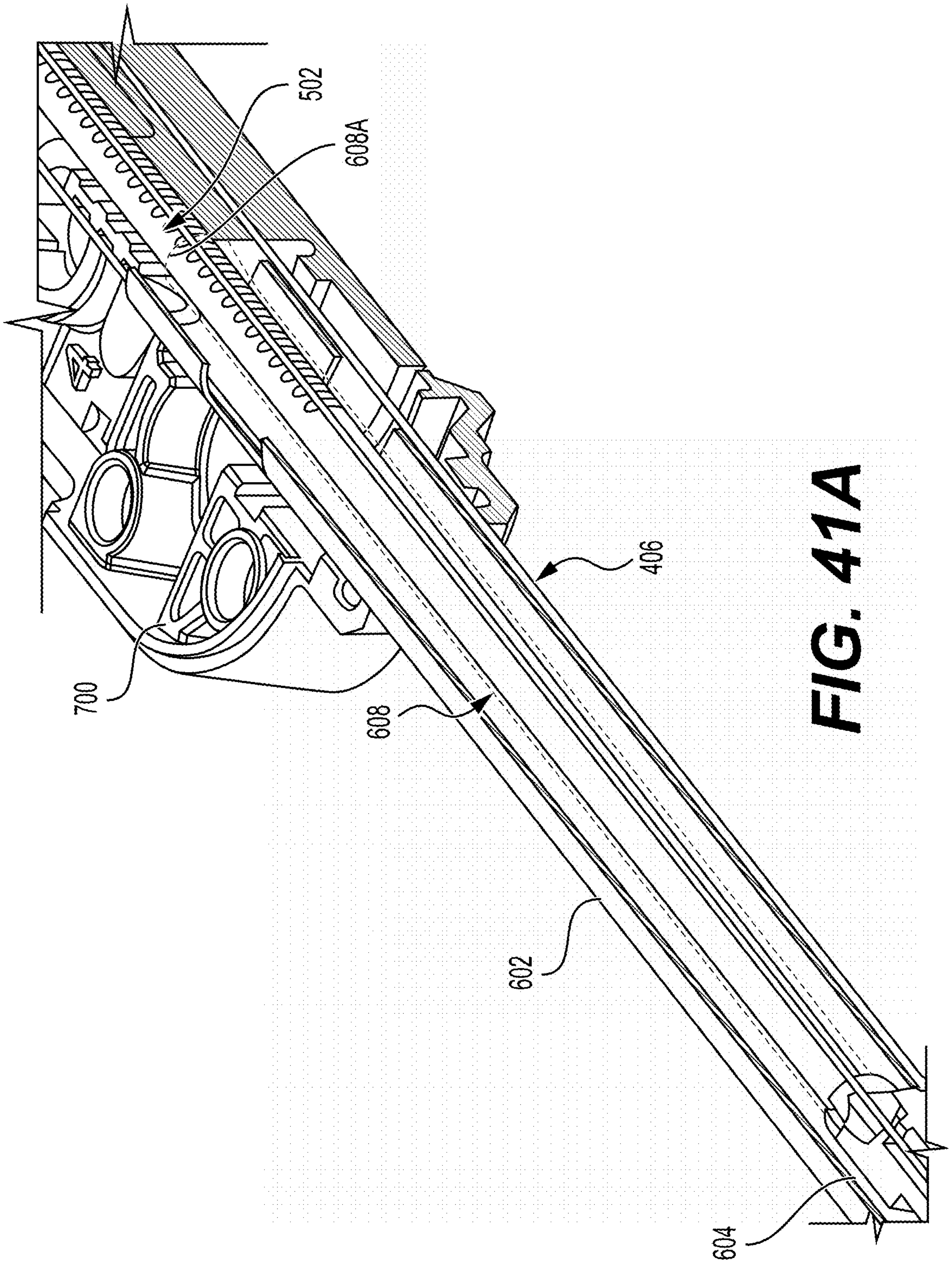
FIG. 41A is a schematic detail perspective view of the mid-section of the alternative surgical instrument of FIG. 38, showing the maypole tube in phantom lines and with a portion of the housing and outer shaft removed for clarity, in accordance with the disclosed technology.
Figure 41B:
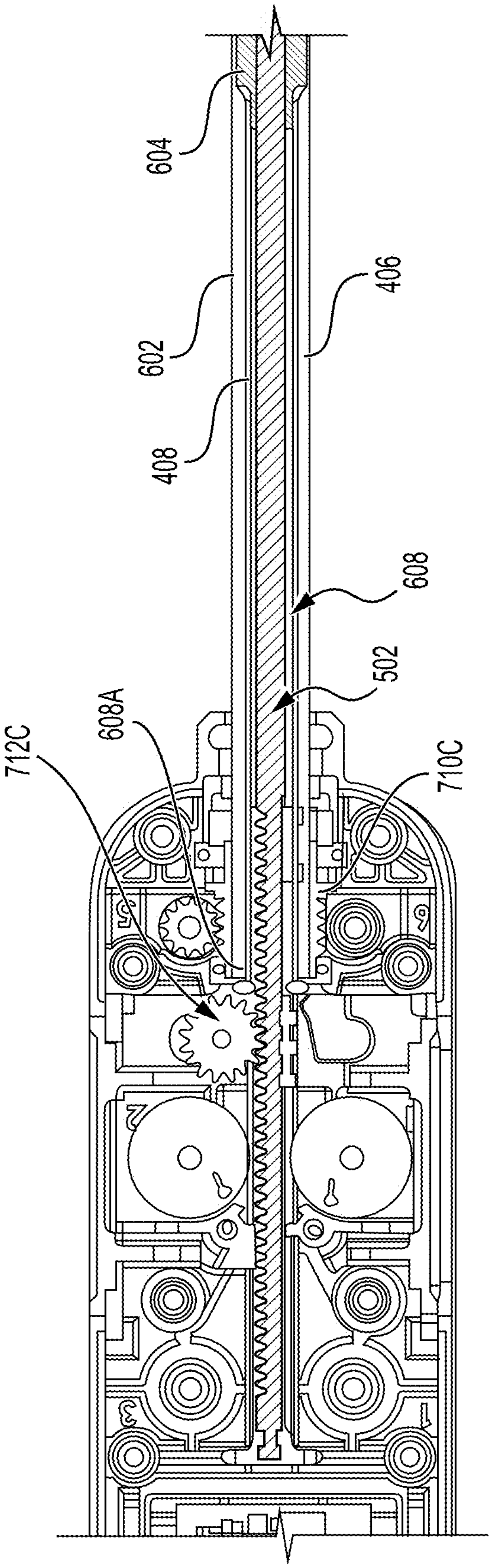
FIG. 41B is a schematic elevation view of the mid-section of the alternative surgical instrument of FIG. 38, depicting a layout of components in the handle and mid-section, in accordance with the disclosed technology.

Turning now to FIGS. 38-40, an alternative example of the roll subsystem 600 is shown. This example is similar to the previously described roll subsystem 600 and shaft assembly 600A but incorporates a maypole tube 608 concentrically located with the firing rod 502 to decouple the articulation cables 402, 404, 406, 408 from the firing rod 502. As used herein, the terms "maypole" and "maypoling" is used to describe the action of winding the articulation cables 402, 404, 406, 408 around the firing rod 502 or another tube (like the maypole tube 608 described herein) when the outer shaft 602 is rolled (e.g., up approximately 320 degrees in a clockwise or counterclockwise direction). FIG. 40 illustrates this concept. As will be appreciated by those skill in the art, if the articulation cables 402, 404, 406, 408 maypole around the firing rod 502, which translates, it is possible that one or more of the cables 402, 404, 406, 408 can pinch on the firing rod 502, causing a malfunction of the surgical instrument 1000 and/or damage to the articulation cables 402, 404, 406, 408.

Therefore, as seen in FIGS. 38-41B, alternative roll subsystems can be embodied similarly as described as other examples disclosed herein. For example, this subsystem can include a similar shaft assembly 600A with an inner shaft 604 rotationally fixed to a rotatable outer shaft 602 (the rotatable outer shaft 602 is hidden in FIG. 38 in order to depict the maypole tube 608). Thus, rotation of the outer shaft 602 causes rotation of the inner shaft 604. The inner shaft 604 can include support channels 605 to support, guide, and/or rotationally constrain the articulation cables 402, 404, 406, 408, in particular when the shaft assembly 600A rolls. The inner shaft can also include a reduced diameter transition section 604A that the articulation cables 402, 404, 406, 408, discussed in greater detail below, can be partially wound therearound without becoming tangled. While discussed particularly with reference to the example of FIG. 38, those skilled in the art will appreciate that the inner shaft 604 of, e.g., FIG. 19 can also be embodied in an equivalent manner (these details can also be seen in the clamshell halves of the inner shaft 604 in FIG. 19).

A maypole tube 608 is provided (1) between a screw gear 710C (discussed in greater detail below) and the transition section 604A of the inner shaft 604 in the maypoling section of the articulation cables 402, 404, 406, 408 where they are rotationally unconstrained and (2) between the outer shaft 602 and the firing rod 502 in a radial direction (e.g., the outer shaft 602, the maypole tube 608, and firing rod 502 can be concentric with one another, with the maypole tube 608 being housed within the outer shaft 602). Due to the use of cables 402, 404, 406, 408 for articulation, since the housing 700 is connected to a robotic platform 2000, it is important that they have a section that is unconstrained in order to enable the surgical instrument 1000 to roll. The maypole tube 608 entirely surrounds the portion of the firing rod 502 that extends in this section and, as discussed above, decouples the articulation cables 402, 404, 406, 408 from the firing rod 502. Moreover, a proximal end 608A (FIGS. 41A and 41B) of the maypole tube 608 extends into the housing 700 and can be flared (i.e., has an increasing diameter in a direction away from the end effector 200), which helps to prevent the teeth of the firing rod 502 from catching on the maypole tube 608 as the firing rod 502 translates (as discussed in other sections). The maypole tube 608 is rotationally unconnected from the components it is adjacent to and/or abuts, meaning that it is neither locked to a rotating reference frame (e.g., when the outer shaft 602 is rotated) nor a static reference frame (e.g., the housing 700 when the outer shaft 602 is rotated). As seen particularly in FIGS. 39 and 41A-41B, in the maypoling section, the articulation cables 402, 404, 406, 408 are disposed between the outer shaft 602 and the maypole tube 608 and are rotationally unconstrained along an entire length of the maypole tube 608.

As schematically depicted in FIG. 40 (which omits other elements to demonstrate how the articulation cables 402, 404, 406, 408 maypole around the maypole tube 608), in use, when the end effector 200 is rolled, the articulation cables 402, 404, 406, 408 wrap around the maypole tube 608, thus keeping them mechanically isolated from other moving components of the surgical instrument 1000 (e.g., the firing rod 502). Because the maypole tube 608 is loosely sandwiched between components of the surgical instrument 1000 adjacent thereto, as the articulation cables 402, 404, 406, 408 wrap around the maypole tube 608, frictional forces can cause the maypole tube 608 to rotate relative the housing 700 (which is rotationally static) as well as the outer and inner shafts 602, 604 (whose rotation cause the articulation cables 402, 404, 406, 408 to wrap around the maypole tube). By making the maypole tube 608 indeterminant, the effect on the roll subsystem of the frictional forces between the maypole tube 608 and articulation cables 402, 404, 406, 408 can be minimized.

When employed, it is desirable that the diameter of the maypole tube 608 be minimized as much as possible. This provides various benefits, such as such as minimizing the number of wraps around the maypole tube 608, which reduces friction. It also limits the amount of axial length consumed during maypoling, which minimizes the among of compensation required by the articulation subsystem 400 (discussed in greater detail in section VIII. 1.).

Figure 42A:
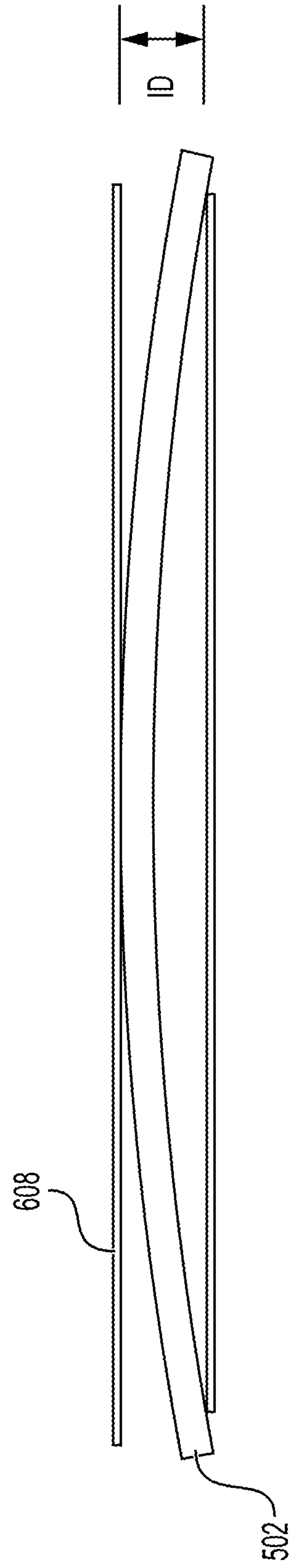
FIG. 42A is a schematic detail view of a rigid maypole tube and a deflected firing rod, in accordance with the disclosed technology.
Figure 42B:
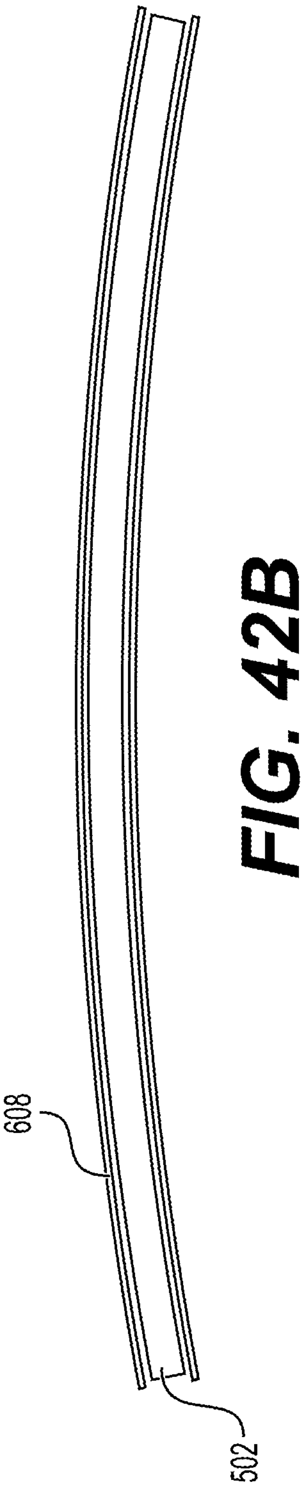
FIG. 42B is a schematic detail view of a compliant maypole tube deflecting with the firing rod, in accordance with the disclosed technology.

Besides the aforementioned challenges of the teeth potentially getting caught on the maypole tube 608 as the firing rod 502 translates, the firing rod 502 also experiences subtle radial deflection due to eccentric loading from the pinion 712C (discussed in greater detail below) and compressive/buckling loads. FIGS. 42A and 42B depict exaggerated deformation of the firing rod 502. Friction/cable drag between the cables 402, 404, 406, 408 and the maypole tube 608 is also of concern, particularly when one or more of the cables 402, 404, 406, 408 are used to articulate the end effector 200 while they are simultaneously wrapped around the maypole tube 608 (e.g., in a state where the end effector 200 has been rolled by the roll subsystem 600).

Therefore, further to the above, and with reference to FIGS. 41A-42B, to address the above design considerations, the maypole tube 608 may be embodied as follows.

One example is depicted in FIG. 42A, with (as mentioned above) exaggerated firing rod deflection for illustrative purposes. In this example, the maypoling tube 608 is formed from a rigid material and is sized such that its inner diameter ID provides sufficient clearance to the outer diameter of the firing rod 502 to allow it to radially deflect withing creating a binding condition at the ends of the maypole tube 608.

Another example is depicted in FIG. 42B with (as mentioned above) exaggerated firing rod deflection for illustrative purposes. In this example, the maypole tube 608 is formed from a compliant material with minimal clearance to the outer diameter of the firing rod 502. This configuration allows the maypole tube 608 to deflect with the firing rod 502 without creating binding conditions at the end of the maypole tube 608.

In addition, the two exemplary maypole tubes 608 shown in FIGS. 42A and 42B can be formed with a lubricious additive which reduces friction between the maypole tube 608 and the firing rod 502 and also allows smoother cable motion during articulation when the articulation cables 402, 404, 406, 408 are wrapped around the maypole tube 608.

VII. OVERVIEW OF THE HOUSING PUCK ASSEMBLIES AND INTEGRATION WITH THE SURGICAL INSTRUMENT SUBSYSTEMS

Turning now primarily to FIGS. 23-35, the housing 700 is configured to engage a robotic platform 2000 controlled by a clinician. To control the aforementioned subsystems 400, 500, 600, respective proximal mechanisms are provided that interface with the robotic platform. More specifically, a housing outer shell, which includes an upper shroud 700A, a lower frame 700B, and a middle frame 700C, houses at least (1) a plurality of articulation puck assemblies 702, 704, 706, 708 for articulation of the end effector 200, (2) a shaft roll puck assembly 710 for rolling the outer shaft 602, (3) a firing puck assembly for translating the knife 206, and (4) a near field radio-frequency identification (RFID) board 724 that communicates information about the surgical instrument 1000 to the robotic platform 2000.

VII. 1. Housing and Articulation Subsystem

Further to the above, the housing includes four articulation puck assemblies 702, 704, 706, 708, provided that four articulation cables 402, 404, 406, 408 are employed in the presently described surgical instrument. A first articulation puck assembly 702 is used cooperatively with the first articulation cable 402. Likewise, the second articulation puck assembly 704 is used cooperatively with the second articulation cable 404, the third articulation puck assembly 706 is used cooperatively with the third articulation cable 406, and the fourth articulation puck assembly 708 is used cooperatively with the first articulation cable 408. In use, the first articulation cable 402 winds on and off the first articulation puck assembly 702, the second articulation cable 404 winds on and off the second articulation puck assembly 704, the third articulation cable 406 winds on and off the third articulation puck assembly 706, and the fourth articulation cable 408 winds on and off the first articulation puck assembly 708.

The first articulation puck assembly 702 includes a first articulation puck 702A, a first capstan 702B, and a first torsion spring 702C. The first articulation puck 702A is provided on an outer face of the lower frame 700B and directly engages the robotic platform 2000. The first capstan 702B is coupled to the first articulation puck 702A and winds the first articulation cable 402 therearound. The first capstan 702B is rotationally affixed to a first pivot pin 726 (which is integral with the first articulation puck 702A). The first capstan 702B is biased by a first torsion spring 702C in a retracting direction to maintain a minimum level of tension in the first articulation cable 402, such as while decoupled from the robotic platform 2000. As the first articulation puck assembly 702 does not include any gearing, the diameter of the first capstan 702B is what dictates the mechanical advantage achieved.

In use, and for example, rotation of the first capstan 702B by the robotic platform 2000, via the first articulation puck 702A, in a first direction winds the first articulation cable 402 around the first capstan 702B, which results in the end effector 200 pivoting upwards and to the left about the articulation joint 300. As discussed earlier, this upwards movement of the end effector 200 is compensated for in the knife firing subsystem by the differential 520. Rotation in the opposite direction by the first articulation puck 702A unwinds the first articulation cable 402 to return the end effector 200 to a position substantially coaxial with the shaft assembly 600A (e.g., coaxial with the roll axis RA).

The second articulation puck assembly 704 includes a second articulation puck 704A, a second capstan 704B, and a second torsion spring 704C. The second articulation puck 704A is provided on an outer face of the lower frame 700B and directly engages the robotic platform 2000. The second capstan 704B is coupled to the second articulation puck 704A and winds the second articulation cable 404 therearound. The second capstan 704B is rotationally affixed to a second pivot pin 728 (which is integral with the second articulation puck 704A). The second capstan 704B is biased by a second torsion spring 704C in a retracting direction to maintain a minimum level of tension in the second articulation cable 404. As the second articulation puck assembly 704 does not include any gearing, the diameter of the second capstan 704B is what dictates the mechanical advantage achieved.

In use, and for example, rotation of the second capstan 704B by the robotic platform 2000, via the second articulation puck 704A, in a first direction winds the second articulation cable 404 around the second capstan 704B, which results in the end effector 200 pivoting upwards and to the right about the articulation joint 300. As discussed earlier, this upwards movement of the end effector 200 is compensated for in the knife firing subsystem by the differential 520. Rotation in the opposite direction by the second articulation puck 704A unwinds the second articulation cable 404 to return the end effector 200 to a position substantially coaxial with the shaft assembly 600A (e.g., coaxial with the roll axis RA).

The third articulation puck assembly 706 includes a third articulation puck 706A, a third capstan 706B, and a third torsion spring 706C. The third articulation puck 706A is provided on an outer face of the lower frame 700B and directly engages the robotic platform 2000. The third capstan 706B is coupled to the third articulation puck 706A and winds the third articulation cable 406 therearound. The third capstan 706B is rotationally affixed to a third pivot pin 730 (which is integral with the third articulation puck 706A). The third capstan 706B is biased by a third torsion spring 706C in a retracting direction to maintain a minimum level of tension in the third articulation cable 406. As the third articulation puck assembly 706 does not include any gearing, the diameter of the third capstan 706B is what dictates the mechanical advantage achieved.

In use, and for example, rotation of the third capstan 706B by the robotic platform 2000, via the third articulation puck 706A, in a first direction winds the third articulation cable 406 around the third capstan 706B, which results in the end effector 200 pivoting downward and to the left about the articulation joint 300. As discussed earlier, this downwards movement of the end effector 200 is compensated for in the knife firing subsystem by the differential 520. Rotation in the opposite direction by the third articulation puck 706A unwinds the third articulation cable 406 to return the end effector 200 to a position substantially coaxial with the shaft assembly 600A (e.g., coaxial with the roll axis RA).

The fourth articulation puck assembly 708 includes a fourth articulation puck 708A, a fourth capstan 708B, and a fourth torsion spring 708C. The fourth articulation puck 708A is provided on an outer face of the lower frame 700B and directly engages the robotic platform 2000. The fourth capstan 708B is coupled to the fourth articulation puck 708A and winds the third articulation cable 408 therearound. The fourth capstan 708B is rotationally affixed to a fourth pivot pin 732 (which is integral with the fourth articulation puck 708A). The fourth capstan 708B is biased by a fourth torsion spring 708C in a retracting direction to maintain a minimum level of tension in the third articulation cable 408. As the fourth articulation puck assembly 708 does not include any gearing, the diameter of the fourth capstan 708B is what dictates the mechanical advantage achieved.

In use, and for example, rotation of the fourth capstan 708B by the robotic platform 2000, via the fourth articulation puck 708A, in a first direction winds the fourth articulation cable 408 around the fourth capstan 708B, which results in the end effector 200 pivoting downwards and to the right about the articulation joint 300. As discussed earlier, this downwards movement of the end effector 200 is compensated for in the knife firing subsystem by the differential 520. Rotation in the opposite direction by the fourth articulation puck 708A unwinds the fourth articulation cable 408 to return the end effector 200 to a position substantially coaxial with the shaft assembly 600A (e.g., coaxial with the roll axis RA).

Of course, and as discussed above, synchronous movement of various combinations of the puck assemblies 702, 704, 706, 708 enables the clinician (via the robotic platform 2000) to position the end effector 200 at any orientation.

Figure 37:
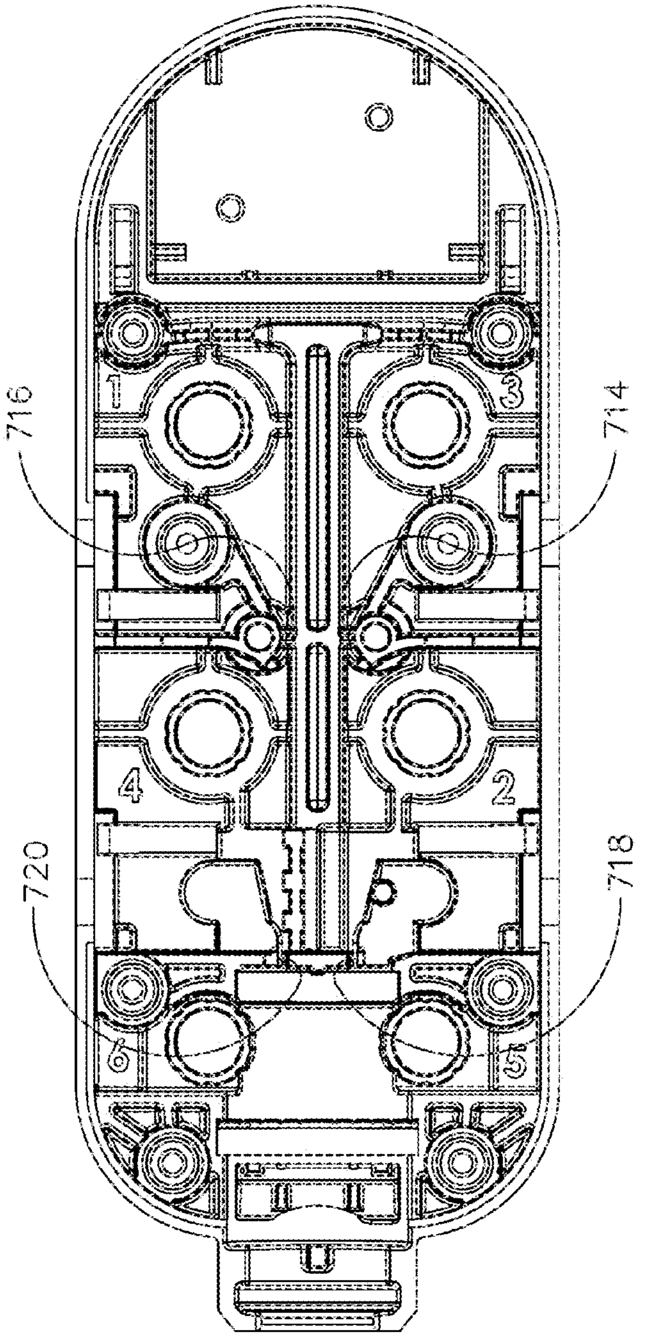
FIG. 37 is a schematic top view of the housing with the upper shroud, middle frame thereof removed, and certain subsystem components removed, in accordance with the disclosed technology.

Additionally, as shown particularly in FIG. 37, the housing 700 (e.g., the lower frame 700B, as shown in FIG. 37) may be provided with a plurality of static redirects 714, 716, 718, 720 that each have a surface that engages a respective articulation cable 402, 404, 406, 408 to redirect it within the housing 700. These redirects 714, 716, 718, 720 ensure proper routing of the articulation cables 402, 404, 406, 408.

VII. 2. Housing and Roll Subsystem

Further to the above, the shaft roll puck assembly 710 includes a shaft roll puck 710A, a first screw gear 710B, and a second screw gear 710C. The shaft roll puck 710A is provided on an outer face of the lower frame 700B, is integral with a fifth pivot pin 734, and directly engages the robotic platform 2000. The first screw gear 710B is coaxial with and rotatable with the shaft roll puck 710A. The second screw gear 710C is meshed with the first screw gear 710B and coupled with the rotatable outer shaft 602.

In use, and for example, rotation of the first screw gear 710B by the robotic platform 2000, via the shaft roll puck 710A, in a first direction turns the second screw gear 710C to roll the outer shaft 602 (e.g., in a clockwise direction about the roll axis RA), as discussed in greater detail above. Rotation of the first screw gear in an opposite second direction causes the outer shaft 602 to roll in an opposite direction (e.g., a counterclockwise direction about the roll axis RA).

VII. 3. Housing and Firing Subsystem

Further to the above, the firing puck assembly includes a firing puck 712A, a drive gear 712A1, a geartrain 712B, and a driven gear or pinion 712C. The firing puck 712A is provided on an outer face of the lower frame 700B, is integral with a sixth pivot pin 736, and directly engages the robotic platform 2000. The drive gear 712A1 directly rotates with the firing puck 712A. As particularly shown in FIG. 23, the geartrain 712B is rotatable with the firing puck 712A and the drive gear 712A1. In some embodiments, the geartrain 712B includes a first idler gear 712B1 meshed with the drive gear 712A1, a second idler gear 712B2 coaxial with and rotationally affixed to the first idler gear 712B1, and a third idler gear 712B3 meshed with the second idler gear 712B2. The pinion 712C is coaxial with and rotationally affixed to the third idler gear 712B3. Further, the pinion 712C meshes with the rack 530 of the firing rod 502 to effect translational movement thereof (to fire and retract the knife 206, as discussed above).

In use, and for example, rotation of the firing puck 712A by the robotic platform 2000 causes rotation of the drive gear 712A1, which in turn drives the geartrain 712B to rotate the pinion 712C. Depending on the direction of rotation of the firing puck 712A, the firing rod 502 is either moved in a distal direction (i.e., towards the end effector 200) to close the anvil 204 and/or fire the knife 206 or a proximal direction (i.e., towards a rear of the housing 700) to retract the knife 206 and/or open the anvil 204.

VIII. OPERATIONAL ALGORITHMS

Figure 49:
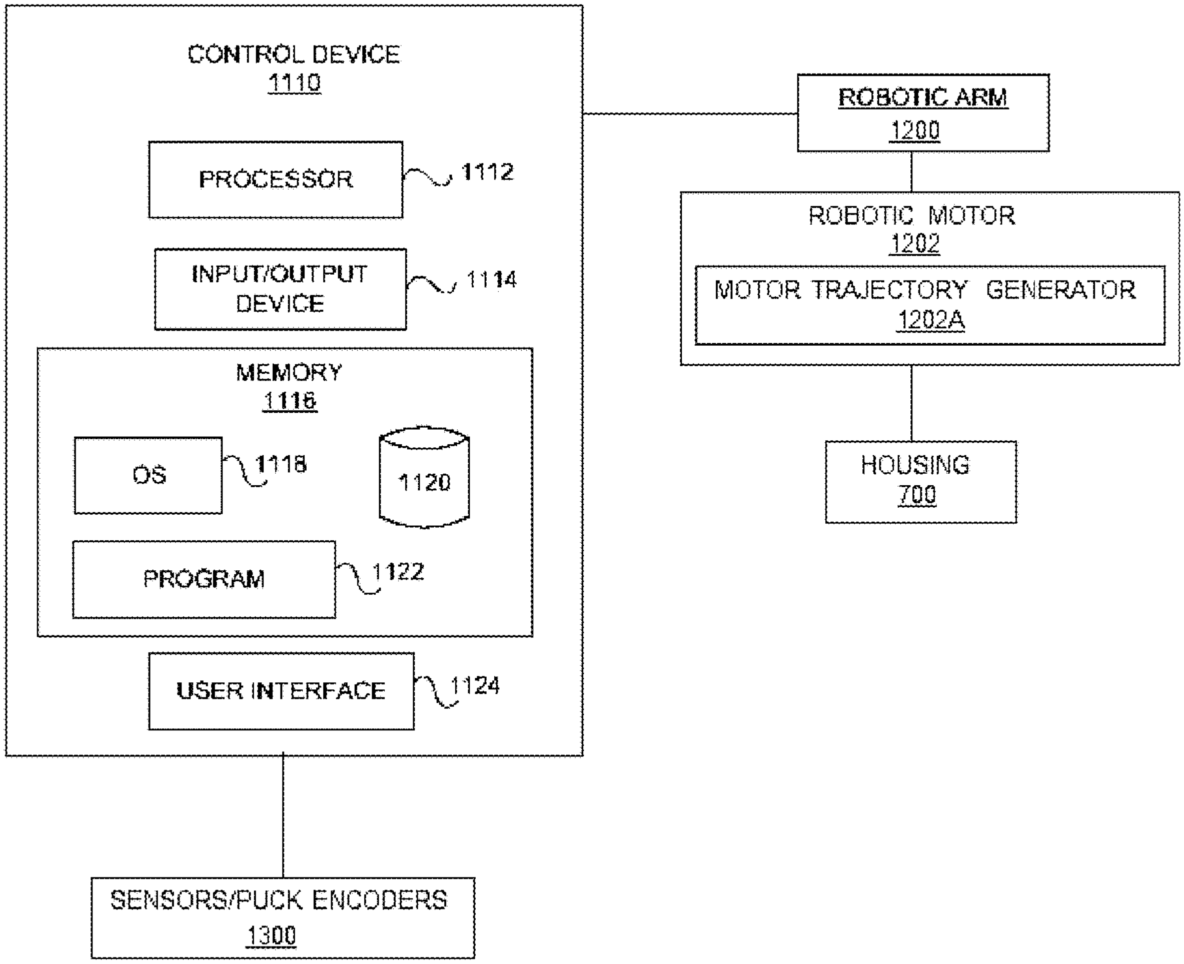
FIG. 49 is a schematic block diagram of a control device, robotic arm, and the surgical instrument, in accordance with the disclosed technology.

FIG. 49 is an illustration of an example control device 1110 for controlling the robotic arm 1200 and the surgical device 1000 via the handle 700. As shown, the control device 1110 can include a processor 1112; an input/output device 1114; and a memory 1116 containing an operating system (OS) 1118, a storage device 1120, which can be any suitable repository of data, and a program 1122. The input/output device can be configured to receive and to output commands to control the robotic arm 1200 and the surgical device 1000. The control device 1110 can include a user interface (U/I) 1124 device for receiving user input data (e.g., from a physician, technician, etc.), such as data representative of a click, a scroll, a tap, a press, movement of a control lever, or typing on an input device that can detect tactile inputs. The control device 1110 can include a display.

The control device 1110 can include a peripheral interface, which can include the hardware, firmware, and/or software that enables communication with various peripheral devices, such as media drives (e.g., magnetic disk, solid state, or optical disk drives), other processing devices, or any other input source used in connection with the instant techniques. The peripheral interface can include a serial port, a parallel port, a general-purpose input and output (GPIO) port, a game port, a universal serial bus (USB), a micro-USB port, a high definition multimedia (HDMI) port, a video port, an audio port, a Bluetooth™ port, a WiFi port, a near-field communication (NFC) port, another like communication interface, or any combination thereof to communicate with other devices via wired or wireless connections or networks, whether local or wide area, private or public, as known in the art. A power source can be configured to provide an appropriate alternating current (AC) or direct current (DC) to power the components.

The processor 1112 can include one or more of an application specific integrated circuit (ASIC), programmable logic device, microprocessor, microcontroller, digital signal processor, co-processor or the like or combinations thereof capable of executing stored instructions and operating upon stored data. The memory 1116 can include one or more suitable types of memory (e.g., volatile or non-volatile memory, random access memory (RAM), read-only memory (ROM), programmable read-only memory (PROM), erasable programmable read-only memory (EPROM), electrically erasable programmable read-only memory (EEPROM), magnetic disks, optical disks, floppy disks, hard disks, removable cartridges, flash memory, a redundant array of independent disks (RAID), and the like) for storing files including the operating system 1118, application programs 1122 (including, for example, a web browser application, a widget or gadget engine, and or other applications, as necessary), executable instructions and data. One, some, or all of the processing techniques described herein can be implemented as a combination of executable instructions and data within the memory 1116.

The processor 1112 can be one or more known processing devices, such as a microprocessor from the Pentium™ family manufactured by Intel™, the Turion™ family manufactured by AMD™, or the Cortex™ family or SecurCore™ manufactured by ARM™ to provide just a few examples. The processor 1112 can constitute a single-core or multiple-core processor that executes parallel processes simultaneously. For example, the processor 1112 can be a single-core processor that is configured with virtual processing technologies. One of ordinary skill in the art will understand that other types of processor arrangements could be implemented that provide for the capabilities disclosed herein.

The control device 1110 can include one or more storage devices 1120 configured to store information used by the processor 1112 (or other components) to perform at least some of the functions disclosed herein. As an example, the control device 1110 can include memory 1116 that includes instructions to enable the processor 1112 to execute one or more applications, network communication processes, and any other type of application or software known to be available on computer systems. Alternatively, the instructions, application programs, or other software can be stored in an external storage and/or can be available from a remote memory over a network. The one or more storage devices can be a volatile or non-volatile, magnetic, semiconductor, tape, optical, removable, non-removable, or other type of storage device or tangible computer-readable medium.

The control device 1110 can include memory 1116 that includes instructions that, when executed by the processor 1112, perform one or more processes consistent with the functionalities disclosed herein. Methods, systems, and articles of manufacture consistent with disclosed embodiments are not limited to separate programs or computers configured to perform dedicated tasks. For example, the control device 1110 can include memory 1116 that can include one or more programs 1122 to perform one or more functions of the disclosed technology. For example, the control device 1110 can access one or more programs 1122, that, when executed, perform at least one function disclosed herein. One or more programs 1122 can be configured to receive input from a user (e.g., a physician, a technician, etc.) and cause the control device 1110 to output one or more control signals to the robotic arm 1200. The one or more programs 1122 can be configured to cause the user interface 1124 to display images indicative of a function or condition associated with the robotic arm 1200.

The memory 1116 of the control device 1110 can include one or more memory devices that store data and instructions used to perform one or more of the methods and features disclosed herein. The memory 1116 can include software components that, when executed by the processor 1112, perform one or more processes consistent with those disclosed herein. The control device 1110 can include any number of hardware and/or software applications that are executed to facilitate any of the operations. The one or more I/O interfaces 1114 can be utilized to receive or collect data and/or user instructions from a wide variety of input devices. Received data can be processed by one or more computer processors 1112 as desired in various implementations of the disclosed technology and/or stored in one or more memory devices.

While the control device 1110 has been described above for implementing the techniques described herein, those having ordinary skill in the art will appreciate that other functionally equivalent techniques can be employed. For example, as known in the art, some or all of the functionality implemented via executable instructions can also be implemented using firmware and/or hardware devices such as application specific integrated circuits (ASICs), programmable logic arrays, state machines, etc. Furthermore, the control device 1110 can include a greater or lesser number of components than those illustrated and/or described above.

As those skilled in the art will appreciate, the control device 1110 described above may be implemented within the robotic platform 2000 or any other structure (e.g., a computing system separate from the robotic platform 2000).

Moreover, the control device 1110 is in communication with one or more sensors 1300 integrated with the surgical instrument 1000 or puck encoders 1300 integrated with the robotic platform 2000. By way of example, the one or more sensors 1300 may include one or more magnetic rotary position encoders which are configured to identify the rotational position of a motor 1202 of the robotic arm 1200, the shaft assembly 600A (e.g., a roll angle of the outer shaft 602), and/or the end effector 200 of the surgical instrument 1000. In some examples, the magnetic rotary position encoders may be coupled to the processor 1112. The sensors 1300 may also include current, velocity, and other forms of position sensors necessary to implement the following processes.

VIII. 1. Cable Compensation During Maypoling

Cable driven medical instruments (such as endocutters, e.g., 2-degree of freedom staplers) require the shaft to roll relative to the cables. In the presently described surgical instrument 1000, the outer shaft 602 rolls relative to the articulation cables 402, 404, 406, 408. When that happens, and as discussed above, the cables go through a twist and winding motion around a center tube known as maypoling. Some applications, such as the presently described surgical instrument 1000, wind the cables around a center tube that can be either stationary or non-stationary. Such motion causes the cables to stretch because the distance between the fixed surface that the cables leave in the proximal handle (e.g., handle 700) and the surface through which they enter the shaft (e.g., outer shaft 602) which is rotating with roll, changes as a function of roll. When that happens, the cable undergoes unintended stretch, causing an increase in cable tension proportional to cable stiffness. For polymer cables or fishing lines, the stiffness is low such that the increase in cable tension during roll is insignificant. For metal cables, such as tungsten or stainless steel, such increase in cable tension is not insignificant. By way of example, a roll of 320 degrees causes greater than a 1.5 mm stretch in a stainless-steel cable. This equates to 70-90 Newton (N) increase in cable tension, which is roughly one-third of the available tension increase. In other words, when the articulation cables 402, 404, 406, 408 are wrapped around the maypole tube 608, the cables 402, 404, 406, 408, if not compensated, they are pulled on tighter proportionally.

In order to substantially eliminate cable stretch and its equivalent rise in cable tension, the presently disclosed technology includes a control system including the control device 1110 operable to execute the processes described in the following paragraphs to release the cables 402, 404, 406, 408 (via, e.g., cable motors 1202) proportional to the roll angle, thereby compensating for the roll. Compensation, in the context of the present disclosure, means that as the roll subsystem 500 is rolled, the articulation cables 402, 404, 406, 408 are "let out", even if the current articulation angle at the articulation joint 300 is maintained, so as not to overstress the articulation cables 402, 404, 406, 408. Furthermore, in order to tune the behavior of the articulation joint 300 during maypoling, a partial compensation factor between approximately 80%-90% of an idealized compensation length can be utilized to adjust the total changed cable compensation length (discussed in greater detail below). This partial compensation factor is adjustable in order to give the articulation joint 300 a "solid" (i.e., higher tension in the cables) versus "soft" (i.e., lower tension in the cables) behavior during roll while also preventing the loss of tension by not fully compensating. The partial compensation factor also simplifies the kinematic model of maypoling by allowing the controller to ignore the effect of friction and cable flattening (i.e., change in cable diameter) during maypoling.

As discussed above in section VI. 1., the presently described surgical instrument 1000 includes configurations that employ a maypoling section that allow the articulation cables 402, 404, 406, 408 to wind around a shaft (e.g., the maypole tube 608) when the surgical instrument 1000 is rolled, such as up to 320 degrees in a clockwise or counterclockwise direction. It is noted that, while the foregoing description focuses on maypoling as it relates to the maypole tube 608, the following also applies to scenarios where the articulation cables 402, 404, 406, 408 maypole around another shaft (e.g., the firing rod 502) as well as other various cable driven medical instruments, (which do not currently compensate for cable stretching during maypoling).

In accordance with the present disclosure, and with reference to FIG. 39, a maypoling length (L) is a distance between (1) the fixed surface in the proximal handle 700 that the cable(s) 402, 404, 406, 408 exit (i.e., exemplary point P1 along the cable, proximal or within the handle 700, that is rotationally restricted/restrained), and a surface inside the outer shaft 602, which rotates with the outer shaft 602 (e.g. exemplary point P2 shown in FIGS. 38 and 39 where the articulation cables 402, 404, 406, 408 engage the inner shaft 604), that the cables re-enter. The region along the maypoling length (L) is also referred to as the maypoling section or region, with a section of the cables 402, 404, 406, 408 running therealong/therethrough. Furthermore, for a given cable diameter (d) and a given center/maypole tube diameter (D) around which the cable(s) 402, 404, 406, 408 can wind, a trigonometric relationship can be defined between the roll angle (B) and the delta displacement that each cable needs to undergo in order to maintain the tension in the cable prior to maypoling (also referred to herein as the "initial tension"). Additionally, prior to maypoling, each cable is located at a cable position (R), which refers to the radial distance from the center of the maypole tube 608 to the center of the cable. Certain parameters, such as the cable position (R), cable diameter (d) and maypole tube diameter (D) are known constants, while other inputs, such as the roll angle (B) may be obtained in any appropriate way by the control device 1110 (e.g., by one of the sensors/encoders 1300). More specifically, the roll angle (B) can be measured via a puck encoder and divided by the roll gear ratio between the roll puck 710A and the outer shaft 602.

Figure 43:
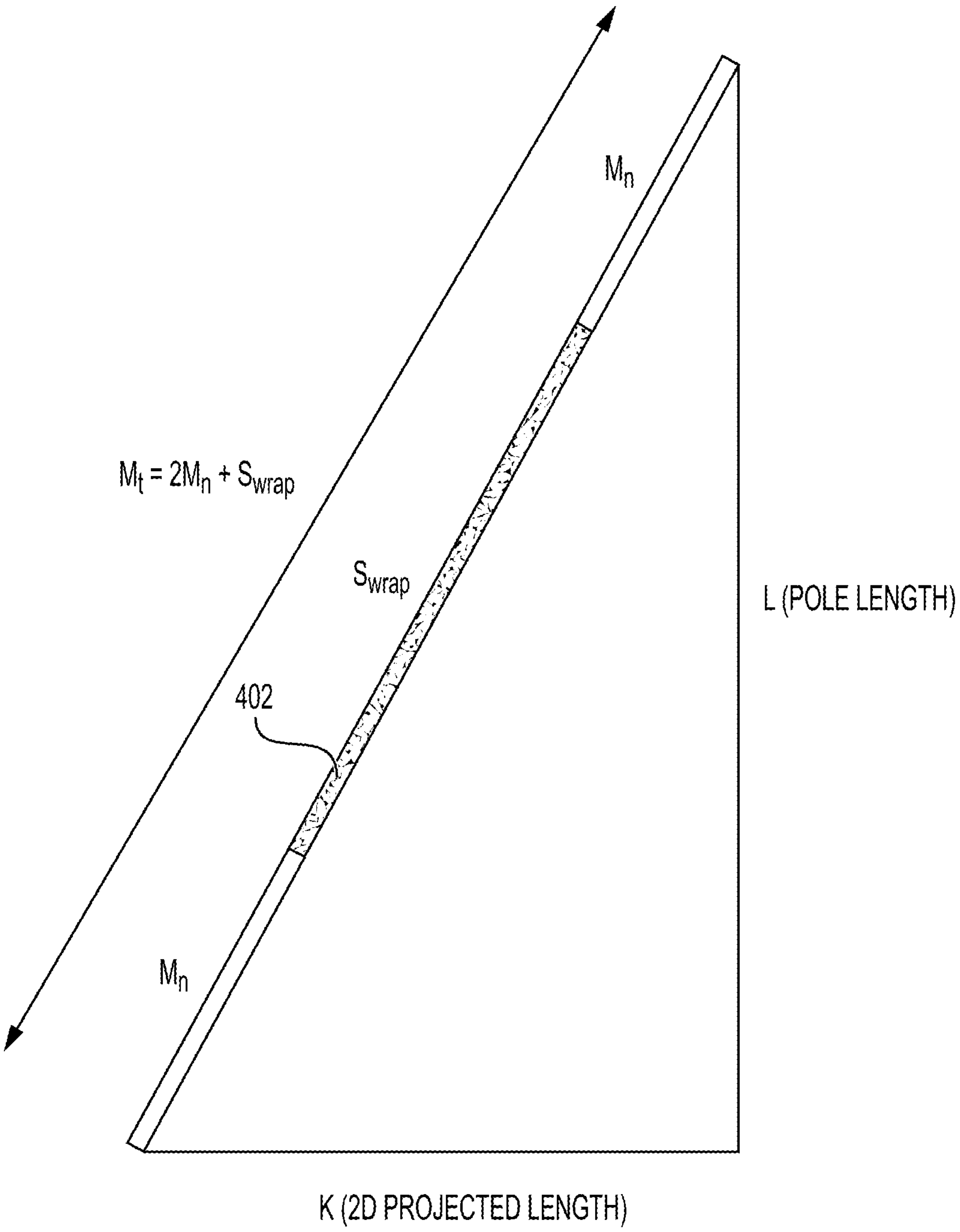
FIG. 43 is a schematic depiction of a transfer function modeling of a cable length after maypoling, in accordance with the disclosed technology.
Figure 44:
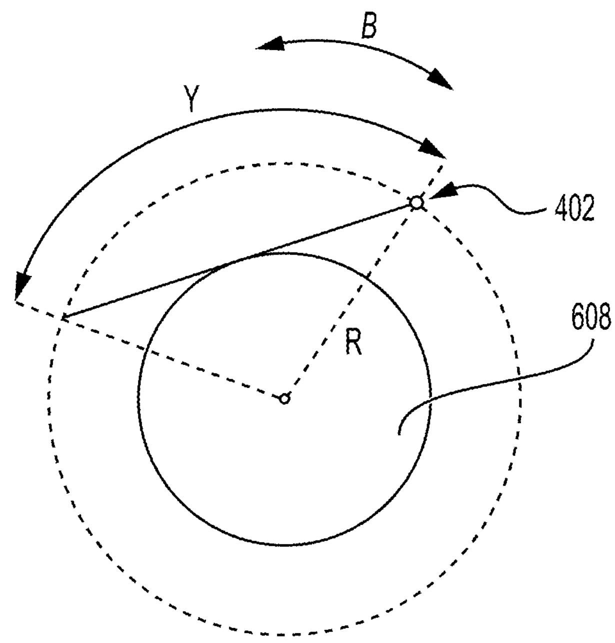
FIG. 44 is a schematic cross-sectional view of an articulation cable and maypole tube, in a case where a roll angle of the cable is less than or equal to a no-contact angle, in accordance with the disclosed technology.

For the purpose of concise description, articulation cable 402 is described herein as exemplary to the operation of the control device 1110. It will be appreciated by those skilled in the art that the following concepts are equivalently applicable to any and all cables implemented in the surgical instrument 1000 that maypole in a similar manner. FIG. 43 conceptually depicts a transfer function modeling of the presently described maypoling system. While the maypoling action occurs in a three-dimensional space, with the cable 402 wrapping in a helix shape about tube 608, with the assumption that the cable 402 is kept at the same tension throughout maypoling as the initial tension (i.e., it is not stretched), the cable 402 can be trigonometrically modelled in a two-dimensional space using a right triangle, where one side is the tube length (L), one side is the two-dimensional projected length (K), and the hypotenuse is the total maypoled length ($M_t$) of the cable 402, which can be defined by the following equation:

$$M_t = 2M_n + S_{wrap} \tag{1}$$

where $M_n$ is the length of the entrance and exit cones (i.e., the portion of the cable 402 that does not wrap around the maypole tube 608) and $S_{wrap}$ is the length of the cable 402 that does wrap around the maypole tube 608.

The presently described maypoling system is also governed by the following two equations:

$$a = \frac{D + d}{2} \tag{2}$$

-continued $$\gamma = 2\cos^{-1}\frac{a}{R} \tag{3}$$

where a is the helix radius when the cable 402 maypoles around the maypole tube 608, and γ is the no-contact angle. The two-dimensional projected length (K), in some cases, is the result of the radius (or diameter) of the wrap circle (which is the distance between the center of the maypole tube to the center of one of the cables), multiplied by the sine of the wrap angle B, and is discussed in greater detail below. The no-contact angle is the maximum angle the cable 402 can roll to without coming into contact with the maypole tube 608, since the cable 402 is initially spaced away from the maypole tube 608 (at cable position (R)) prior to maypoling. Consequently, two distinct cases are possible (either the cable 402 contacts the maypole tube 608, which is referred to herein as the "capstan effect", or it does not), both of which are governed by a different set of equations. The "capstan effect" referred to is known as the effect of an increase in cable tension proportional to the wrap angle of a cable around a sliding surface or a pulley.

A case (referred to herein as Case I) where |B| is less than or equal to γ is represented in FIG. 53, which is a schematic cross-sectional view of a cable 402 and maypole tube 608 where there is no capstan effect. In other words, the cable 402 is not rolled to a sufficiently large angle that the helix shape of the maypoled cable 402 results in the cable contacting the maypole tube 608. Case I is governed by the following equations:

$$K = 2R\sin\frac{|B|}{2} \tag{4}$$

$$M_t = \sqrt{L^2 + K^2} \tag{5}$$

Figure 45:
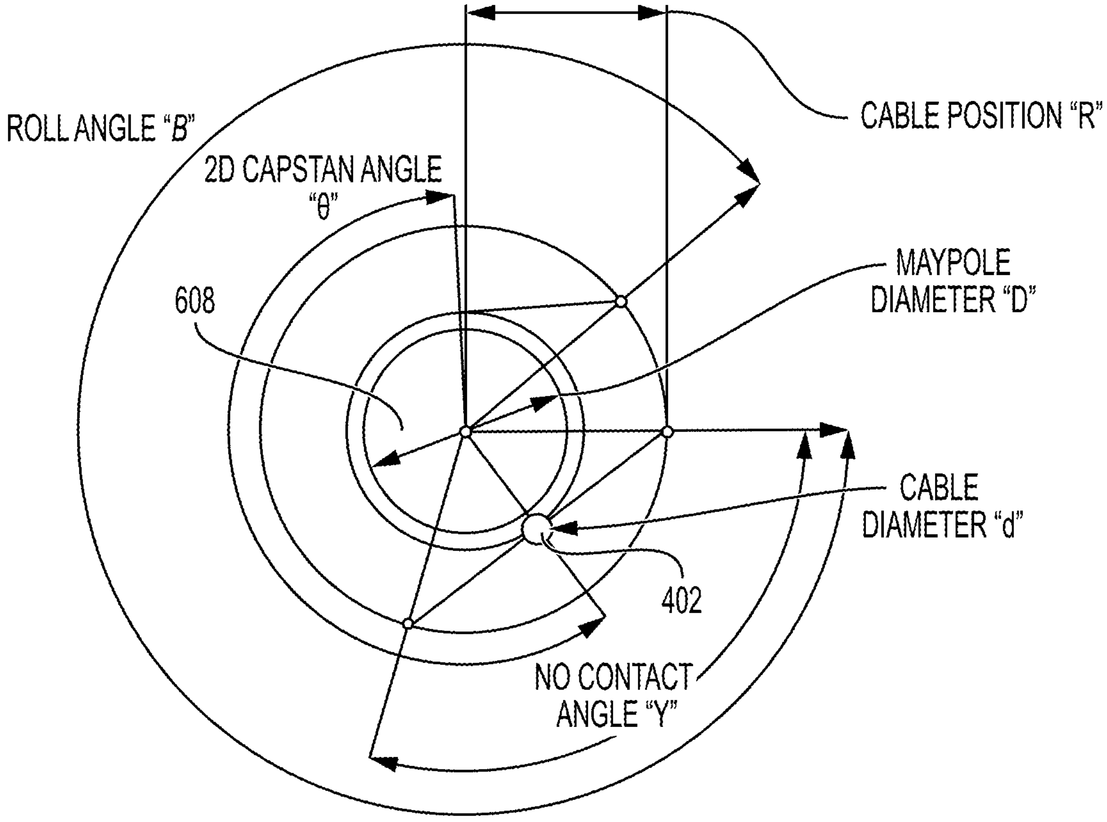
FIG. 45 is a schematic cross-sectional view of an articulation cable and maypole tube, in a case where a roll angle of the cable is greater than the no-contact angle, in accordance with the disclosed technology.

The other case (referred to herein as Case II) where |B| is greater than γ is represented in FIG. 45, which is a schematic cross-sectional view of a cable 402 and maypole tube 608 where there is a capstan effect. In other words, the cable 402 is rolled (by virtue of its rotational relationship with the outer shaft 602) to a sufficiently large angle that the helix shape of the maypoled cable 402 results in the cable contacting the maypole tube 608. Case II is governed by the following equations:

$$\theta = |B| - \gamma \tag{6}$$

$$K = a\theta + 2\sqrt{R^2 - a^2} \tag{7}$$

$$M_t = \sqrt{L^2 + K^2} \tag{8}$$

where θ is the projected two-dimensional capstan angle, which corresponds to the roll angle of the shaft (e.g., the outer shaft 602) minus the no-contact angle γ. Effectively, it is the angle of wrap around the maypole tube. It is noted that, in the present system, the cables 402, 404, 406, 408 do not start wrapping around the maypole tube 608 immediately. In other words, there is a certain roll of the shaft that has to happen before wrapping commences, and that no-contact zone is defined by the length (L) of the maypoling section, the diameter of the maypole tube 608 and the diameter of the cable 402.

In view of the above, a maypoling transfer function is governed by the three below equations:

$$\forall\, |B| \leq \gamma,\ K = 2R \sin\frac{B}{2} \tag{9}$$

$$\forall\, |B| > \gamma,\ K = a\theta + 2\sqrt{R^2 - a^2} \tag{10}$$

$$\Delta L = \sqrt{L^2 + K^2} - L \tag{11}$$

where ΔL is an idealized change in length (L) of the articulation cable 402 (or, equivalently stated, a length of the section of the articulation cable 402 in the maypoling region) to account for its maypoling when the outer shaft 602 is rolled such that tension in the cable 402 is kept constant. In the context of the presently described system that utilizes surgical instrument 1000, control device 1110, and robotic platform 2000, using the constants, inputs and equations discussed above, the necessary change in length (ΔL) in the articulation cable 402 can be calculated. Once calculated, this value can be used by the control device 1110 and/or robotic platform 2000 to cause, via the robotic motor 1202 of the robotic arm 1200, the articulation puck assembly 702 to unwind a length of cable from the capstan 702B equal to the change in length (ΔL). As those skilled in the art will appreciate, this unwinding can be dynamically done as the outer shaft 602 rolls and the articulation cable 402 maypoles. In other words, as the roll angle B changes, the length of cable unwound by the articulation puck assembly 702 can be changed to maintain the desired tension in the cable 402.

Figure 46A:
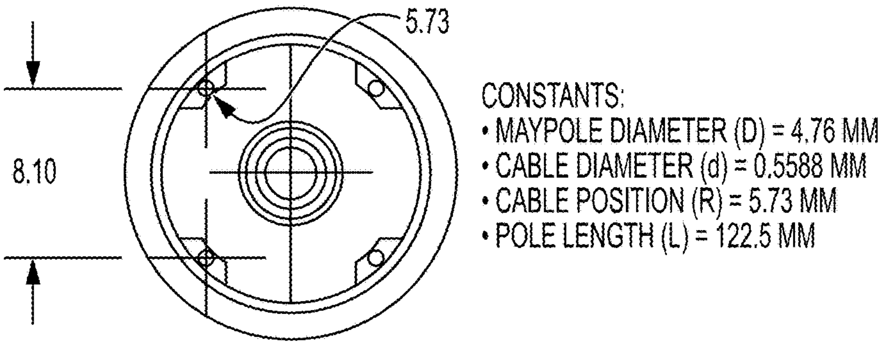
FIG. 46A is a schematic cross-sectional view of an exemplary maypole and articulation cables, in accordance with the disclosed technology.
Figure 46B:
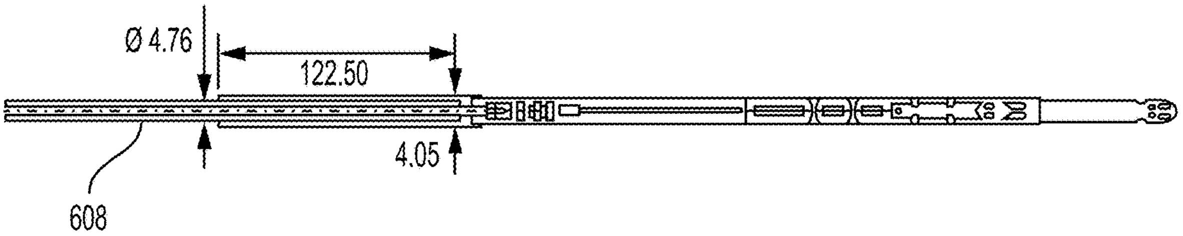
FIG. 46B is a schematic side cross-sectional view of the exemplary maypole and articulation cables of FIG. 46A, shown with other components of the surgical instrument, in accordance with the disclosed technology.
Figure 47:
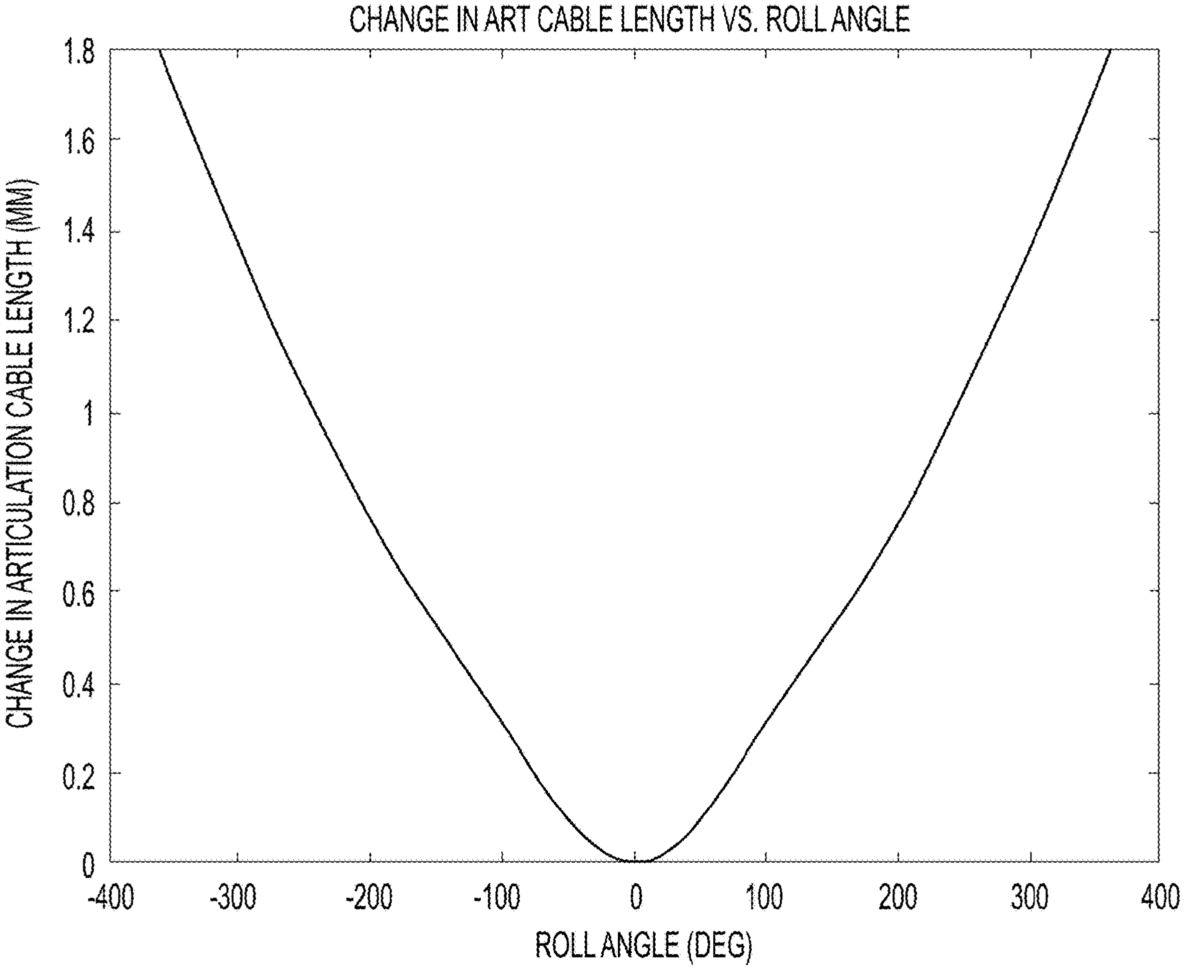
FIG. 47 is a schematic graphical depiction of a change in articulation cable length versus roll angle using the surgical instrument of FIGS. 46A-46B, in accordance with the disclosed technology.

FIGS. 46A-47 depict an example of maypoling compensation modeling, in accordance with the present disclosure. The dimensions shown are, of course, exemplary, and are not intended to limit the spirit and scope of the present disclosure in any way. Making reference to FIG. 56, with the exemplary dimensions of the surgical instrument shown in FIGS. 46A-46B, a graph of the maypoling transfer function (ΔL over different B) is shown. At 360 degrees of shaft roll, there is approximately 1.8 millimeters of cable stretch. In an idealized case, Lengthening the cable by 1.8 millimeters would keep tension constant. Depending on the material used for the articulation cable 402, 1.8 millimeters may or may not be significant. It is also noted that this transfer function can be approximated using a linear polynomial, the coefficients of which can be configured based on experimental data, otherwise known as mapping.

While the above accounts for an ideal environment, those skilled in the art will appreciate that such a maypoling relationship is also a function of friction between the cable and the surface around which it is maypoling. With friction being difficult to measure/predict and being a variable over time, such influence can be eliminated by using a partial compensation approach, where the idealized kinematics can be multiplied by a fixed factor less than 1, or by a relationship of factors as a function of roll making the compensation adaptable for different wrist behaviors, while at the same time preventing the loss of tension in the cable 402 by intentionally under-compensating. For example, experimental testing has shown that such partial compensation approach reduces the non-compensated change in tension from 30-40 N to closer to 10 N if at 85% compensation while still maintaining sufficient residual tension to offset a friction effect and preventing the cable 402 from going slack. Thus, the presently described process can further calculate a cable compensation length (ΔL') by multiplying the determined change in length (ΔL) of the cable by a factor between 0 and 1.

Figure 48:
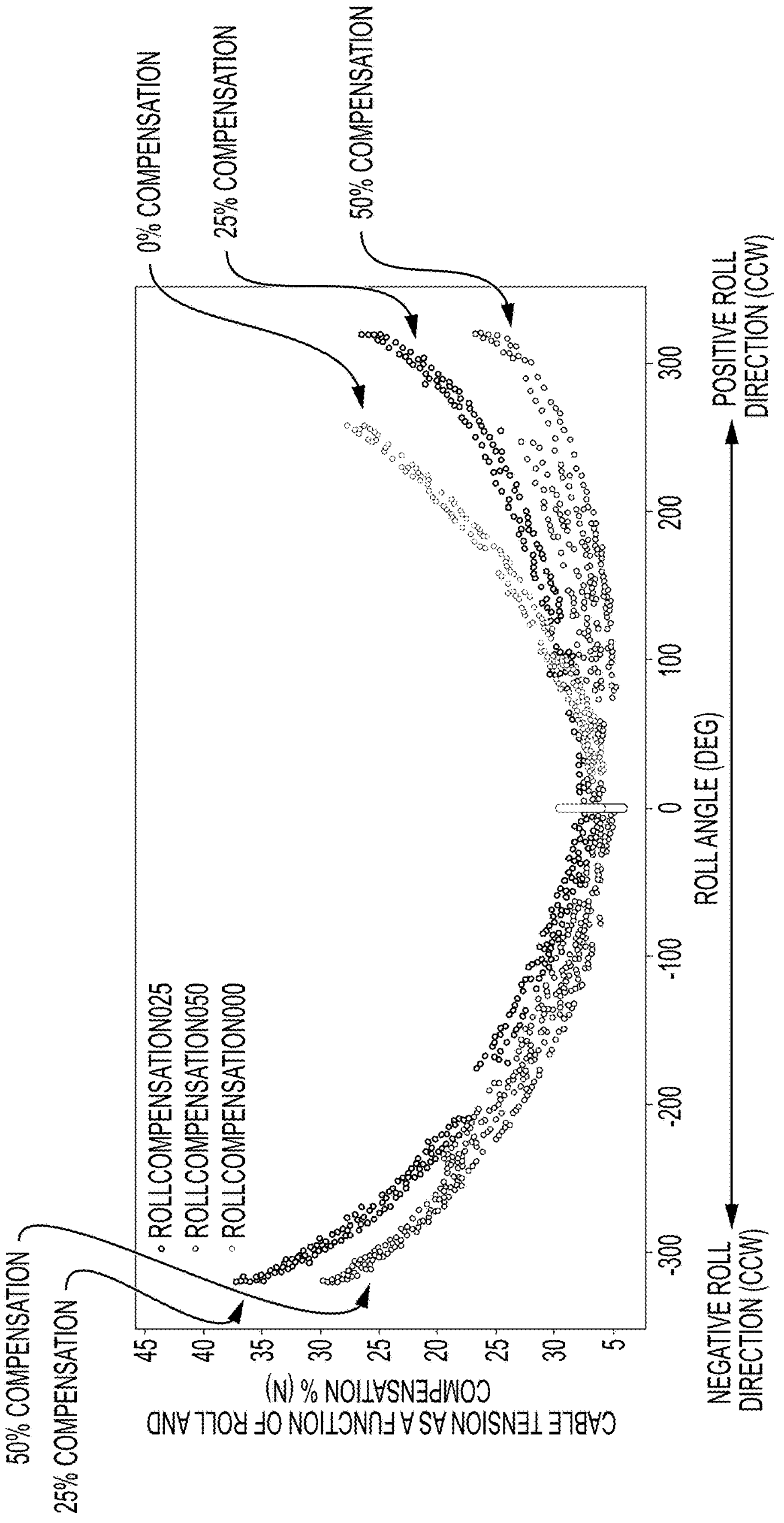
FIG. 48 is a schematic graphical depiction of exemplary changes in cable tension as a function of roll and compensation percentage, in accordance with the disclosed technology.

FIG. 48 graphically depicts other exemplary changes in cable tension as a function of roll and compensation percentage and illustrates the effect compensating for the maypoling of the articulation cable 402 has on the cable tension. As shown, cable tension drops as a function of a more aggressive compensation factor.

IX. CLAUSES

The disclosed technology described herein can be further understood according to the following clauses:

Clause 1. A surgical instrument (1000) comprising: a shaft assembly (600A) comprising: a rotatable outer shaft (602) configured to rotate about a roll axis (RA); and a maypole tube (608) housed within the outer shaft; a firing rod (502) that extends within the maypole tube (608) and is configured to move a knife (206) in an end effector (200); one or more articulation cables (402, 404, 406, 408), each articulation cable (402, 404, 406, 408) being configured (i) to be manipulable to cause rotation of the end effector (200) about at least one of a pitch axis (PA) and a yaw axis (YA) and (ii) to wrap around the maypole tube (608) when the rotatable outer shaft (602) rotates about the roll axis (RA).

Clause 2. The surgical instrument (1000) of clause 1, further comprising: a shaft roll puck assembly (710) comprising: a rotatable shaft roll puck (710A); a first screw gear (710B) rotatable with the shaft roll puck (710A); and a second screw gear (710C) meshed with the first screw gear (710B) and coupled to the outer shaft (602), wherein rotation of the shaft roll puck (710A) rotates the first screw gear (710B), which rotates the second screw gear (710C), which rotates the outer shaft (602) about the roll axis (RA).

Clause 3. The surgical instrument (1000) of clause 1, further comprising: a shaft roll puck assembly (710') comprising: a rotatable shaft rollpuck (710A'); a first input capstan (710B1') rotatable with the shaft roll puck (710A'); a second input capstan (710B2') rotatable with the shaft roll puck (710A'); an output drum (710C') connected to the outer shaft (602); a first roll cable (711B1') connecting the first input capstan (710B1') and the output drum (710C'); and a second roll cable (711B2') connecting the second input capstan (710B2') and the output drum (710C'), wherein rotation of the shaft roll puck (710A) rotates the first input capstan (710B1') and the second input capstan (710B2'), which causes either: (i) the first roll cable (711B1') to wrap around the first input capstan (710B1') and second roll cable (711B2') to unwrap from the second input capstan (710B2'), thereby rotating the output drum (710C') and the outer shaft (602) in a first direction about the roll axis (RA), or (ii) the first roll cable (711B1') to unwrap from the first input capstan (710B1') and second roll cable (711B2') to wrap around the second input capstan (710B2'), thereby rotating the output drum (710C') and the outer shaft (602) in a second direction about the roll axis (RA).

Clause 4. The surgical instrument (1000) of any one of clauses 1-3, wherein the maypole tube (608) entirely surrounds at least a portion of the firing rod (502).

Clause 5. The surgical instrument (1000) of any one of clauses 1-4, further comprising a housing (700) configured to engage a robotic platform (2000), a proximal end (608A) of the maypole tube (608) being disposed in the housing (700).

Clause 6. The surgical instrument (1000) of clause 5, the proximal end (608A) being flared.

Clause 7. The surgical instrument (1000) of any one of clauses 5-6, further comprising an inner shaft (604) rotationally fixed to the outer shaft (602), the maypole tube (608) extending from the housing (700) to the inner shaft (604).

Clause 8. The surgical instrument (1000) of clause 7, the inner shaft (604) comprising one or more support channels (605) that rotationally constrain the one or more articulation cables (402, 404, 406, 408).

Clause 9. The surgical instrument (1000) of any one of clauses 7-8, the one or articulation cables (402, 404, 406, 408) being rotationally unconstrained in a region of the surgical instrument (1000) that (i) surrounds the maypole tube (608) and (ii) extends approximately an entire length of the maypole tube (608).

Clause 10. The surgical instrument (1000) of any one of clauses 1-9, the maypole tube (608) comprising a rigid material.

Clause 11. The surgical instrument (1000) of any one of clauses 1-9, the maypole tube (608) comprising a bendable material.

Clause 12. The surgical instrument (1000) of any one of clauses 10-11, the maypole tube (608) comprising a lubricious additive material.

Clause 13. A control device (1110) for adjusting a length of a cable (402) of a surgical instrument (1000), the surgical instrument comprising the cable and a shaft (602), the cable comprising (i) a section with an initial length (L) defined between a rotatable point (P2) of the cable that is rotatable with the shaft relative to a rotationally restrained proximal point (P1) of the cable and (ii) an initial tension at a zero degree roll angle, the control device being configured to: receive a non-zero degree roll angle (B) of the rotatable point (P2) of the cable that is rotated with the shaft relative to the rotationally restrained proximal point (P1) of the cable; determine a change in length (ΔL) of the section of the cable (402), relative to the initial length (L), that maintains the cable (402) at the initial tension; calculate a cable compensation length by multiplying the determined change in length (ΔL) of the section of the cable (402) by a factor; and deliver a signal to change the length of the section of the cable based on the calculated cable compensation length.

Clause 14. The control device (1110) of clause 13, wherein the factor is between 0 and 1.

Clause 15. The control device (1110) of clause 14, wherein the factor is between approximately 0.5 and 0.85.

Clause 16. A surgical system comprising: a surgical instrument (1000) comprising: a housing (700); a shaft assembly (600A) extending from the housing (700) and comprising: an outer shaft (602) configured to rotate about a roll axis (RA); and a maypole tube (608) housed within the outer shaft; and a cable (402) comprising a rotationally restrained point (P1) proximal the housing (700) and a rotatable point (P2) that is rotatable with the outer shaft (602), the cable (402) comprising, at a zero-degree roll angle, a length (L) defined between the rotationally restrained point (P1) and the rotatable point (P2); and a control device (1110) for adjusting the length of the cable, the control device (1110) being configured to: receive a non-zero degree roll angle (B) of rotatable point (P2) of the cable (402) relative to the rotationally restrained proximal point (P1) of the cable; determine a change in length (ΔL) of the cable (402), relative to the length (L) of the cable (402) at the zero-degree roll angle, that maintains the cable (402) at a same tension as the tension in the cable (402) when the cable (402) is at the zero-degree roll angle; calculate a cable compensation length by multiplying the determined change in length (ΔL) of the cable by a factor; and deliver a signal to change the length of the cable based on the calculated cable compensation length.

Clause 17. The surgical system of clause 16, wherein the control device (1110) comprises a robotic platform (2000), the housing (700) comprises a puck assembly (702) that connects with the robotic platform (2000), and the puck assembly (702) is configured to receive the signal to change the length of the cable (402) by unwinding the cable (402) from the puck assembly (702).

Clause 18. The surgical system of any one of clauses 16-17, wherein the factor is between 0 and 1.

Clause 19. The surgical system of clause 18, wherein the factor is between approximately 0.5 and 0.85.

Clause 20. The surgical system of any one of clauses 16-19, wherein the surgical instrument (1000) comprises firing rod (502), and the maypole tube (608) entirely surrounds at least a portion of the firing rod (502).

The embodiments described above are cited by way of example, and the present invention is not limited by what has been particularly shown and described hereinabove. Rather, the scope of the invention includes both combinations and sub combinations of the various features described and illustrated hereinabove, as well as variations and modifications thereof which would occur to persons skilled in the art upon reading the foregoing description and which are not disclosed in the prior art.

What is claimed is:

1. A surgical instrument comprising:
a shaft assembly comprising:
a rotatable outer shaft configured to rotate about a roll axis; and
a maypole tube housed within the outer shaft;
a firing rod that extends within the maypole tube and is configured to move a knife in an end effector; and
one or more articulation cables, each articulation cable being configured (i) to be manipulable to cause rotation of the end effector about at least one of a pitch axis and a yaw axis and (ii) to wrap around the maypole tube when the rotatable outer shaft rotates about the roll axis.

2. The surgical instrument of claim 1, further comprising:
a shaft roll puck assembly comprising:
a rotatable shaft roll puck;
a first screw gear rotatable with the shaft roll puck; and
a second screw gear meshed with the first screw gear and coupled to the outer shaft,
wherein rotation of the shaft roll puck rotates the first screw gear, which rotates the second screw gear, which rotates the outer shaft about the roll axis.

3. The surgical instrument of claim 1, further comprising:
a shaft roll puck assembly comprising:
a rotatable shaft roll puck;
a first input capstan rotatable with the shaft roll puck;
a second input capstan rotatable with the shaft roll puck;
an output drum connected to the outer shaft;
a first roll cable connecting the first input capstan and the output drum; and
a second roll cable connecting the second input capstan and the output drum, wherein rotation of the shaft roll puck rotates the first input capstan and the second input capstan, which causes either:

(i) the first roll cable to wrap around the first input capstan and second roll cable to unwrap from the second input capstan, thereby rotating the output drum and the outer shaft in a first direction about the roll axis, or (ii) the first roll cable to unwrap from the first input capstan and second roll cable to wrap around the second input capstan, thereby rotating the output drum and the outer shaft in a second direction about the roll axis.

4. The surgical instrument of claim 1, wherein the maypole tube entirely surrounds at least a portion of the firing rod.

5. The surgical instrument of claim 1, further comprising a housing configured to engage a robotic platform, a proximal end of the maypole tube being disposed in the housing.

6. The surgical instrument of claim 5, the proximal end being flared.

7. The surgical instrument of claim 5, further comprising an inner shaft rotationally fixed to the outer shaft, the maypole tube extending from the housing to the inner shaft.

8. The surgical instrument of claim 7, the inner shaft comprising one or more support channels that rotationally constrain the one or more articulation cables.

9. The surgical instrument of claim 7, the one or articulation cables being rotationally unconstrained in a region of the surgical instrument that (i) surrounds the maypole tube and (ii) extends approximately an entire length of the maypole tube.

10. The surgical instrument of claim 1, the maypole tube comprising a rigid material.

11. The surgical instrument of claim 10, the maypole tube comprising a lubricious additive material.

12. The surgical instrument of claim 1, the maypole tube comprising a bendable material.

* * * * *